US008101739B2

(12) United States Patent
Sullivan et al.

(10) Patent No.: US 8,101,739 B2
(45) Date of Patent: Jan. 24, 2012

(54) RECOMBINANT EXPRESSION VECTORS COMPRISING A HUMAN CODON-OPTIMIZED MARBURG VIRUS (MARV) ANGOLA GLYCOPROTEIN GENE INSERT AND METHOD OF IMMUNIZATION EMPLOYING SAID VECTOR

(75) Inventors: Nancy Sullivan, Kensington, MD (US); Bimal Chakrabarti, Gaithersberg, MD (US); Zhi-Yong Yang, Potomac, MD (US); Maria Grazia Pau, Leiden (NL); Jaap Goudsmit, Amsterdam (NL); Gary Nabel, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 618 days.

(21) Appl. No.: 11/662,869

(22) PCT Filed: Sep. 27, 2005

(86) PCT No.: PCT/US2005/034798
§ 371 (c)(1),
(2), (4) Date: Mar. 2, 2009

(87) PCT Pub. No.: WO2006/037038
PCT Pub. Date: Apr. 6, 2006

(65) Prior Publication Data
US 2009/0232841 A1 Sep. 17, 2009

Related U.S. Application Data

(60) Provisional application No. 60/613,883, filed on Sep. 27, 2004, provisional application No. 60/677,606, filed on May 3, 2005, provisional application No. 60/679,767, filed on May 10, 2005, provisional application No. 60/701,694, filed on Jul. 22, 2005, provisional application No. 60/715,874, filed on Sep. 9, 2005.

(51) Int. Cl.
C07H 21/04 (2006.01)
A61K 39/12 (2006.01)
(52) U.S. Cl. .................... 536/23.72; 424/204.1
(58) Field of Classification Search .................. None
See application file for complete search history.

(56) References Cited

FOREIGN PATENT DOCUMENTS

| WO | WO 99/32147 | 7/1999 |
|---|---|---|
| WO | WO 03/028632 | 4/2003 |
| WO | WO 03/092582 A2 | 11/2003 |

OTHER PUBLICATIONS

Bray, M., 2003, Defense against filoviruses used as biological weapons, Antivir. Res. 57:53-60.*
Bente, D., et al., 2009, Disease modeling for Ebola and Marburg viruses, Dis. Models Mech. 2:12-17.*
Feldmann, H., et al., 2003, Ebola virus: from discovery to vaccine, Nat. Rev. Immunol. 3:677-685.*
Mohamadzadeh, M., et al., 2007, How Ebola and Marburg viruses battle the immune system, Nat. Rev. Immunol. 7:556-567.*
Baize, S. et al. (1999) "Defective humoral responses and extensive intravascular apoptosis are associated with fatal outcome in Ebola virus-infected patients." Nat. Med. 5:423-426.
Cao, J. et al. (1996) "Molecular determinants of acute single-cell lysis by human immunodeficiency virus type 1." J. Virol. 70:1340-1354.
Chan, S.Y. et al. (2000) "Differential induction of cellular detachment by envelope glycoproteins of Marburg and Ebola (Zaire) viruses." J. Gen. Virol. 81:2155-2159.
Fallaux, F.J. et al. (1996) "Characterization of 911: A new helper cell line for the titration and propagation of early region 1—deleted adenoviral vectors." Hum. Gene Ther. 7:215-222.
Fallaux, F.J. et al. (1998) "New helper cells and matched early region 1—deleted adenovirus vectors prevent generation of replication-competent adenoviruses." Hum. Gene Ther. 9:1909-1917.
Geisbert, T.W. et al. (2003) "Pathogenesis of Ebola hemorrhagic fever in cynomolgus macaques: Evidence that dendritic cells are early and sustained targets of infection." Am. J. Pathol. 163:2347-2370.
Hartikka, J. et al. (1996) "An improved plasmid DNA expression vector for direct injection into skeletal muscle." Hum. Gene Ther. 7:1205-1217.
Havenga, M.J.E. et al. (2001) "Improved adenovirus vectors for infection of cardiovascular tissues." J. Virol. 75:3335-3342.
International Preliminary Report on Patentability from PCT/US2005/034798.
Jahrling, P.B. et al. (1996) "Passive immunization of Ebola virus-infected cynomolgus monkeys with immunoglobulin from hyperimmune horses." Arch. Virol. Suppl. 11:135-140.
Jones, S.M. et al. (2005) "Live attenuated recombinant vaccine protects nonhuman primates against Ebola and Marburg viruses." Nat. Med. 11:786-790.
Manicassamy, B. et al. (2005) "Comprehensive analysis of ebola virus GP1 in viral entry." J. Virol. 79:4793-4805.
Nanda, A. et al. (2005) "Immunogenicity of recombinant fiber-chimeric adenovirus serotype 35 vector-based vaccines in mice and rhesus monkeys." J. Virol. 79:14161-14168.
Prevots, D.R. et al. (2000) "Poliomyelitis prevention in the United States. Updated recommendations of the Advisory Committee on Immunization Practices (ACIP)." MMWR Recomm. Rep. 49:1-22.
Sanchez, A. et al. (1998) "Biochemical analysis of the secreted and virion glycoproteins of Ebola virus." J. Virol. 72:6442-6447.
Shabram, P.W. et al. (1997) "Analytical anion-exchange HPLC of recombinant type-5 adenoviral particles." Hum. Gene Ther. 8:453-465.
Sullivan, N.J. et al. (2000) "Development of a preventive vaccine for Ebola virus infection in primates." Nature 408:605-609.

(Continued)

Primary Examiner — Jeffrey S. Parkin
(74) Attorney, Agent, or Firm — Kilpatrick Townsend & Stockton LLP

(57) ABSTRACT

The invention is related to a nucleic acid molecule comprising a polynucleotide encoding a modified filovirus glycoprotein (GP) having at least one amino acid change located in a relatively conserved region of said GP that decreases in vitro cytotoxicity and retains immunogenicity when compared to in vitro cytotoxicity and immunogenicity of a wild type filovirus GP, and related modified filovirus GPs, plasmid DNAs, recombinant viruses, adenoviruses, pharmaceutical compositions, vaccine compositions, antibodies that are specifically reactive with the modified filovirus GPs, and related methods of making and using the same.

8 Claims, 44 Drawing Sheets

OTHER PUBLICATIONS

Sullivan, N.J. et al. (2003) "Accelerated vaccination for Ebola virus haemorrhagic fever in non-human primates." *Nature* 424:681-684.

Sullivan, N. et al. (2003) "Ebola virus pathogenesis: implications for vaccines and therapies." *J. Virol.* 77:9733-9737.

Sullivan, N.J. et al. (2005) "Ebola virus glycoprotein toxicity is mediated by a dynamin-dependent protein-trafficking pathway." *J. Virol.* 79:547-553.

Sullivan, N.J. et al. (2006) "Immune protection of nonhuman primates against Ebola virus with single low-dose adenovirus vectors encoding modified GPs." *PLoS Med.* 3: e177, pp. 0865-0873.

Takada, A. et al. (2000) "Downregulation of β integrins by Ebola virus glycoprotein: implication for virus entry." *Virology* 278:20-26.

Volchkov, V.E. et al. (1995) "GP mRNA of Ebola virus is edited by the Ebola virus polymerase and by T7 and vaccinia virus polymerases." *Virology* 214:421-430.

Waldrop, S.L. et al. (1998) "Normal human CD4+ memory T cells display broad heterogeneity in their activation threshold for cytokine synthesis." *J. Immunol.* 161:5284-5295.

Wilson, J.A. et al. (2001) "Protection from Ebola virus mediated by cytotoxic T lymphocytes specific for the viral nucleoprotein." *J Virol.* 75:2660-2664.

Xu, L. et al. (1998) "Immunization for Ebola virus infection." *Nat. Med.* 4:37-42.

Yang, Z.Y. et al. (2000) "Identification of the Ebola virus glycoprotein as the main viral determinant of vascular cell cytotoxicity and injury." *Nat. Med.* 6:886-889.

Yang, Z.Y. et al. (2004) "pH-dependent entry of severe acute respiratory syndrome coronavirus is mediated by the spike glycoprotein and enhanced by dendritic cell transfer through DC-SIGN." *J. Viro.* 78:5642-5650.

\* cited by examiner

CMV/R-Ebola GP(S/G)(G TO A)/h

Kan.

CMV IE Enhancer/Promoter

CMV IE Splicing Acceptor

SaLI(1344)
EcoRV(1352)

VRC 6612
6426 bp

102G/A

XbaI(2012)

Ebola GP(S/G)/h

Tbgh
BgdI(3399)
EcoRI(3399)

VRC 6612 (SEQ ID NO: 1)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca acgaccccg cccattgacg tcaataatga cgtatgttcc
 481 catagtaacg ccaataggga ctttccattg acgtcaatgg gtggagtatt tacggtaaac
 541 tgcccacttg gcagtacatc aagtgtatca tatgccaagt acgccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt tgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tcccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt ccttccatg
1321 ggtcttttct gcagtcaccg tcgtcgacga tatcgccgcc atggagggcc tgagcctgct
1381 gcagctgccc agggacaagt tcaggaagag cagcttcttc gtgtgggtga tcatcctgtt
1441 ccagaaggcc ttcagcatgc ccctgggcgt ggtgaccaac agcaccctgg aggtgaccga
1501 gatcgaccag ctggtgtgca aggaccacct ggccagcacc gaccagctga agagcgtggg
1561 cctgaacctg gagggcagcg gcgtgagcac cgacatcccc agcgccacca gaggtggg
1621 cttcaggagc ggcgtgcctc caaggtggt gagctacgag gccgccgagt gggccgagaa
1681 ctgctacaac ctggagatca agaagcccga cggcagcgag tgcctgcctc ctcctcctga
1741 cggcgtgagg ggcttcccca ggtgcaggta cgtgcacaag gccagggca ccggcccctg
1801 ccccggcgac tacgccttcc acaaggacgg cgccttcttc ctgtacgaca ggctggccag
1861 caccgtgatc tacagggggcg tgaacttcgc cgagggcgtg atcgccttcc tgatcctggc
1921 caagcccaag gagaccttcc tgcagagccc tcccatcagg gaggccgtga actacaccga
1981 gaacaccagc agctactacg ccaccagcta tctagagtac gagatcgaga acttcggcgc
2041 ccagcacagc accaccctgt tcaagatcga caacaacacc tccgtgaggc tggacaggcc
2101 ccacaccccc cagttcctgt tccagctgaa cgacaccatc ccctgcacc agcagctgag
2161 caacaccacc ggcaggctga tctggaccct ggacgccaac atcaacgccg acatcggcga
2221 gtgggcttc tgggagaaca agaagaacct gagcgagcag ctgaggggcg aggagctgag
2281 cttcgaggcc ctgagcctga acgagaccga ggacgacgac gccgccagca gcaggatcac
2341 caagggcagg atcagcgaca gggccaccag gaagtacagc gacctggtgc caagaacag
2401 ccccggcatg gtgccctgc acatccccga gggcgagacc ccctgcccca gcagaacag
2461 caccgagggc aggaggtgg gcgtgaacac ccaggagacc atcaccgaga ccgccgccac
2521 catcatcggc accaacggca accacatgca gatcagcacc atcggcatca ggcccagcag
2581 cagccagatc cccagcagca gccccaccac cgcccctagc ccgaggcc agacccccac
2641 caccacacc agcggaccca gcgtgatggc caccgaggag cccaccaccc tcccggcag
2701 cagccccgga cccaccaccg aggcccctac cctgaccacc cctgagaaca tcaccaccgc
2761 cgtgaagacc gtgctgcccc aggagagcac cagcaacggc ctgatcacca gcaccgtgac
2821 cggcatcctg gcagcctgg gcctgaggaa gaggagcagg aggcagacca acaccaaggc
2881 caccggccaa tgcaaccca acctgcacta ctggaccgcc aggagcagc acaacgccgc
2941 cggcatcgcc tggatccct acttcggccc cggcgccgag ggcatctaca ccgagggcct
```

FIG. 1B-2

```
3001 gatgcacaac cagaacgccc tggtgtgcgg cctgaggcag ctggccaacg agaccaccca
3061 ggccctgcag ctgttcctga gggccaccac cgagctgagg acctacacca tcctgaacag
3121 gaaggccatc gacttcctgc tgaggaggtg gggcggcacc tgcaggattc tgggccccga
3181 ctgctgcatc gagccccacg actggaccaa gaacatcacc gacaagatca accagatcat
3241 ccacgacttc atcgacaacc ctctgcccaa ccaggacaac gacgacaact ggtggaccgg
3301 ctggcggcag tggataccctg ccggcatcgg catcaccggc atcatcatcg ccatcatcgc
3361 tctgctgtgc gtgtgcaagc tgctgtgctg agaattcaga tctacacgat ctgctgtgcc
3421 ttctagttgc cagccatctg ttgtttgccc ctcccccgtg ccttccttga ccctggaagg
3481 tgccactccc actgtccttt cctaataaaa tgaggaaatt gcatcgcatt gtctgagtag
3541 gtgtcattct attctggggg gtggggtggg gcaggacagc aaggggggagg attgggaaga
3601 caatagcagg catgctgggg atgcggtggg ctctatgggt acccaggtgc tgaagaattg
3661 acccgttcc tcctgggcca gaaagaagca ggcacatccc cttctctgtg acacaccctg
3721 tccacgcccc tggttcttag ttccagcccc actcatagga cactcatagc tcaggagggc
3781 tccgccttca atcccaccccg ctaaagtact tggagcggtc tctccctccc tcatcagccc
3841 accaaaccaa acctagcctc caagagtggg aagaaattaa agcaagatag gctattaagt
3901 gcagagggag agaaaatgcc tccaacatgt gaggaagtaa tgagagaaat catagaattt
3961 taaggccatg atttaaggcc atcatggcct taatcttccg cttcctcgct cactgactcg
4021 ctgcgctcgg tcgttcggct gcggcgagcg gtatcagctc actcaaaggc ggtaatacgg
4081 ttatccacag aatcagggga taacgcagga agaacatgt gagcaaaagg ccagcaaaag
4141 gccaggaacc gtaaaaaggc cgcgttgctg gcgtttttcc ataggctccg cccccctgac
4201 gagcatcaca aaaatcgacg ctcaagtcag aggtggcgaa acccgacagg actataaaga
4261 taccaggcgt ttccccctgg aagctccctc gtgcgctctc ctgttccgac cctgccgctt
4321 accggatacc tgtccgcctt tctcccttcg ggaagcgtgg cgctttctca tagctcacgc
4381 tgtaggtatc tcagttcggt gtaggtcgtt cgctccaagc tgggctgtgt gcacgaaccc
4441 cccgttcagc ccgaccgctg cgccttatcc ggtaactatc gtcttgagtc aacccggta
4501 agacacgact tatcgccact ggcagcagcc actggtaaca ggattagcag agcgaggtat
4561 gtaggcggtg ctacagagtt cttgaagtgg tggcctaact acggctacac tagaagaaca
4621 gtatttggta tctgcgctct gctgaagcca gttaccttcg gaaaaagagt tggtagctct
4681 tgatccggca aacaaaccac cgctggtagc ggtggttttt tgtttgcaa gcagcagatt
4741 acgcgcagaa aaaaggatc tcaagaagat cctttgatct ttctacggg gtctgacgct
4801 cagtggaacg aaaactcacg ttaagggatt ttggtcatga gattatcaaa aaggatcttc
4861 acctagatcc ttttaaatta aaaatgaagt tttaaatcaa tctaaagtat atatgagtaa
4921 acttggtctg acagttacca atgcttaatc agtgaggcac ctatctcagc gatctgtcta
4981 tttcgttcat ccatagttgc ctgactcggg gggggggggc gctgaggtct gcctcgtgaa
5041 gaaggtgttg ctgactcata ccaggcctga atcgccccat catccagcca gaaagtgagg
5101 gagccacggt tgatgagagc tttgttgtag gtggaccagt tggtgatttt gaacttttgc
5161 tttgccacgg aacggtctgc gttgtcggga agatgcgtga tctgatcctt caactcagca
5221 aaagttcgat ttattcaaca aagccgccgt cccgtcaagt cagcgtaatg ctctgccagt
5281 gttacaacca attaaccaat tctgattaga aaaactcatc gagcatcaaa tgaaactgca
5341 atttattcat atcaggatta tcaataccat attttgaaa aagccgtttc tgtaatgaag
5401 gagaaaactc accgaggcag ttccatagga tggcaagatc ctggtatcgg tctgcgattc
5461 cgactcgtcc aacatcaata caacctatta atttcccctc gtcaaaaata aggttatcaa
5521 gtgagaaatc accatgagtg acgactgaat ccggtgagaa tggcaaaagc ttatgcattt
5581 ctttccagac ttgttcaaca ggccagccat tacgctcgtc atcaaaatca ctcgcatcaa
5641 ccaaaccgtt attcattcgt gattgcgcct gagcgagacg aaatacgcga tcgctgttaa
5701 aaggacaatt acaaacagga atcgaatgca accggcgcag gaacactgcc agcgcatcaa
5761 caatattttc acctgaatca ggatattctt ctaatacctg gaatgctgtt ttcccggga
5821 tcgcagtggt gagtaaccat gcatcatcag gagtacggat aaaatgcttg atggtcggaa
5881 gaggcataaa ttccgtcagc cagtttagtc tgaccatctc atctgtaaca tcattggcaa
```

FIG. 1B-3

```
5941 cgctaccttt gccatgtttc agaaacaact ctggcgcatc gggcttccca tacaatcgat
6001 agattgtcgc acctgattgc ccgacattat cgcgagccca tttataccca tataaatcag
6061 catccatgtt ggaatttaat cgcggcctcg agcaagacgt ttcccgttga atatggctca
6121 taacaccect tgtattactg tttatgtaag cagacagttt tattgttcat gatgatatat
6181 ttttatcttg tgcaatgtaa catcagagat tttgagacac aacgtggctt tccccccccc
6241 cccattattg aagcatttat cagggttatt gtctcatgag cggatacata tttgaatgta
6301 tttagaaaaa taaacaaata ggggttccgc gcacatttcc ccgaaaagtg ccacctgacg
6361 tctaagaaac cattattatc atgacattaa cctataaaaa taggcgtatc acgaggccct
6421 ttcgtc
```

| FIG. 1B | FIG. 1B-1 |
| --- | --- |
| | FIG. 1B-2 |
| | FIG. 1B-3 |

CMV/R Ebola GP(Z)(full length G to A)/h
CMV Enhancer/Promoter
Kan.
HTLV-1 R Region
CMV IE Splicing Acceptor
EcoRV(1352)
VRC 6615
6424 bp
G to A
XbaI(2097)
GP(Z)(full length)/h
BamHI(2693)
Tbgh
BgdI(3406)
EcoRI(3399)
TM
I>V

VRC 6615 (SEQ ID NO: 2)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca acgaccccg cccattgacg tcaataatga cgtatgttcc
 481 catagtaacg ccaataggga ctttccattg acgtcaatgg gtggagtatt tacggtaaac
 541 tgcccacttg gcagtacatc aagtgtatca tatgccaagt acgccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt tgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tcccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt cctttccatg
1321 ggtcttttct gcagtcaccg tcgtcgacga tatcgccgcc atgggcgtga ccggcatcct
1381 gcagctgccc agggacaggt tcaagaggac cagcttcttc ctgtgggtga tcatcctgtt
1441 ccagaggacc ttcagcatcc ccctgggcgt gatccacaac agcaccctgc aggtgagcga
1501 cgtggacaag ctggtgtgca gggacaagct gagcagcacc aaccagctga ggagcgtggg
1561 cctgaacctg gagggcaacg gcgtggccac cgacgtgccc agcgccacca gaggtggggg
1621 cttcaggagc ggcgtgcctc ccaaggtggt gaactacgag gccgccgagt gggccgagaa
1681 ctgctacaac ctggagatca agaagcccga cggcagcgag tgcctgcccg ccgcccctga
1741 cggcatcagg ggcttcccca ggtgcaggta cgtgcacaag gtgagcggca ccggccctg
1801 cgccggcgac ttcgccttcc acaaggaggg cgccttcttc ctgtacgaca ggctggccag
1861 caccgtgatc tacaggggca ccaccttcgc cgagggcgtg gtggccttcc tgatcctgcc
1921 ccaggccaag aaggacttct tcagcagcca ccctctgagg gagcccgtga acgccaccga
1981 ggaccccagc agcggctact acagcaccac catcaggtac caggccaccg gcttcggcac
2041 caacgagacc gagtacctgt tcgaggtgga caacctgacc tacgtgcagc tggagtctag
2101 attcacccct cagttcctgc tgcagctgaa cgagaccatc tacaccagcg gcaagaggag
2161 caacaccacc ggcaagctga tctggaaggt gaaccccgag atcgacacca ccatcggcga
2221 gtgggccttc tgggagacca agaagaacct gaccaggaag atcaggagcg aggagctgag
2281 cttcaccgtc gtgagcaacg ggccaagaa catcagcggc cagagcccg ccaggaccag
2341 cagcgacccc ggcaccaaca ccaccaccga ggaccacaag atcatggcca gcagaaacag
2401 cagcgccatg gtgcaggtgc acagccaggg cagggaggcc gccgtgagcc acctgaccac
2461 cctggccacc atcagcacca gccctcagtc tttaaccacc aagcccggcc cgacaacag
2521 caccccacaac cccctgtgt acaagctgga catcagcgag gccacccagg tggagcagca
2581 ccacaggagg accgacaacg acagcaccgc cagcgacacc ccttccgcca ccaccgccgc
2641 cggccctccg aaggccgaga acaccaacac cagcaagagc accgactttc tggatcccgc
2701 caccaccacc agccctcaga ccacagcga ccgccggc aacaacaaca cccaccacca
2761 ggacaccggc gaggagagcg ccagcagcgg caagctgggc ctgatcacca acaccatcgc
2821 cggcgtggcc ggcctgatca ccggcggcag gaggaccagg agggaggcca tcgtgaacgc
2881 ccagcccaag tgcaaccca acctgcacta ctggaccacc aggacgagg cgccgccat
2941 cggcctggcc tggattccct acttcggccc cgccgccgag ggcatctaca tcgagggcct
```

FIG. 2B-2

```
3001 gatgcacaac caggacggcc tgatctgcgg cctgaggcag ctggccaacg agaccaccca
3061 ggccctgcag ctgttcctga gggccaccac cgagctgagg accttcagca tcctgaacag
3121 gaaggccatc gacttcctgc tgcagaggtg gggcggcacc tgccacatcc tgggccccga
3181 ctgctgcatc gagcccacg actggaccaa gaacatcacc gacaagatcg accagatcat
3241 ccacgacttc gtggacaaga ccctgccaga ccagggcgac aacgacaact ggtggaccgg
3301 ctggcggcag tggatacctg ccggcatcgg cgtgaccggc gtggtgatcg ccgtgatcgc
3361 tctgttctgc atctgcaagt tcgtgttctg aacacgtgga attcagatct gctgtgcctt
3421 ctagttgcca gccatctgtt gtttgcccct cccccgtgcc ttccttgacc ctggaaggtg
3481 ccactcccac tgtcctttcc taataaaatg aggaaattgc atcgcattgt ctgagtaggt
3541 gtcattctat tctgggggt ggggtggggc aggacagcaa ggggggaggat tgggaagaca
3601 atagcaggca tgctggggat gcggtgggct ctatgggtac ccaggtgctg aagaattgac
3661 ccggttcctc ctgggccaga agaagcagg cacatcccct tctctgtgac acaccctgtc
3721 cacgcccctg gttcttagtt ccagcccac tcataggaca ctcatagctc aggagggctc
3781 cgccttcaat cccacccgct aaagtacttg gagcggtctc tccctccctc atcagcccac
3841 caaaccaaac ctagcctcca agagtgggaa gaaattaaag caagataggc tattaagtgc
3901 agagggagag aaaatgcctc caacatgtga ggaagtaatg agagaaatca tagaatttta
3961 aggccatgat ttaaggccat catggcctta atcttccgct tcctcgctca ctgactcgct
4021 gcgctcggtc gttcggctgc ggcgagcgt atcagctcac tcaaaggcgg taatacggtt
4081 atccacagaa tcaggggata acgcaggaaa gaacatgtga gcaaaaggcc agcaaaaggc
4141 caggaaccgt aaaaaggccg cgttgctggc gtttttccat aggctccgcc ccctgacga
4201 gcatcacaaa aatcgacgct caagtcagag gtggcgaaac ccgacaggac tataaagata
4261 ccaggcgttt ccccctggaa gctccctcgt gcgctctcct gttccgaccc tgccgcttac
4321 cggatacctg tccgcctttc tcccttcggg aagcgtggcg ctttctcata gctcacgctg
4381 taggtatctc agttcggtgt aggtcgttcg ctccaagctg ggctgtgtgc acgaaccccc
4441 cgttcagccc gaccgctgcg ccttatccgg taactatcgt cttgagtcca acccggtaag
4501 acacgactta tcgccactgg cagcagccac tggtaacagg attagcagag cgaggtatgt
4561 aggcggtgct acagagttct tgaagtggtg cctaactac ggctacacta gaagaacagt
4621 atttggtatc tgcgctctgc tgaagccagt taccttcgga aaaagagttg gtagctcttg
4681 atccggcaaa caaccaccg ctggtagcgg tggttttttt gtttgcaagc agcagattac
4741 gcgcagaaaa aaaggatctc aagaagatcc tttgatcttt tctacggggt ctgacgctca
4801 gtggaacgaa aactcacgtt aagggatttt ggtcatgaga ttatcaaaaa ggatcttcac
4861 ctagatcctt ttaaattaaa aatgaagttt taaatcaatc taaagtatat atgagtaaac
4921 ttggtctgac agttaccaat gcttaatcag tgaggcacct atctcagcga tctgtctatt
4981 tcgttcatcc atagttgcct gactcggggg ggggggcgc tgaggtctgc ctcgtgaaga
5041 aggtgttgct gactcatacc aggcctgaat cgccccatca tccagccaga agtgaggga
5101 gccacggttg atgagagctt tgttgtaggt ggaccagttg gtgattttga acttttgctt
5161 tgccacggaa cggtctgcgt tgtcgggaag atgcgtgatc tgatccttca actcagcaaa
5221 agttcgattt attcaacaaa gccgccgtcc cgtcaagtca gcgtaatgct ctgccagtgt
5281 tacaaccaat taaccaattc tgattagaaa aactcatcga gcatcaaatg aaactgcaat
5341 ttattcatat caggattatc aataccatat tttgaaaaa gccgtttctg taatgaagga
5401 gaaaactcac cgaggcagtt ccataggatg gcaagatcct ggtatcggtc tgcgattccg
5461 actcgtccaa catcaataca acctattaat ttcccctcgt caaaaataag gttatcaagt
5521 gagaaatcac catgagtgac gactgaatcc ggtgagaatg gcaaaagctt atgcatttct
5581 ttccagactt gttcaacagg ccagccatta cgctcgtcat caaaatcact cgcatcaacc
5641 aaaccgttat tcattcgtga ttgcgcctga gcgagacgaa atacgcgatc gctgttaaaa
5701 ggacaattac aaacaggaat cgaatgcaac cggcgcagga acactgccag cgcatcaaca
5761 atattttcac ctgaatcagg atattcttct aatacctgga atgctgtttt cccggggatc
5821 gcagtggtga gtaaccatgc atcatcagga gtacggataa aatgcttgat ggtcggaaga
5881 ggcataaatt ccgtcagcca gtttagtctg accatctcat ctgtaacatc attggcaacg
5941 ctaccttgc catgtttcag aaacaactct ggcgcatcgg gcttcccata caatcgatag
6001 attgtcgcac ctgattgccc gacattatcg cgagcccatt tatacccata taaatcagca
```

FIG. 2B-3

```
6061 tccatgttgg aatttaatcg cggcctcgag caagacgttt cccgttgaat atggctcata
6121 acaccccttg tattactgtt tatgtaagca gacagtttta ttgttcatga tgatatattt
6181 ttatcttgtg caatgtaaca tcagagattt tgagacacaa cgtggctttc cccccccccc
6241 cattattgaa gcatttatca gggttattgt ctcatgagcg gatacatatt tgaatgtatt
6301 tagaaaaata aacaaatagg ggttccgcgc acatttcccc gaaaagtgcc acctgacgtc
6361 taagaaacca ttattatcat gacattaacc tataaaaata ggcgtatcac gaggcccttt
6421 cgtc
```

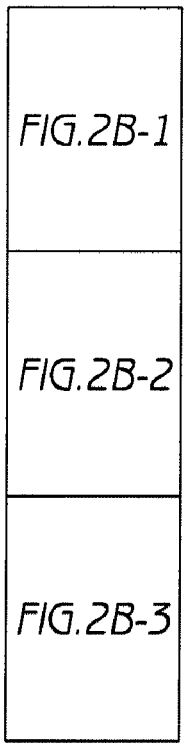

VRC 6613 sequence (SEQ ID NO: 3)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca acgaccccg cccattgacg tcaataatga cgtatgttcc
 481 catagtaacg ccaataggga ctttccattg acgtcaatgg gtggagtatt tacggtaaac
 541 tgcccacttg gcagtacatc aagtgtatca tatgccaagt acgccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt tgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt cctttccatg
1321 ggtcttttct gcagtcaccg tcgtcgacga tatcgccgcc atggagggcc tgagcctgct
1381 gcagctgccc agggacaagt tcaggaagag cagcttcttc gtgtgggtga tcatcctgtt
1441 ccagaaggcc ttcagcatgc ccctgggcgt ggtgaccaac agcaccctgg aggtgaccga
1501 gatcgaccag ctggtgtgca aggaccacct ggccagcacc gaccagctga gagcgtggg
1561 cctgaacctg gacggcagcg gcgtgagcac cgacatcccc agcgccacca gaggtgggg
1621 cttcaggagc ggcgtgcctc ccaaggtggt gagctacgag gccggcgagt gggccgagaa
1681 ctgctacaac ctggagatca agaagcccga cggcagcgag tgcctgcctc tcctcctga
1741 cggcgtgagg ggcttcccca ggtgcaggta cgtgcacaag gcccagggca ccggcccctg
1801 ccccggcgac tacgccttcc acaaggacgg cgccttcttc ctgtacgaca ggctggccag
1861 caccgtgatc tacaggggcg tgaacttcgc cgagggcgtg atcgccttcc tgatcctggc
1921 caagcccaag gagaccttcc tgcagagccc tccatcagg gaggccgtga actacaccga
1981 gaacaccagc agctactacg ccaccagcta tctagagtac gagatcgaga acttcggcgc
2041 ccagcacagc accaccctgt tcaagatcga caacaacacc ttcgtgaggc tggacaggcc
2101 ccacacccct cagttcctgt tccagctgaa cgacaccatc cacctgcacc agcagctgag
2161 caacaccacc ggcaggctga tctggaccct ggacgccaac atcaacgccg acatcggcga
2221 gtgggccttc tgggagaaca gaagaacct gagcgagcag ctgagggcg aggagctgag
2281 cttcgaggcc ctgagcctga cgagaccga ggacgacgac gccgccagca gcaggatcac
2341 caagggcagg atcagcgaca gggccaccag gaagtacagc gacctggtgc caagaacag
2401 cccggcatg gtgcccctgc acatccccga gggcgagacc accctgccca gccagaacag
2461 caccgagggc aggagggtgg cgtgaacac ccaggagacc atcaccgaga ccgccgccac
2521 catcatcggc accaacggca accacatgca gatcagcacc atcggcatca ggcccagcag
2581 cagccagatc cccagcagca gcccaccac cgcccctagc ccgaggccc agaccccac
2641 cacccacacc agcggaccca gcgtgatggc caccgaggag cccaccaccc ctcccggcag
2701 cagccccgga cccaccaccg aggccccac cctgaccacc cctgagaaca tcaccaccgc
2761 cgtgaagacc gtgctgcccc aggagagcac cagcaacggc ctgatcacca gcaccgtgac
2821 cggcatcctg gcagcctgg cctgaggaa gaggagcagg aggcagacca acaccaaggc
2881 caccggcaag tgcaacccca acctgcacta ctggaccgcc caggagcagc acaacgccgc
2941 cggcatcgcc tggattccct acttcggccc cggcgccgag ggcatctaca ccgagggcct
```

FIG. 3B-2

```
3001 gatgcacaac cagaacgccc tggtgtgcgg cctgaggcag ctggccaacg agaccaccca
3061 ggccctgcag ctgttcctga gggcaccac cgagctgagg acctacacca tcctgaacag
3121 gaaggccatc gacttcctgc tgaggaggtg gggcggcacc tgcaggattc tgggccccga
3181 ctgctgcatc gagccccacg actggaccaa gaacatcacc gacaagatca accagatcat
3241 ccacgacttc atcgacaacc ctctgcccaa ccaggacaac gacgacaact ggtggaccgg
3301 ctggcggcag tggataccty ccggcatcgg catcaccggc atcatcatcg ccatcatcgc
3361 tctgctgtgc gtgtgcaagc tgctgtgctg aacacgatct gctgtgcctt ctagttgcca
3421 gccatctgtt gtttgccct cccccgtgcc ttccttgacc ctggaaggtg ccactcccac
3481 tgtcctttcc taataaaatg aggaaattgc atcgcattgt ctgagtaggt gtcattctat
3541 tctgggggt ggggtggggc aggacagcaa gggggaggat tgggaagaca atagcaggca
3601 tgctggggat gcggtgggct ctatgggtac ccaggtgctg aagaattgac ccggttcctc
3661 ctgggccaga agaagcagg cacatcccct tctctgtgac acaccctgtc cacgcccctg
3721 gttcttagtt ccagccccac tcataggaca ctcatagctc aggagggctc cgccttcaat
3781 cccacccgct aaagtacttg gagcggtctc tccctcccctc atcagcccac caaaccaaac
3841 ctagcctcca agagtgggaa gaaattaaag caagataggc tattaagtgc agagggagag
3901 aaaatgcctc caacatgtga ggaagtaatg agagaaatca tagaatttta aggccatgat
3961 ttaaggccat catggcctta atcttccgct tcctcgctca ctgactcgct gcgctcggtc
4021 gttcggctgc ggcgagcggt atcagctcac tcaaaggcgg taatacggtt atccacagaa
4081 tcagggata acgcaggaaa gaacatgtga gcaaaaggcc agcaaaaggc caggaaccgt
4141 aaaaaggccg cgttgctggc gtttttccat aggctccgcc ccctgacga gcatcacaaa
4201 aatcgacgct caagtcagag gtggcgaaac ccgacaggac tataagata ccaggcgttt
4261 ccccctggaa gctccctcgt gcgctctcct gttccgaccc tgccgcttac cggataccty
4321 tccgccttc tcccttcggg aagcgtggcg ctttctcata gctcacgctg taggtatctc
4381 agttcggtgt aggtcgttcg ctccaagctg ggctgtgtgc acgaaccccc cgttcagccc
4441 gaccgctgcg ccttatccgg taactatcgt cttgagtcca acccggtaag acacgactta
4501 tcgccactgg cagcagccac tggtaacagg attagcagag cgaggtatgt aggcggtgct
4561 acagagttct tgaagtggtg gcctaactac ggctacacta gaagaacagt atttggtatc
4621 tgcgctctgc tgaagccagt taccttcgga aaaagagttg gtagctcttg atccggcaaa
4681 caaaccaccg ctggtagcgg tggtttttt gtttgcaagc agcagattac gcgcagaaaa
4741 aaaggatctc aagaagatcc tttgatcttt tctacggggt ctgacgctca gtggaacgaa
4801 aactcacgtt aagggatttt ggtcatgaga ttatcaaaaa ggatcttcac ctagatcctt
4861 ttaaattaaa aatgaagttt taaatcaatc taaagtatat atgagtaaac ttggtctgac
4921 agttaccaat gcttaatcag tgaggcacct atctcagcga tctgtctatt tcgttcatcc
4981 atagttgcct gactcggggg gggggggcgc tgaggtctgc ctcgtgaaga aggtgttgct
5041 gactcatacc aggcctgaat cgccccatca tccagccaga aagtgaggga gccacggttg
5101 atgagagctt tgttgtaggt ggaccagttg gtgattttga acttttgctt tgccacggaa
5161 cggtctgcgt tgtcgggaag atgcgtgatc tgatccttca actcagcaaa agttcgattt
5221 attcaacaaa gccgccgtcc cgtcaagtca gcgtaatgct ctgccagtgt tacaaccaat
5281 taaccaattc tgattagaaa aactcatcga gcatcaaatg aaactgcaat ttattcatat
5341 caggattatc aataccatat ttttgaaaaa gccgtttctg taatgaagga gaaaactcac
5401 cgaggcagtt ccataggatg gcaagatcct ggtatcggtc tgcgattccg actcgtccaa
5461 catcaataca acctattaat ttcccctcgt caaaaataag gttatcaagt gagaaatcac
5521 catgagtgac gactgaatcc ggtgagaatg gcaaaagctt atgcatttct ttccagactt
5581 gttcaacagg ccagccatta cgctcgtcat caaaatcact cgcatcaacc aaaccgttat
5641 tcattcgtga ttgcgcctga gcgagacgaa atacgcgatc gctgttaaaa ggacaattac
5701 aaacaggaat cgaatgcaac cggcgcagga acactgccag cgcatcaaca atattttcac
5761 ctgaatcagg atattcttct aatacctgga atgctgtttt ccgggggatc gcagtggtga
5821 gtaaccatgc atcatcagga gtacggataa aatgcttgat ggtcggaaga ggcataaatt
5881 ccgtcagcca gtttagtctg accatctcat ctgtaacatc attggcaacg ctacctttgc
5941 catgtttcag aaacaactct ggcgcatcgg gcttcccata caatcgatag attgtcgcac
6001 ctgattgccc gacattatcg cgagcccatt tatacccata taaatcagca tccatgttgg
```

FIG. 3B-3

```
6061 aatttaatcg cggcctcgag caagacgttt cccgttgaat atggctcata acaccccttg
6121 tattactgtt tatgtaagca gacagtttta ttgttcatga tgatatattt ttatcttgtg
6181 caatgtaaca tcagagattt tgagacacaa cgtggctttc cccccccccc cattattgaa
6241 gcatttatca gggttattgt ctcatgagcg gatacatatt tgaatgtatt tagaaaaata
6301 aacaaatagg ggttccgcgc acatttcccc gaaaagtgcc acctgacgtc taagaaacca
6361 ttattatcat gacattaacc tataaaaata ggcgtatcac gaggccctt cgtc
```

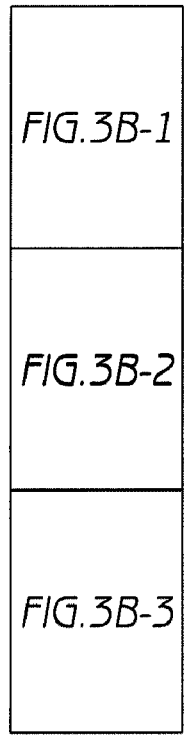

FIG. 3B

CMV/R Ebola GP(Z)(full length E to D)/h
CMV Enhancer/Promoter
Kan.
HTLV-1 R Region
CMV IE Splicing Acceptor
EcoRV(1352)
VRC 6616
6424 bp
E to D
XbaI(2097)
GP(Z)(full length)/h/
BamHI(2693)
Tbgh
BgdI(3406)
EcoRI(3400)
TM
I>V

VRC 6616 (SEQ ID NO: 4)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca cgaccccccg cccattgacg tcaataatga cgtatgttcc
 481 catagtaacg ccaataggga ctttccattg acgtcaatgg gtggagtatt tacggtaaac
 541 tgcccacttg gcagtacatc aagtgtatca tatgccaagt acgcccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt ttgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tcccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt cctttccatg
1321 ggtcttttct gcagtcaccg tcgtcgacga tatcgccgcc atgggcgtga ccggcatcct
1381 gcagctgccc agggacaggt tcaagaggac cagcttcttc ctgtgggtga tcatcctgtt
1441 ccagaggacc ttcagcatcc cctgggcgt gatccacaac agcaccctgc aggtgagcga
1501 cgtggacaag ctggtgtgca gggacaagct gagcagcacc aaccagctga ggagcgtggg
1561 cctgaacctg gacggcaacg gcgtggccac cgacgtgccc agcgccacca gaggtggggg
1621 cttcaggagc ggcgtgcctc ccaaggtggt gaactacgag gccggcgagt gggccgagaa
1681 ctgctacaac ctggagatca agaagcccga cggcagcgag tgcctgcccg ccgcccctga
1741 cggcatcagg ggcttcccca ggtgcaggta cgtgcacaag gtgagcggca ccggcccctg
1801 cgccggcgac ttcgccttcc acaaggaggg cgccttcttc ctgtacgaca ggctggccag
1861 caccgtgatc tacaggggca ccaccttcgc cgagggcgtg gtggccttcc tgatcctgcc
1921 ccaggccaag aaggacttct tcagcagcca ccctctgagg gagcccgtga cgccaccga
1981 ggaccccagc agcggctact acagcaccac catcaggtac caggccaccg cttcggcac
2041 caacgagacc gagtacctgt tcgaggtgga caacctgacc tacgtgcagc tggagtctag
2101 attcacccct cagttcctgc tgcagctgaa cgagaccatc tacaccagcg gcaagaggag
2161 caacaccacc ggcaagctga tctggaaggt gaaccccgag atcgacacca ccatcggcga
2221 gtgggccttc tgggagacca agaagaacct gaccaggaag atcaggagcg aggagctgag
2281 cttcaccgtc gtgagcaacg ggccaagaa catcagcggc cagagccccg ccaggaccag
2341 cagcgacccc ggcaccaaca ccaccaccga ggaccacaag atcatggcca gcgagaacag
2401 cagcgccatg gtgcaggtgc acagccaggg cagggaggcc gccgtgagcc acctgaccac
2461 cctggccacc atcagcacca gccctcagtc tttaaccacc aagcccggcc ccgacaacag
2521 cacccacaac accctgtgt acaagctgga catcagcgag gccacccagg tggagcagca
2581 ccacaggagg accgacaacg acagcaccgc cagcgacacc cttccgcca ccaccgccgc
2641 cggccctccg aaggccgaga acaccaacac cagcaagagc accgactttc tggatcccgc
2701 caccaccacc agccctcaga ccacagcga ccgccggc aacaacaaca cccaccacca
2761 ggacaccggc gaggagagcg ccagcagcgg caagctgggc ctgatcacca acatcgc
2821 cggcgtggcc ggcctgatca ccggcggcag gaggaccagg agggaggcca tcgtgaacgc
2881 ccagcccaag tgcaaccca acctgcacta ctggaccacc aggacgagg gcgccgccat
2941 cggcctggcc tggattccct acttcggccc cgccgccgag ggcatctaca tcgagggcct
```

FIG. 4B-2

```
3001 gatgcacaac caggacggcc tgatctgcgg cctgaggcag ctggccaacg agaccaccca
3061 ggccctgcag ctgttcctga gggccaccac cgagctgagg accttcagca tcctgaacag
3121 gaaggccatc gacttcctgc tgcagaggtg gggcggcacc tgccacatcc tgggccccga
3181 ctgctgcatc gagccccacg actggaccaa gaacatcacc gacaagatcg accagatcat
3241 ccacgacttc gtggacaaga ccctgccaga ccagggcgac aacgacaact ggtggaccgg
3301 ctggcggcag tggatacctg ccggcatcgg cgtgaccggc gtggtgatcg ccgtgatcgc
3361 tctgttctgc atctgcaagt tcgtgttctg aacacgtgga attcagatct gctgtgcctt
3421 ctagttgcca gccatctgtt gtttgccct ccccgtgcc ttccttgacc ctggaaggtg
3481 ccactcccac tgtcctttcc taataaaatg aggaaattgc atcgcattgt ctgagtaggt
3541 gtcattctat tctgggggt ggggtggggc aggacagcaa gggggaggat tgggaagaca
3601 atagcaggca tgctggggat gcggtgggct ctatgggtac ccaggtgctg aagaattgac
3661 ccggttcctc ctgggccaga aagaagcagg cacatcccct tctctgtgac acaccctgtc
3721 cacgccctg gttcttagtt ccagccccac tcataggaca ctcatagctc aggagggctc
3781 cgccttcaat cccacccgct aaagtacttg gagcggtctc tccctccctc atcagcccac
3841 caaaccaaac ctagcctcca agagtgggaa gaaattaaag caagataggc tattaagtgc
3901 agagggagag aaaatgcctc caacatgtga ggaagtaatg agagaaatca tagaattta
3961 aggccatgat ttaaggccat catggcctta atcttccgct tcctcgctca ctgactcgct
4021 gcgctcggtc gttcggctgc ggcgagcggt atcagctcac tcaaaggcgg taatacggtt
4081 atccacagaa tcaggggata acgcaggaaa gaacatgtga gcaaaaggcc agcaaaaggc
4141 caggaaccgt aaaaaggccg cgttgctggc gtttttccat aggctccgcc ccctgacga
4201 gcatcacaaa aatcgacgct caagtcagag gtggcgaaac ccgacaggac tataaagata
4261 ccaggcgttt ccccctggaa gctccctcgt gcgctctcct gttccgaccc tgccgcttac
4321 cggatacctg tccgcctttc tcccttcggg aagcgtggcg ctttctcata gctcacgctg
4381 taggtatctc agttcggtgt aggtcgttcg ctccaagctg ggctgtgtgc acgaaccccc
4441 cgttcagccc gaccgctgcg ccttatccgg taactatcgt cttgagtcca acccggtaag
4501 acacgactta tcgccactgg cagcagccac tggtaacagg attagcagag cgaggtatgt
4561 aggcggtgct acagagttct tgaagtggtg gcctaactac ggctacacta gaagaacagt
4621 atttggtatc tgcgctctgc tgaagccagt taccttcgga aaaagagttg gtagctcttg
4681 atccggcaaa caaaccaccg ctggtagcgg tggttttttt gtttgcaagc agcagattac
4741 gcgcagaaaa aaaggatctc aagaagatcc tttgatcttt tctacggggt ctgacgctca
4801 gtggaacgaa aactcacgtt aagggatttt ggtcatgaga ttatcaaaaa ggatcttcac
4861 ctagatcctt ttaaattaaa aatgaagttt taaatcaatc taaagtatat atgagtaaac
4921 ttggtctgac agttaccaat gcttaatcag tgaggcacct atctcagcga tctgtctatt
4981 tcgttcatcc atagttgcct gactcggggg ggggggcgc tgaggtctgc ctcgtgaaga
5041 aggtgttgct gactcatacc aggcctgaat cgccccatca tccagccaga aagtgaggga
5101 gccacggttg atgagagctt tgttgtaggt ggaccagttg gtgattttga acttttgctt
5161 tgccacggaa cggtctgcgt tgtcgggaag atgcgtgatc tgatccttca actcagcaaa
5221 agttcgattt attcaacaaa gccgccgtcc cgtcaagtca gcgtaatgct ctgccagtgt
5281 tacaaccaat taaccaattc tgattagaaa aactcatcga gcatcaaatg aaactgcaat
5341 ttattcatat caggattatc aataccatat ttttgaaaaa gccgtttctg taatgaagga
5401 gaaaactcac cgaggcagtt ccataggatg caagatcct ggtatcggtc tgcgattccg
5461 actcgtccaa catcaataca acctattaat ttcccctcgt caaaaataag gttatcaagt
5521 gagaaatcac catgagtgac gactgaatcc ggtgagaatg gcaaaagctt atgcatttct
5581 ttccagactt gttcaacagg ccagccatta gctcgtcat caaaatcact cgcatcaacc
5641 aaaccgttat tcattcgtga ttgcgcctga gcgagacgaa atacgcgatc gctgttaaaa
5701 ggacaattac aaacaggaat cgaatgcaac cggcgcagga acactgccag cgcatcaaca
5761 atatttcac ctgaatcagg atattcttct aatacctgga atgctgttt ccggggatc
5821 gcagtggtga gtaaccatgc atcatcagga gtacggataa aatgcttgat ggtcggaaga
5881 ggcataaatt ccgtcagcca gtttagtctg accatctcat ctgtaacatc attggcaacg
5941 ctacctttgc catgtttcag aaacaactct ggcgcatcgg gcttcccata caatcgatag
6001 attgtcgcac ctgattgccc gacattatcg cgagcccatt tatacccata taaatcagca
```

FIG. 4B-3

```
6061 tccatgttgg aatttaatcg cggcctcgag caagacgttt cccgttgaat atggctcata
6121 acaccccttg tattactgtt tatgtaagca gacagtttta ttgttcatga tgatatattt
6181 ttatcttgtg caatgtaaca tcagagattt tgagacacaa cgtggctttc cccccccccc
6241 cattattgaa gcatttatca gggttattgt ctcatgagcg gatacatatt tgaatgtatt
6301 tagaaaaata aacaaatagg ggttccgcgc acatttcccc gaaaagtgcc acctgacgtc
6361 taagaaacca ttattatcat gacattaacc tataaaaata ggcgtatcac gaggcccttt
6421 cgtc
```

FIG. 4B

| FIG. 4B-1 |
| FIG. 4B-2 |
| FIG. 4B-3 |

FIG. 5B-1

VRC 6712 (SEQ ID NO: 5)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca acgaccccg cccattgacg tcaataatga cgtatgttcc
 481 catagtaacg ccaataggga ctttccattg acgtcaatgg gtggagtatt tacggtaaac
 541 tgcccacttg gcagtacatc aagtgtatca tatgccaagt acgccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt ttgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt cctttccatg
1321 ggtcttttct gcagtcaccg tcgtcgacac gtgtgatcag atatcgcggc cgctctagag
1381 atatcgccgc catgaagacc acctgcctgc tgatcagcct gatcctgatc cagggcgtga
1441 agaccctgcc catcctggag atcgccagca acatccagcc ccagaacgtg gacagcgtgt
1501 gcagcggcac cctgcagaag accgaggacg tgcacctgat gggcttcacc ctgagcggcc
1561 agaaggtggc cgacagccct ctggaggcca gcaagaggtg ggccttcagg gccggcgtgc
1621 cccccaagaa cgtggagtac accgagggcg aggaggccaa gacctgctac aacatcagcg
1681 tgaccgaccc cagcggcaag agcctgctgc tggaccctcc caccaacatc agggactacc
1741 ctaagtgcaa gaccatccac cacatccagg ccagaaaccc tcacgcccag ggcatcgccc
1801 tgcacctgtg gggcgccttc ttcctgtacg acaggatcgc cagcaccacc atgtacagag
1861 gaaaagtgtt cacagaggga aacatcgctg ctatgatcgt gaacaagacc gtgcataaga
1921 tgatcttcag cagacagggga cagggatata gacatatgaa cctgacatcc acaaacaagt
1981 actggacaag cagcaacgga acacagacaa acgatacagg atgttttgga acactgcagg
2041 aatacaactc caccaagaac cagacatgtg cccctagcaa gaagcctctg cctctgccta
2101 cagctcatcc tgaagtgaag ctgacatcca agcacagat gccacaaag ctgaacacaa
2161 cagatcctaa tagcgacgac gaggatctga caacaagcgg atccggatcc ggagaacagg
2221 aaccttatac aacaagcgac gctgctacaa acagggact gtcctccaca atgcctccta
2281 cacctagccc tcagcctagc acacctcagc agggaggcaa caacacaaac cattcccagg
2341 gagtggtgac agaacctgga aagacaaaca caacagccca gcctagcatg cctcctcata
2401 acacaacaac aatcagcaca aacaacacct caagcacaa tctgagcaca cctagcgtgc
2461 ctattcagaa tgccaccaac tacaacacac agtccacagc ccctgaaaac gaacagacct
2521 ccgccccttc caaaacaacc ctgctgccta cagaaaaccc tacaacagcc aagagcacaa
2581 acagcacaaa gagcccaca caacagtgc ctaacacaac aaacaagtat agcacaagcc
2641 ctagccctac acctaattcc acagctcagc atctggtgta ttttagaaga aagagaaaca
2701 tcctgtggag agaaggagat atgttccctt ttctggatgg actgatcaac gctcctatcg
2761 attttgatcc tgtgcctaac acaaagacaa tcttgatga agcagcagc agcggagcct
2821 ccgccgaaga agatcagcat gcctccccta acatcagcct gacactgagc tattttccta
2881 aggtgaacga aaacacagcc cattccggag aaaacgaaaa cgattgtgat gccgaactga
2941 gaatctggag cgtgcaggaa gatgatctgg ccgccggact gagctggatc ccttttttg
```

FIG. 5B-2

```
3001 ggcccggaat tgaaggactg tacaccgccg gcctgatcaa gaaccagaac aacctggtgt
3061 gcaggctgag gaggctggcc aaccagaccg ccaagagcct ggagctgctg ctgagggtga
3121 ccaccgagga gaggaccttc agcctgatca acaggcacgc catcgacttc ctgctggcta
3181 ggtggggcgg cacctgcaag gtgctgggcc ccgactgctg catcggcatc gaggacctga
3241 gcaggaacat cagcgagcag atcgaccaga tcaagaagga cgagcagaag gagggcaccg
3301 gctggggcct gggcggcaag tggtggacca gcgactgggg agtgctgaca aacctgggaa
3361 tcctgctgct gctgagcatt gccgtgctca ttgctctgtc ctgtatctgt agaatcttta
3421 ccaagtacat cggatgatag atctgctgtg ccttctagtt gccagccatc tgttgtttgc
3481 ccctccccg tgccttcctt gaccctggaa ggtgccactc ccactgtcct ttcctaataa
3541 aatgaggaaa ttgcatcgca ttgtctgagt aggtgtcatt ctattctggg gggtggggtg
3601 gggcaggaca gcaaggggga ggattgggaa gacaatagca ggcatgctgg ggatgcggtg
3661 ggctctatgg gtacccaggt gctgaagaat tgacccggtt cctcctgggc cagaaagaag
3721 caggcacatc cccttctctg tgacacaccc tgtccacgcc cctggttctt agttccagcc
3781 ccactcatag gacactcata gctcaggagg gctccgcctt caatcccacc cgctaaagta
3841 cttggagcgg tctctccctc cctcatcagc ccaccaaacc aaacctagcc tccaagagtg
3901 ggaagaaatt aaagcaagat aggctattaa gtgcagaggg agagaaaatg cctccaacat
3961 gtgaggaagt aatgagagaa atcatagaat tttaaggcca tgatttaagg ccatcatggc
4021 cttaatcttc cgcttcctcg ctcactgact cgctgcgctc ggtcgttcgg ctgcggcgag
4081 cggtatcagc tcactcaaag gcggtaatac ggttatccac agaatcaggg gataacgcag
4141 gaaagaacat gtgagcaaaa ggccagcaaa aggccaggaa ccgtaaaaag gccgcgttgc
4201 tggcgttttt ccataggctc cgcccccctg acgagcatca caaaaatcga cgctcaagtc
4261 agaggtggcg aaacccgaca ggactataaa gataccaggc gtttccccct ggaagctccc
4321 tcgtgcgctc tcctgttccg accctgccgc ttaccggata cctgtccgcc tttctccctt
4381 cgggaagcgt ggcgctttct catagctcac gctgtaggta tctcagttcg gtgtaggtcg
4441 ttcgctccaa gctgggctgt gtgcacgaac cccccgttca gcccgaccgc tgcgccttat
4501 ccggtaacta tcgtcttgag tccaacccgg taagacacga cttatcgcca ctggcagcag
4561 ccactggtaa caggattagc agagcgaggt atgtaggcgg tgctacagag ttcttgaagt
4621 ggtggcctaa ctacggctac actagaagaa cagtatttgg tatctgcgct ctgctgaagc
4681 cagttacctt cggaaaaaga gttggtagct cttgatccgg caaacaaacc accgctggta
4741 gcggtggttt ttttgtttgc aagcagcaga ttacgcgcag aaaaaaagga tctcaagaag
4801 atcctttgat cttttctacg gggtctgacg ctcagtggaa cgaaaactca cgttaaggga
4861 ttttggtcat gagattatca aaaaggatct tcacctagat ccttttaaat taaaaatgaa
4921 gttttaaatc aatctaaagt atatatgagt aaacttggtc tgacagttac caatgcttaa
4981 tcagtgaggc acctatctca gcgatctgtc tatttcgttc atccatagtt gcctgactcg
5041 ggggggggg gcgctgaggt ctgcctcgtg aagaaggtgt tgctgactca taccaggcct
5101 gaatcgcccc atcatccagc cagaaagtga gggagccacg gttgatgaga gctttgttgt
5161 aggtggacca gttggtgatt ttgaactttt gctttgccac ggaacggtct gcgttgtcgg
5221 gaagatgcgt gatctgatcc ttcaactcag caaaagttcg atttattcaa caaagccgcc
5281 gtcccgtcaa gtcagcgtaa tgctctgcca gtgttacaac caattaacca attctgatta
5341 gaaaaactca tcgagcatca aatgaaactg caatttattc atatcaggat tatcaatacc
5401 atatttttga aaaagccgtt tctgtaatga aggagaaaac tcaccgaggc agttccatag
5461 gatggcaaga tcctggtatc ggtctgcgat tccgactcgt ccaacatcaa tacaacctat
5521 taatttcccc tcgtcaaaaa taaggttatc aagtgagaaa tcaccatgag tgacgactga
5581 atccggtgag aatggcaaaa gcttatgcat ttctttccag acttgttcaa caggccagcc
5641 attacgctcg tcatcaaaat cactcgcatc aaccaaaccg ttattcattc gtgattgcgc
5701 ctgagcgaga cgaaatacgc gatcgctgtt aaaaggacaa ttacaaacag gaatcgaatg
5761 caaccggcgc aggaacactg ccagcgcatc aacaatattt tcacctgaat caggatattc
5821 ttctaatacc tggaatgctg ttttcccggg gatcgcagtg gtgagtaacc atgcatcatc
5881 aggagtacgg ataaaatgct tgatggtcgg aagaggcata aattccgtca gccagtttag
5941 tctgaccatc tcatctgtaa catcattggc aacgctacct ttgccatgtt tcagaaacaa
6001 ctctggcgca tcgggcttcc catacaatcg atagattgtc gcacctgatt gcccgacatt
```

FIG. 5B-3

```
6061 atcgcgagcc catttatacc catataaatc agcatccatg ttggaattta atcgcggcct
6121 cgagcaagac gtttcccgtt gaatatggct cataacaccc cttgtattac tgtttatgta
6181 agcagacagt tttattgttc atgatgatat atttttatct tgtgcaatgt aacatcagag
6241 attttgagac acaacgtggc tttcccccccc cccccattat tgaagcattt atcagggtta
6301 ttgtctcatg agcggataca tatttgaatg tatttagaaa aataaacaaa tagggggttcc
6361 gcgcacattt ccccgaaaag tgccacctga cgtctaagaa accattatta tcatgacatt
6421 aacctataaa aataggcgta tcacgaggcc ctttcgtc
```

FIG. 5B

| FIG.5B-1 |
| FIG.5B-2 |
| FIG.5B-3 |

FIG. 6B-1

VRC 6713 (SEQ ID NO: 6)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcagattgg
 241 ctattggcca ttgcatacgt tgtatccata tcataatatg tacatttata ttggctcatg
 301 tccaacatta ccgccatgtt gacattgatt attgactagt tattaatagt aatcaattac
 361 ggggtcatta gttcatagcc catatatgga gttccgcgtt acataactta cggtaaatgg
 421 cccgcctggc tgaccgccca acgaccccg cccattgacg tcaataatga cgtatgttcc
 481 catagtaacg ccaatagga ctttccattg acgtcaatgg gtggagtatt tacggtaaac
 541 tgcccacttg gcagtacatc aagtgtatca tatgccaagt acgccccta ttgacgtcaa
 601 tgacggtaaa tggcccgcct ggcattatgc ccagtacatg accttatggg actttcctac
 661 ttggcagtac atctacgtat tagtcatcgc tattaccatg gtgatgcggt tttggcagta
 721 catcaatggg cgtggatagc ggtttgactc acggggattt ccaagtctcc accccattga
 781 cgtcaatggg agtttgtttt ggcaccaaaa tcaacgggac tttccaaaat gtcgtaacaa
 841 ctccgcccca ttgacgcaaa tgggcggtag gcgtgtacgg tgggaggtct atataagcag
 901 agctcgttta gtgaaccgtc agatcgcctg gagacgccat ccacgctgtt ttgacctcca
 961 tagaagacac cgggaccgat ccagcctcca tcggctcgca tctctccttc acgcgcccgc
1021 cgccctacct gaggccgcca tccacgccgg ttgagtcgcg ttctgccgcc tcccgcctgt
1081 ggtgcctcct gaactgcgtc cgccgtctag gtaagtttaa agctcaggtc gagaccgggc
1141 ctttgtccgg cgctcccttg gagcctacct agactcagcc ggctctccac gctttgcctg
1201 accctgcttg ctcaactcta gttaacggtg gagggcagtg tagtctgagc agtactcgtt
1261 gctgccgcgc gcgccaccag acataatagc tgacagacta acagactgtt ccttccatg
1321 ggtcttttct gcagtcaccg tcgtcgacac gtgtgatcag atatcgcggc cgctctagag
1381 atatcgccgc catgaagacc acctgcctgc tgatcagcct gatcctgatc cagggcgtga
1441 agaccctgcc catcctggag atcgccagca acatccagcc ccagaacgtg gacagcgtgt
1501 gcagcggcac cctgcagaag accgaggacg tgcacctgat gggcttcacc ctgagcggcc
1561 agaaggtggc cgacagccct ctggaggcca gcaagaggtg ggccttcagg gccggcgtgc
1621 ccccaagaa cgtggagtac accgaggccg aggaggccaa gacctgctac aacatcagcg
1681 tgaccgaccc cagcggcaag agcctgctgc tggaccctcc caccaacatc agggactacc
1741 ctaagtgcaa gaccatccac cacatccagg ccagaaccc tcacgcccag ggcatcgccc
1801 tgcacctgtg gggcgccttc ttcctgtacg acaggatcgc cagcaccacc atgtacagag
1861 gaaaagtgtt cacagaggga aacatcgctg ctatgatcgt gaacaagacc gtgcataaga
1921 tgatcttcag cagacaggga cagggatata gacatatgaa cctgacatcc acaaacaagt
1981 actggacaag cagcaacgga acacagacaa acgatacagg atgttttgga acactgcagg
2041 aatacaactc caccaagaac cagacatgtg ccctagcaa gaagcctctg cctctgccta
2101 cagctcatcc tgaagtgaag ctgacatcca caagcacaga tgccacaaag ctgaacacaa
2161 cagatcctaa tagcgacgac gaggatctga caacaagcgg atccggagaa cagg
2221 aaccttatac aacaagcgac gctgctacaa acagggact gtcctccaca atgcctccta
2281 cacctagccc tcagcctagc acacctcagc agggaggcaa caacacaaac cattcccagg
2341 gagtggtgac agaacctgga aagacaaaca caacagccca gcctagcatg cctcctcata
2401 acacaacaac aatcagcaca aacaacacct ccaagcacaa tctgagcaca cctagcgtgc
2461 ctattcagaa tgccaccaac tacaacacac agtccacagc ccctgaaaac gaacagacct
2521 ccgcccctcc caaaacaacc ctgctgccta cagaaaaccc tacaacagcc aagagcacaa
2581 acagcacaaa gagcccctaca caacagtgc ctaacacaac aaacaagtat agcacaagcc
2641 ctagccctac acctaattcc acagctcagc atcggtgta ttttagaaga aagagaaaca
2701 tcctgtggag agaaggagat atgttccctt ttctggatgg actgatcaac gctcctatcg
2761 attttgatcc tgtgcctaac acaaagacaa tctttgatga aagcagcagc agcggagcct
2821 ccgccgaaga agatcagcat gcctccccta acatcagcct gacactgagc tatttcctaa
2881 aggtgaacga aaacacagcc cattccggag aaaacgaaaa cgattgtgat gccgaactga
```

FIG. 6B-2

```
2941 gaatctggag cgtgcaggaa gatgatctgg ccgccggact gagctggatc ccttttttg
3001 ggcccggaat tgaaggactg tacaccgccg gcctgatcaa gaaccagaac aacctggtgt
3061 gcaggctgag gaggctggcc aaccagaccg ccaagagcct ggagctgctg ctgagggtga
3121 ccaccgagga gaggaccttc agcctgatca acaggcacgc catcgacttc ctgctggcta
3181 ggtggggcgg cacctgcaag gtgctgggcc ccgactgctg catcggcatc gaggacctga
3241 gcaggaacat cagcgagcag atcgaccaga tcaagaagga cgagcagaag gagggcaccg
3301 gctggggcct gggcggcaag tggtggacca gcgactgggg agtgctgaca aacctgggaa
3361 tcctgctgct gctgagcatt gccgtgctca ttgctctgtc ctgtatctgt agaatcttta
3421 ccaagtacat cggatgatag atctgctgtg ccttctagtt gccagccatc tgttgtttgc
3481 ccctcccccg tgccttcctt gaccctggaa ggtgccactc ccactgtcct ttcctaataa
3541 aatgaggaaa ttgcatcgca ttgtctgagt aggtgtcatt ctattctggg gggtggggtg
3601 gggcaggaca gcaaggggga ggattgggaa gacaatagca ggcatgctgg ggatgcggtg
3661 ggctctatgg gtacccaggt gctgaagaat tgacccggtt cctcctgggc cagaaagaag
3721 caggcacatc cccttctctg tgacacaccc tgtccacgcc cctggttctt agttccagcc
3781 ccactcatag gacactcata gctcaggagg gctccgcctt caatcccacc cgctaaagta
3841 cttggagcgg tctctccctc cctcatcagc ccaccaaacc aaacctagcc tccaagagtg
3901 ggaagaaatt aaagcaagat aggctattaa gtgcagaggg agagaaaatg cctccaacat
3961 gtgaggaagt aatgagagaa atcatagaat tttaaggcca tgatttaagg ccatcatggc
4021 cttaatcttc cgcttcctcg ctcactgact cgctgcgctc ggtcgttcgg ctgcggcgag
4081 cggtatcagc tcactcaaag gcggtaatac ggttatccac agaatcaggg gataacgcag
4141 gaaagaacat gtgagcaaaa ggccagcaaa aggccaggaa ccgtaaaaag gccgcgttgc
4201 tggcgttttt ccataggctc cgcccccctg acgagcatca caaaaatcga cgctcaagtc
4261 agaggtggcg aaacccgaca ggactataaa gataccaggc gtttccccct ggaagctccc
4321 tcgtgcgctc tcctgttccg accctgccgc ttaccggata cctgtccgcc tttctccctt
4381 cgggaagcgt ggcgctttct catagctcac gctgtaggta tctcagttcg gtgtaggtcg
4441 ttcgctccaa gctgggctgt gtgcacgaac cccccgttca gcccgaccgc tgcgccttat
4501 ccggtaacta tcgtcttgag tccaacccgg taagacacga cttatcgcca ctggcagcag
4561 ccactggtaa caggattagc agagcgaggt atgtaggcgg tgctacagag ttcttgaagt
4621 ggtggcctaa ctacggctac actagaagaa cagtatttgg tatctgcgct ctgctgaagc
4681 cagttacctt cggaaaaaga gttggtagct cttgatccgg caaacaaacc accgctggta
4741 gcggtggttt ttttgtttgc aagcagcaga ttacgcgcag aaaaaaagga tctcaagaag
4801 atcctttgat cttttctacg gggtctgacg ctcagtggaa cgaaaactca cgttaaggga
4861 ttttggtcat gagattatca aaaaggatct tcacctagat ccttttaaat taaaaatgaa
4921 gttttaaatc aatctaaagt atatatgagt aaacttggtc tgacagttac caatgcttaa
4981 tcagtgaggc acctatctca gcgatctgtc tatttcgttc atccatagtt gcctgactcg
5041 ggggggggggg gcgctgaggt ctgcctcgtg aagaaggtgt tgctgactca taccaggcct
5101 gaatcgcccc atcatccagc cagaaagtga gggagccacg gttgatgaga gctttgtttgt
5161 aggtggacca gttggtgatt ttgaacttt gctttgccac ggaacggtct gcgttgtcgg
5221 gaagatgcgt gatctgatcc ttcaactcag caaaagttcg atttattcaa caaagccgcc
5281 gtcccgtcaa gtcagcgtaa tgctctgcca gtgttacaac caattaacca attctgatta
5341 gaaaaactca tcgagcatca aatgaaactg caatttattc atatcaggat tatcaatacc
5401 atatttttga aaaagccgtt tctgtaatga aggagaaaac tcaccgaggc agttccatag
5461 gatggcaaga tcctggtatc ggtctgcgat tccgactcgt ccaacatcaa tacaacctat
5521 taatttcccc tcgtcaaaaa taaggttatc aagtgagaaa tcaccatgag tgacgactga
5581 atccggtgag aatggcaaaa gcttatgcat ttctttccag acttgttcaa caggccagcc
5641 attacgctcg tcatcaaaat cactcgcatc aaccaaaccg ttattcattc gtgattgcgc
5701 ctgagcgaga cgaaatacgc gatcgctgtt aaaaggacaa ttacaaacag gaatcgaatg
5761 caaccggcgc aggaacactg ccagcgcatc aacaatattt tcacctgaat caggatattc
5821 ttctaatacc tggaatgctg ttttcccggg gatcgcagtg gtgagtaacc atgcatcatc
5881 aggagtacgg ataaaatgct tgatggtcgg aagaggcata aattccgtca gccagtttag
5941 tctgaccatc tcatctgtaa catcattggc aacgctacct ttgccatgtt tcagaaacaa
```

FIG. 6B-3

6001 ctctggcgca tcgggcttcc catacaatcg atagattgtc gcacctgatt gcccgacatt
6061 atcgcgagcc catttatacc catataaatc agcatccatg ttggaattta atcgcggcct
6121 cgagcaagac gtttcccgtt gaatatggct cataacaccc cttgtattac tgtttatgta
6181 agcagacagt tttattgttc atgatgatat atttttatct tgtgcaatgt aacatcagag
6241 attttgagac acaacgtggc tttccccccc cccccattat tgaagcattt atcagggtta
6301 ttgtctcatg agcggataca tatttgaatg tatttagaaa aataaacaaa tagggggttcc
6361 gcgcacattt ccccgaaaag tgccacctga cgtctaagaa accattatta tcatgacatt
6421 aacctataaa aataggcgta tcacgaggcc ctttcgtc

FIG. 6B

| FIG.6B-1 |
| FIG.6B-2 |
| FIG.6B-3 |

FIG. 7B-1 pAdApt.Ebo.GP.Fl.(Z).E71D (SEQ ID NO: 7)

ttaattaaccgcaattctcatgtttgacagcttatcatcatcaataatataccttattttggattgaagccaa
tatgataatgagggggtggagtttgtgacgtggcgcggggcgtgggaacggggcgggtgacgtagtagtgtgg
cggaagtgtgatgttgcaagtgtggcggaacacatgtaagcgacggatgtggcaaaagtgacgtttttggtgt
gcgccggtgtacacaggaagtgacaattttcgcgcggttttaggcggatgttgtagtaaatttgggcgtaacc
gagtaagatttggccattttcgcgggaaaactgaataagaggaagtgaaatctgaataattttgtgttactca
tagcgcgtaatatttgtctagggccgcggggactttgaccgtttacgtggagactcgcccaggtgtttttctc
aggtgttttccgcgttccgggtcaaagttggcgttttattattatagtcagtacgtaccagtgcactggccta
ggtggtcaatattggccattagccatattattcattggttatatagcataaatcaatattggctattggccat
tgcatacgttgtatccatatcataatatgtacatttatattggctcatgtccaacattaccgccatgttgaca
ttgattattgactagttattaatagtaatcaattacggggtcattagttcatagcccatatatggagttccgc
gttacataacttacggtaaatggcccgcctggctgaccgcccaacgacccccgcccattgacgtcaataatga
cgtatgttcccatagtaacgccaatagggactttccattgacgtcaatgggtggagtatttacggtaaactgc
ccacttggcagtacatcaagtgtatcatatgccaagtacgccccctattgacgtcaatgacggtaaatggccc
gcctggcattatgcccagtacatgaccttatgggactttcctacttggcagtacatctacgtattagtcatcg
ctattaccatggtgatgcggttttggcagtacatcaatgggcgtggatagcggtttgactcacggggatttcc
aagtctccaccccattgacgtcaatgggagtttgttttggcaccaaaatcaacgggactttccaaaatgtcgt
aacaactccgccccattgacgcaaatgggcggtaggcgtgtacggtgggaggtctatataagcagagctcgtt
tagtgaaccgtcagatcgcctggagacgccatccacgctgttttgacctccatagaagacaccgggaccgatc
cagcctccgcggccgggaacggtgcattggaagcttgccgcc ATGGGCGTTACAGGAATATTGCAGTTACCTCGTGATCGATTCAAGAGGACATCATTCTTTCTTTGGGTAATTA
TCCTTTTCCAAAGAACATTTTCCATCCCACTTGGAGTCATCCACAATAGCACATTACAGGTTAGTGATGTCGA
CAAACTAGTTTGTCGTGACAAACTGTCATCCACAAATCAATTGAGATCAGTTGGACTGAATCTCGATGGCAAT
GGAGTGGCAACTGACGTGCCATCTGCAACTAAAAGATGGGGCTTCAGGTCCGGTGTCCCACCAAAGGTGGTCA
ATTATGAAGCTGGTGAATGGGCTGAAAACTGCTACAATCTTGAAATCAAAAAACCTGACGGGAGTGAGTGTCT
ACCAGCAGCGCCAGACGGGATTCGGGGCTTCCCCCGGTGCCGGTATGTGCACAAAGTATCAGGAACGGGACCG
TGTGCCGGAGACTTTGCCTTCCATAAAGAGGGTGCTTTCTTCCTGTATGATCGACTTGCTTCCACAGTTATCT
ACCGAGGAACGACTTTCGCTGAAGGTGTCGTTGCATTTCTGATACTGCCCCAAGCTAAGAAGGACTTCTTCAG
CTCACACCCCTTGAGAGAGCCGGTCAATGCAACGGAGGACCCGTCTAGTGGCTACTATTCTACCACAATTAGA
TATCAGGCTACCGGTTTTGGAACCAATGAGACAGAGTACTTGTTCGAGGTTGACAATTTGACCTACGTCCAAC
TTGAATCAAGATTCACACCACAGTTTCTGCTCCAGCTGAATGAGACAATATATACAAGTGGGAAAAGGAGCAA
TACCACGGGAAAACTAATTTGGAAGGTCAACCCCGAAATTGATACAACAATCGGGGAGTGGGCCTTCTGGGAA
ACTAAAAAAAACCTCACTAGAAAAATTCGCAGTGAAGAGTTGTCTTTCACAGTTGTATCAAACGGAGCCAAAA
ACATCAGTGGTCAGAGTCCGGCGCGAACTTCTTCCGACCCAGGGACCAACACAACAACTGAAGACCACAAAAT
CATGGCTTCAGAAAATTCCTCTGCAATGGTTCAAGTGCACAGTCAAGGAAGGGAAGCTGCAGTGTCGCATCTA
ACAACCCTTGCCACAATCTCCACGAGTCCCCAATCCCTCACAACCAAACCAGGTCCGGACAACAGCACCCATA
ATACACCCGTGTATAAACTTGACATCTCTGAGGCAACTCAAGTTGAACAACATCACCGCAGAACAGACAACGA
CAGCACAGCCTCCGACACTCCCTCTGCCACGACCGCAGCCGGACCCCCAAAAGCAGAGAACACCAACACGAGC
AAGAGCACTGACTTCCTGGACCCCGCCACCACAACAAGTCCCCAAAACCACAGCGAGACCGCTGGCAACAACA
ACACTCATCACCAAGATACCGGAGAAGAGAGTGCCAGCAGCGGGAAGCTAGGCTTAATTACCAATACTATTGC
TGGAGTCGCAGGACTGATCACAGGCGGGAGAAGAACTCGAAGAGAAGCAATTGTCAATGCTCAACCCAAATGC
AACCCTAATTTACATTACTGGACTACTCAGGATGAAGGTGCTGCAATCGGACTGGCCTGGATACCATATTTCG
GGCCAGCAGCCGAGGGAATTTACATAGAGGGGCTAATGCACAATCAAGATGGTTTAATCTGTGGGTTGAGACA
GCTGGCCAACGAGACGACTCAAGCTCTTCAACTGTTCCTGAGAGCCACAACTGAGCTACGCACCTTTTCAATC
CTCAACCGTAAGGCAATTGATTTCTTGCTGCAGCGATGGGGCGGCACATGCCACATTCTGGGACCGGACTGCT
GTATCGAACCACATGATTGGACCAAGAACATAACAGACAAAATTGATCAGATTATTCATGATTTTGTTGATAA
AACCCTTCCGGACCAGGGGGACAATGACAATTGGTGGACAGGATGGAGACAATGGATACCGGCAGGTATTGGA
GTTACAGGCGTTGTAATTGCAGTTATCGCTTTATTCTGTATATGCAAATTTGTCTTT
tagtaatctagacgagatccgaacttgtttattgcagcttataatggttacaaataaagcaatagcatcacaa
atttcacaaataaagcatttttttcactgcattctagttgtggtttgtccaaactcatcaatgtatcttatca
tgtctagatctgtactgaaatgtgtgggcgtggcttaagggtgggaaagaatatataaggtgggggtcttatg
tagttttgtatctgttttgcagcagccgccgccgccatgagcaccaactcgtttgatggaagcattgtgagct
catatttgacaacgcgcatgcccccatgggccggggtgcgtcagaatgtgatgggctccagcattgatggtcg
ccccgtcctgcccgcaaactctactaccttgacctacgagaccgtgtctggaacgccgttggagactgcagcc
tccgccgccgcttcagccgctgcagccaccgcccgcgggattgtgactgactttgctttcctgagcccgcttg
caagcagtgcagcttcccgttcatccgcccgcgatgacaagttgacggctcttttggcacaattggattcttt
gacccgggaacttaatgtcgtttctcagcagctgttggatctgcgccagcaggtttctgccctgaaggcttcc
tcccctcccaatgcggtttaaaacataaataaaaaaccagactctgtttggatttggatcaagcaagtgtctt

FIG. 7B-2

```
gctgtctttatttaggggttttgcgcgcgcggtaggcccgggaccagcggtctcggtcgttgagggtcctgtg
tattttttccaggacgtggtaaaggtgactctggatgttcagatacatgggcataagcccgtctctggggtgg
aggtagcaccactgcagagcttcatgctgcggggtggtgttgtagatgatccagtcgtagcaggagcgctggg
cgtggtgcctaaaaatgtctttcagtagcaagctgattgccaggggcaggcccttggtgtaagtgtttacaaa
gcggttaagctgggatgggtgcatacgtggggatatgagatgcatcttggactgtattttaggttggctatg
ttcccagccatatccctccggggattcatgttgtgcagaaccaccagcacagtgtatccggtgcacttgggaa
atttgtcatgtagcttagaaggaaatgcgtggaagaacttggagacgcccttgtgacctccaagattttccat
gcattcgtccataatgatggcaatgggcccacgggcggcggcctgggcgaagatatttctgggatcactaacg
tcatagttgtgttccaggatgagatcgtcataggccattttacaaagcgcgggcggagggtgccagactgcg
gtataatggttccatccggcccaggggcgtagttaccctcacagatttgcatttcccacgctttgagttcaga
tgggggggatcatgtctacctgcggggcgatgaagaaaacggtttccggggtaggggagatcagctgggaagaa
agcaggttcctgagcagctgcgacttaccgcagccggtgggcccgtaaatcacacctataccggctgcaact
ggtagttaagagagctgcagctgccgtcatccctgagcaggggggccacttcgttaagcatgtccctgactcg
catgttttccctgaccaaatccgccagaaggcgctcgccgcccagcgatagcagttcttgcaaggaagcaaag
ttttttcaacggtttgagaccgtccgccgtaggcatgcttttgagcgtttgaccaagcagttccaggcggtccc
acagctcggtcacctgctctacggcatctcgatccagcatatctcctcgtttcgcgggttggggcggctttcg
ctgtacggcagtagtcggtgctcgtccagacgggccagggtcatgtctttccacgggcgcagggtcctcgtca
gcgtagtctgggtcacggtgaaggggtgcgctccgggctgcgcgctggccagggtgcgcttgaggctggtcct
gctggtgctgaagcgctgccggtcttcgcctgcgcgtcggccaggtagcatttgaccatggtgtcatagtcc
agcccctccgcggcgtggcccttggcgcgcagcttgcccttggaggaggcgccgcacgagggggcagtgcagac
ttttgagggcgtagagcttgggcgcgagaaataccgattccggggagtaggcatccgcgccgcaggccccgca
gacggtctcgcattccacgagccaggtgagctctggccgttcggggtcaaaaaccaggtttcccccatgcttt
ttgatgcgtttcttacctctggttttccatgagccggtgtccacgctcggtgacgaaaaggctgtccgtgtccc
cgtatacagacttgagaggcctgtcctcgagcggtgttccgcggtcctcctcgtatagaaactcggaccactc
tgagacaaaggctcgcgtccaggccagcacgaaggaggctaagtggagggggtagcggtcgttgtccactagg
gggtccactcgctccagggtgtgaagacacatgtcgccctcttcggcatcaaggaaggtgattggtttgtagg
tgtaggccacgtgaccgggtgttcctgaagggggggctataaaaggggggtggggcgcgttcgtcctcactctc
ttccgcatcgctgtctgcgagggccagctgttgggtgagtcgacgcgaggctggatggccttccccattatg
attcttctcgcttccggcggcatcgggatgcccgcgttgcaggccatgctgtccaggcaggtagatgacgacc
atcagggacagcttcaaggccagcaaaaggccaggaaccgtaaaaaggccgcgttgctggcgttttccatag
gctccgccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacc
tgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaac
tatcgtcttgagtccaacccggtaagacacgacttatcgccactggcagcagccactggtaacaggattagca
gagcgaggtatgtaggcggtgctacagagttcttgaagtggtggcctaactacggctacactagaaggacagt
atttggtatctgcgctctgctgaagccagttaccttcggaaaaagagttggtagctcttgatccggcaaacaa
accaccgctggtagcggtggtttttttgtttgcaagcagcagattacgcgcagaaaaaaaggatctcaagaag
atcctttgatcttttctacggggtctgacgctcagtggaacgaaaactcacgttaagggattttggtcatgag
attatcaaaaaggatcttcacctagatccttttaaattaaaaatgaagttttaaatcaatctaaagtatatat
gagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgc
tgcaatgataccgcgagacccacgctcaccggctccagatttatcagcaataaaccagccagccggaagggcc
gagcgcagaagtggtcctgcaactttatccgcctccatccagtctattaattgttgccgggaagctagagtaa
gtagttcgccagttaatagtttgcgcaacgttgttgccattgctgcaggcatcgtggtgtcacgctcgtcgtt
tggtatggcttcattcagctccggttcccaacgatcaaggcgagttacatgatccccatgttgtgcaaaaaa
gcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaa
gtcattctgagaatagtgtatgcggcgaccgagttgctcttgcccggcgtcaacacgggataataccgcgcca
catagcagaactttaaaagtgctcatcattggaaaacgttcttcggggcgaaaactctcaaggatcttaccgc
tgttgagatccagttcgatgtaacccactcgtgcacccaactgatcttcagcatcttttactttcaccagcgt
ttctgggtgagcaaaaacaggaaggcaaaatgccgcaaaaaagggaataagggcgacacggaaatgttgaata
ctcatactcttccttttcaatattattgaagcatttatcagggttattgtctcatgagcggatacatatttg
aatgtatttagaaaaataaacaaatagggttccgcgcacatttccccgaaaagtgccacctgacgtctaaga
aaccattattatcatgacattaacctataaaaataggcgtatcacgaggccctttcgtcttcaagaattgtt
```

FIG. 8B-1 pAdApt.Ebo.GP.FL.(S/G).E71D (SEQ ID NO: 8)

ttaattaaccgcaattctcatgtttgacagcttatcatcatcaataatataccttattttggattgaagccaa
tatgataatgagggggtggagtttgtgacgtggcgcggggcgtgggaacggggcgggtgacgtagtagtgtgg
cggaagtgtgatgttgcaagtgtggcggaacacatgtaagcgacggatgtggcaaaagtgacgtttttggtgt
gcgccggtgtacacaggaagtgacaattttcgcgcggttttaggcggatgttgtagtaaatttgggcgtaacc
gagtaagatttggccattttcgcgggaaaactgaataagaggaagtgaaatctgaataattttgtgttactca
tagcgcgtaatatttgtctagggccgcggggactttgaccgtttacgtggagactcgcccaggtgtttttctc
aggtgttttccgcgttccgggtcaaagttggcgttttattattatagtcagtacgtaccagtgcactggccta
ggtggtcaatattggccattagccatattattcattggttatatagcataaatcaatattggctattggccat
tgcatacgttgtatccatatcataatatgtacatttatattggctcatgtccaacattaccgccatgttgaca
ttgattattgactagttattaatagtaatcaattacggggtcattagttcatagcccatatatggagttccgc
gttacataacttacggtaaatggcccgcctggctgaccgcccaacgacccccgcccattgacgtcaataatga
cgtatgttcccatagtaacgccaatagggactttccattgacgtcaatgggtggagtatttacggtaaactgc
ccacttggcagtacatcaagtgtatcatatgccaagtacgccccctattgacgtcaatgacggtaaatggccc
gcctggcattatgcccagtacatgaccttatgggactttcctacttggcagtacatctacgtattagtcatcg
ctattaccatggtgatgcggttttggcagtacatcaatgggcgtggatagcggtttgactcacggggatttcc
aagtctccaccccattgacgtcaatgggagtttgttttggcaccaaaatcaacgggactttccaaaatgtcgt
aacaactccgccccattgacgcaaatgggcggtaggcgtgtacggtgggaggtctatataagcagagctcgtt
tagtgaaccgtcagatcgcctggagacgccatccacgctgttttgacctccatagaagacaccgggaccgatc
cagcctccgcggccgggaacggtgcattggaagcttgccgcc ATGGGGGTCTTAGCCTACTCCAATTGCCCAGGGACAAATTTCGGAAAAGCTCTTTCTTTGTTTGGGTCATCA
TCTTATTCCAAAAGGCCTTTTCCATGCCTTTGGGTGTTGTGACTAACAGCACTTTAGAAGTAACAGAGATTGA
CCAGCTAGTCTGCAAGGATCATCTTGCATCTACTGACCAGCTGAAATCAGTTGGTCTCAACCTCGACGGGAGC
GGAGTATCTACTGATATCCCATCTGCAACAAAGCGTTGGGGCTTCAGATCTGGTGTTCCTCCCAAGGTGGTCA
GCTATGAAGCGGGAGAATGGGCTGAAAATTGCTACAATCTTGAAATAAAGAAGCCGGACGGGAGCGAATGCTT
ACCCCCACCGCCAGATGGTGTCAGAGGCTTTCCAAGGTGCCGCTATGTTCACAAAGCCCAAGGAACCGGGCCC
TGCCCAGGTGACTACGCCTTTCACAAGGATGGAGCTTTCTTCCTCTATGACAGGCTGGCTTCAACTGTAATTT
ACAGAGGAGTCAATTTTGCTGAGGGGGTAATTGCATTCTTGATATTGGCTAAACCAAAAGAAACGTTCCTTCA
GTCACCCCCCATTCGAGAGGCAGTAAACTACACTGAAAATACATCAAGTTATTATGCCACATCCTACTTGGAG
TATGAAATCGAAAATTTTGGTGCTCAACACTCCACGACCCTTTTCAAAATTGACAATAATACTTTTGTTCGTC
TGGACAGGCCCCACACGCCTCAGTTCCTTTTCCAGCTGAATGATACCATTCACCTTCACCAACAGTTGAGTAA
TACAACTGGGAGACTAATTTGGACACTAGATGCTAATATCAATGCTGATATTGGTGAATGGGCTTTTTGGGAA
AATAAAAAAAATCTCTCCGAACAACTACGTGGAGAAGAGCTGTCTTTCGAAGCTTTATCGCTCAACGAGACAG
AAGACGATGATGCGGCATCGTCGAGAATTACAAAGGGAAGAATCTCCGACCGGGCCACCAGGAAGTATTCGGA
CCTGGTTCCAAAGAATTCCCCTGGGATGGTTCCATTGCACATACCAGAAGGGGAAACAACATTGCCGTCTCAG
AATTCGACAGAAGGTCGAAGAGTAGGTGTGAACACTCAGGAGACCATTACAGAGACAGCTGCAACAATTATAG
GCACTAACGGCAACCATATGCAGATCTCCACCATCGGGATAAGACCGAGCTCCAGCCAAATCCCGAGTTCCTC
ACCGACCACGGCACCAAGCCCTGAGGCTCAGACCCCCACAACCCACACATCAGGTCCATCAGTGATGGCCACC
GAGGAACCAACAACACCACCGGGAAGCTCCCCCGGCCCAACAACAGAAGCACCCACTCTCACCACCCCAGAAA
ATATAACAACAGCGGTTAAAACTGTCCTGCCACAGGAGTCCACAAGCAACGGTCTAATAACTTCAACAGTAAC
AGGGATTCTTGGGAGTCTTGGGCTTCGAAAACGCAGCAGAAGACAAACTAACACCAAAGCCACGGGTAAGTGC
AATCCCAACTTACACTACTGGACTGCACAAGAACAACATAATGCTGCTGGGATTGCCTGGATCCCGTACTTTG
GACCGGGTGCGGAAGGCATATACACTGAAGGCCTGATGCATAACCAAAATGCCTTAGTCTGTGGACTTAGGCA
ACTTGCAAATGAAACAACTCAAGCTCTGCAGCTTTTCTTAAGAGCCACAACGGAGCTGCGGACATATACCATA
CTCAATAGGAAGGCCATAGATTTCCTTCTGCGACGATGGGGCGGGACATGCAGGATCCTGGGACCAGATTGTT
GCATTGAGCCACATGATTGGACAAAAACATCACTGATAAAATCAACCAAATCATCCATGATTTCATCGACAA
CCCCTTACCTAATCAGGATAATGATGATAATTGGTGGACGGGCTGGAGACAGTGGATCCCTGCAGGAATAGGC
ATTACTGGAATTATTATTGCAATTATTGCTCTTCTTTGCGTTTGCAAGCTGCTTTGC
tgataatctagacgagatccgaacttgtttattgcagcttataatggttacaaataaagcaatagcatcacaa
atttcacaaataaagcatttttttcactgcattctagttgtggtttgtccaaactcatcaatgtatcttatca
tgtctagatctgtactgaaatgtgtgggcgtggcttaagggtgggaaagaatatataaggtgggggtcttatg
tagttttgtatctgttttgcagcagccgccgccgccatgagcaccaactcgtttgatggaagcattgtgagct
catatttgacaacgcgcatgcccccatgggccggggtgcgtcagaatgtgatgggctccagcattgatggtcg
ccccgtcctgcccgcaaactctactaccttgacctacgagaccgtgtctggaacgccgttggagactgcagcc
tccgccgccgcttcagccgctgcagccaccgcccgcgggattgtgactgactttgctttcctgagcccgcttg
caagcagtgcagcttcccgttcatccgcccgcgatgacaagttgacggctcttttggcacaattggattcttt
gacccgggaacttaatgtcgtttctcagcagctgttggatctgcgccagcaggtttctgccctgaaggcttcc
tcccctcccaatgcggtttaaaacataaataaaaaaccagactctgtttggatttggatcaagcaagtgtctt

FIG. 8B-2

```
gctgtctttatttaggggttttgcgcgcgcggtaggcccgggaccagcggtctcggtcgttgagggtcctgtg
tattttttccaggacgtggtaaaggtgactctggatgttcagatacatgggcataagcccgtctctggggtgg
aggtagcaccactgcagagcttcatgctgcggggtggtgttgtagatgatccagtcgtagcaggagcgctggg
cgtggtgcctaaaaatgtctttcagtagcaagctgattgccaggggcaggcccttggtgtaagtgtttacaaa
gcggttaagctgggatgggtgcatacgtggggatatgagatgcatcttggactgtatttttaggttggctatg
ttcccagccatatccctccggggattcatgttgtgcagaaccaccagcacagtgtatccggtgcacttgggaa
atttgtcatgtagcttagaaggaaatgcgtggaagaacttggagacgcccttgtgacctccaagattttccat
gcattcgtccataatgatggcaatgggcccacgggcggcggcctgggcgaagatatttctgggatcactaacg
tcatagttgtgttccaggatgagatcgtcataggccattttttacaaagcgcgggcggagggtgccagactgcg
gtataatggttccatccggcccaggggcgtagttaccctcacagatttgcatttcccacgctttgagttcaga
tggggggatcatgtctacctgcggggcgatgaagaaaacggtttccggggtaggggagatcagctgggaagaa
agcaggttcctgagcagctgcgacttaccgcagccggtgggcccgtaaatcacacctattaccggctgcaact
ggtagttaagagagctgcagctgccgtcatccctgagcagggggggccacttcgttaagcatgtccctgactcg
catgtttccctgaccaaatccgccagaaggcgctcgccgcccagcgatagcagttcttgcaaggaagcaaag
tttttcaacggtttgagaccgtccgccgtaggcatgcttttgagcgtttgaccaagcagttccaggcggtccc
acagctcggtcacctgctctacggcatctcgatccagcatatctcctcgtttcgcgggttggggcggctttcg
ctgtacggcagtagtcggtgctcgtccagacgggccagggtcatgtctttccacggggcgcaggtcctcgtca
gcgtagtctgggtcacggtgaagggggtgcgctccgggctgcgcgctggccagggtgcgcttgaggctggtcct
gctggtgctgaagcgctgccggtcttcgccctgcgcgtcggccaggtagcatttgaccatggtgtcatagtcc
agcccctccgcggcgtggcccttggcgcgcagcttgcccttggaggaggcgccgcacgagggggcagtgcagac
ttttgagggcgtagagcttgggcgcgagaaatacccgattccggggagtaggcatccgcgccgcaggccccgca
gacggtctcgcattccacgagccaggtgagctctggccgttcggggtcaaaaaccaggtttcccccatgctttt
ttgatgcgtttcttacctctggtttccatgagccggtgtccacgctcggtgacgaaaaggctgtccgtgtccc
cgtatacagacttgagaggcctgtcctcgagcggtgttccgcggtcctcctcgtatagaaactcggaccactc
tgagacaaaggctcgcgtccaggccagcacgaaggaggctaagtgggagggtagcggtcgttgtccactagg
gggtccactcgctccagggtgtgaagacacatgtcgccctcttcggcatcaaggaaggtgattggtttgtagg
tgtaggccacgtgaccgggtgttcctgaagggggggctataaaaggggtgggggcgcgttcgtcctcactctc
ttccgcatcgctgtctgcgagggccagctgttggggtgagtcgacgcgaggctggatggccttccccattatg
attcttctcgcttccggcggcatcgggatgcccgcgttgcaggccatgctgtccaggcaggtagatgacgacc
atcagggacagcttcaaggccagcaaaaggccaggaaccgtaaaaaggccgcgttgctggcgttttttccatag
gctccgccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacc
tgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaac
tatcgtcttgagtccaacccggtaagacacgacttatcgccactggcagcagccactggtaacaggattagca
gagcgaggtatgtaggcggtgctacagagttcttgaagtggtggcctaactacggctacactagaaggacagt
atttggtatctgcgctctgctgaagccagttaccttcggaaaaagagttggtagctcttgatccggcaaacaa
accaccgctggtagcggtggtttttttgtttgcaagcagcagattacgcgcagaaaaaaaggatctcaagaag
atcctttgatcttttctacggggtctgacgctcagtggaacgaaaactcacgttaagggattttggtcatgag
attatcaaaaaggatcttcacctagatccttttaaattaaaaatgaagttttaaatcaatctaaagtatatat
gagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgc
tgcaatgataccgcgagacccacgctcaccggctccagatttatcagcaataaaccagccagccggaagggcc
gagcgcagaagtggtcctgcaactttatccgcctccatccagtctattaattgttgccgggaagctagagtaa
gtagttcgccagttaatagtttgcgcaacgttgttgccattgctgcaggcatcgtggtgtcacgctcgtcgtt
tggtatggcttcattcagctccggttcccaacgatcaaggcgagttacatgatccccatgttgtgcaaaaaa
gcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaa
gtcattctgagaatagtgtatgcggcgaccgagttgctcttgcccggcgtcaacacgggataataccgcgcca
catagcagaactttaaaagtgctcatcattggaaaacgttcttcggggcgaaaactctcaaggatcttaccgc
tgttgagatccagttcgatgtaacccactcgtgcacccaactgatcttcagcatcttttactttcaccagcgt
ttctgggtgagcaaaaacaggaaggcaaaatgccgcaaaaagggaataagggcgacacggaaatgttgaata
ctcatactcttcctttttcaatattattgaagcatttatcagggttattgtctcatgagcggatacatatttg
aatgtatttagaaaaataaacaataggggttccgcgcacatttccccgaaaagtgccacctgacgtctaaga
aaccattattatcatgacattaacctataaaaataggcgtatcacgaggccctttcgtcttcaagaattgtt
```

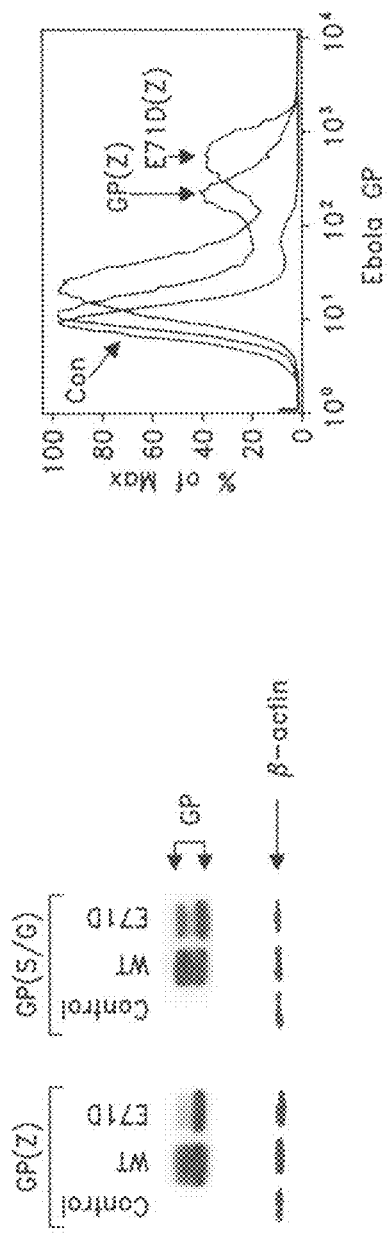
FIG. 14A
FIG. 14B
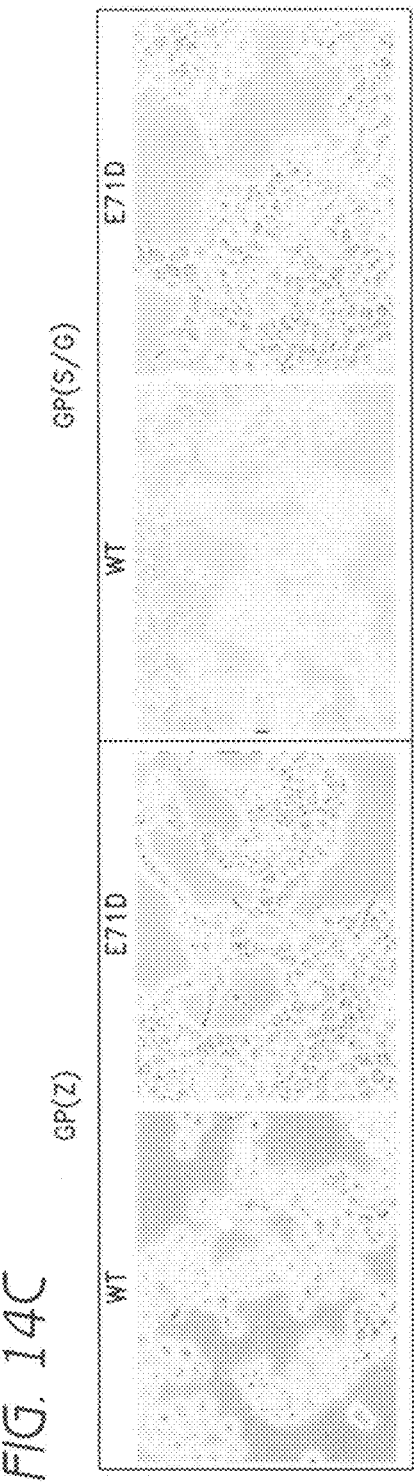
FIG. 14C

| Group | Immunogen | Dose (PU) | Survival |
|---|---|---|---|
| 1 | GP(Z) + NP(Z) | $10^{10}$ each | 3/3 |
| 2 | GP(Z) E71D + NP(Z) | $10^{10}$ each | 2/3 |
| 3 | GP(Z) E71D + GP(G) E71D + NP(Z) | $10^{10}$ each | 1/3 |
| 4 | GP(Z) E71D + GP(G) E71D | $10^{10}$ each | 3/3 |
| 5 | Control | 0 | 0/1 |

Ebola Zaire Glycoprotein (SEQ ID NO: 9)

MGVTGILQLPRDRFKRTSFFLWVIILFQRTFSIPLGVIHNSTLQVSDVDKLVCRDKLS
STNQLRSVGLNLEGNGVATDVPSATKRWGFRSGVPPKVVNYEAGEWAENCYNLE
IKKPDGSECLPAAPDGIRGFPRCRYVHKVSGTGPCAGDFAFHKEGAFFLYDRLAST
VIYRGTTFAEGVVAFLILPQAKKDFFSSHPLREPVNATEDPSSGYYSTTIRYQATGF
GTNETEYLFEVDNLTYVQLESRFTPQFLLQLNETIYTSGKRSNTTGKLIWKVNPEID
TTIGEWAFWETKKNLTRKIRSEELSFTVVSNGAKNISGQSPARTSSDPGTNTTTEDH
KIMASENSSAMVQVHSQGREAAVSHLTTLATISTSPQSLTTKPGPDNSTHNTPVYK
LDISEATQVEQHHRRTDNDSTASDTPSATTAAGPPKAENTNTSKSTDFLDPATTTSP
QNHSETAGNNNTHHQDTGEESASSGKLGLITNTIAGVAGLITGGRRTRREAIVNAQ
PKCNPNLHYWTTQDEGAAIGLAWIPYFGPAAEGIYIEGLMHNQDGLICGLRQLANE
TTQALQLFLRATTELRTFSILNRKAIDFLLQRWGGTCHILGPDCCIEPHDWTKNITD
KIDQIIHDFVDKTLPDQGDNDNWWTGWRQWIPAGIGVTGVVIAVIALFCICKFVF

RECOMBINANT EXPRESSION VECTORS COMPRISING A HUMAN CODON-OPTIMIZED MARBURG VIRUS (MARV) ANGOLA GLYCOPROTEIN GENE INSERT AND METHOD OF IMMUNIZATION EMPLOYING SAID VECTOR

RELATED APPLICATIONS

This application is a U.S. National Phase of International Application No.: PCT/US2005/034798, filed Sep. 27, 2005, and published in English as WO 2006/037038 on Apr. 6, 2006, which claims benefit of U.S. Provisional Application No. 60/613,883 filed Sep. 27, 2004, U.S Provisional Application No. 60/677,606 filed May 03, 2005, U.S. Provisional Application No. 60/679,767 filed May 10, 2005, U.S. Provisional Application No. 60/701,694 filed Jul. 22, 2005, and U.S. Provisional Application No. 60/715,874 filed Sep. 9, 2005, all of which are hereby incorporated by reference in their entireties.

FIELD OF THE INVENTION

The present invention relates generally to viral vaccines and, more particularly, to filovirus vaccines and methods of eliciting an immune response against a filovirus or a disease caused by infection with filovirus.

BACKGROUND OF THE INVENTION

Ebola virus and Marburg virus make up the family Filoviridae. The family is divided into two genera, currently designated as "Ebola-like viruses" and "Marburg-like viruses." There are four subtypes within the "Ebola-like viruses," Zaire (type species), Sudan, Reston, and Côte d'Ivoire (Ivory Coast). A single type, Marburg virus, makes up the "Marburg-like viruses."

The glycoprotein (GP) is the sole structural protein making up the virion surface spikes that mediate virus entry into susceptible host cells through receptor binding. GP is the most studied of the filovirus proteins, not only for its importance in virus entry and pathogenesis but because it is a prime target for vaccine development. Research on filovirus GP has been facilitated through the use of recombinant DNA technology to permit biochemical and functional assays without the constraints of working with the infectious filovirus.

GP expression in cultured human endothelial and epithelial cells causes cell rounding and detachment (Yang Z.-Y. et al. 2000 *Nat Med* 6:886-889). These effects require the presence of the mucin-like serine and threonine-rich domain of GP. The cytotoxic effects of GP on macrophage and endothelial cell function disrupt inflammatory cell function and the integrity of the vasculature. In addition, by altering the cell surface expression of adhesion proteins and immune recognition molecules, Ebola virus may disrupt processes critical to immune activation and cytolytic-T-cell function. These phenomena likely account for the dysregulation of the inflammatory response and the vascular dysfunction characteristic of lethal Ebola virus infection, providing a rationale for focusing on GP as a target for a preventative vaccine.

SUMMARY OF THE INVENTION

The invention is related to a nucleic acid molecule comprising a polynucleotide encoding a modified filovirus glycoprotein (GP) having at least one amino acid change located in a relatively conserved region of said GP that decreases in vitro cytotoxicity and retains immunogenicity when compared to in vitro cytotoxicity and immunogenicity of a wild type filovirus GP.

In one embodiment, the amino acid change is positioned in the N-terminal domain, excluding the conserved cysteine residues, and is located at amino acid position 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 or 300 in Ebola Zaire GP in an exemplary manner or corresponding thereto in other strains of said GP.

In another embodiment, the amino acid change is located at amino acid position 71 or 102 in Ebola Zaire GP in an exemplary manner or corresponding thereto in other strains of said GP.

In yet another embodiment, the amino acid change is E71D or G102A in Ebola Zaire GP in an exemplary manner or corresponding thereto in other strains of said GP.

In still another embodiment, the modified filovirus GP is encoded by the insert of SEQ ID NO:1, SEQ ID NO:2, SEQ D NO:3, SEQ ID NO:4, SEQ ID NO:6, SEQ ID NO:7 or SEQ ID NO:8, or sequence having at least 95% identity thereto.

In yet a further embodiment, the polynucleotide encoding the modified filovirus GP has a sequence taken from the insert of SEQ ID NO:1, SEQ ID NO:2, SEQ ID NO:3, SEQ ID NO:4, SEQ ID NO:6, SEQ ID NO:7, or SEQ ID NO:8, or sequence having at least 95% identity thereto.

Other embodiments of the invention are related to modified filovirus GPs encoded by the nucleic acid molecules, plasmid DNAs comprising the nucleic acid molecules, recombinant viruses comprising the nucleic acid molecules, adenoviruses comprising the nucleic acid molecules, pharmaceutical compositions comprising the nucleic acid molecules or the modified filovirus GPs in a therapeutically effective dose, vaccine compositions comprising the nucleic acid molecules or the modified filovirus GPs in a prophylactically effective dose, antibodies that are specifically reactive with the modified filovirus GPs, and related methods of making and using the same.

BRIEF DESCRIPTION OF THE DRAWINGS

FIG. 1. A) VRC6612 (pCMV/R-Ebola GP (S/G) (G to A)/h) construct map (see human codon-optimized Ebola/Marburg plasmids in Table 2). B) Nucleotide sequence of VRC6612 (SEQ ID NO: 1).

FIG. 2. A) VRC6615 (pCMV/R-Ebola GP (Z) (full length G to A)/h) construct map (see human codon-optimized Ebola/Marburg plasmids in Table 2). B) Nucleotide sequence of VRC6615 (SEQ ID NO: 2).

Figure 3A:
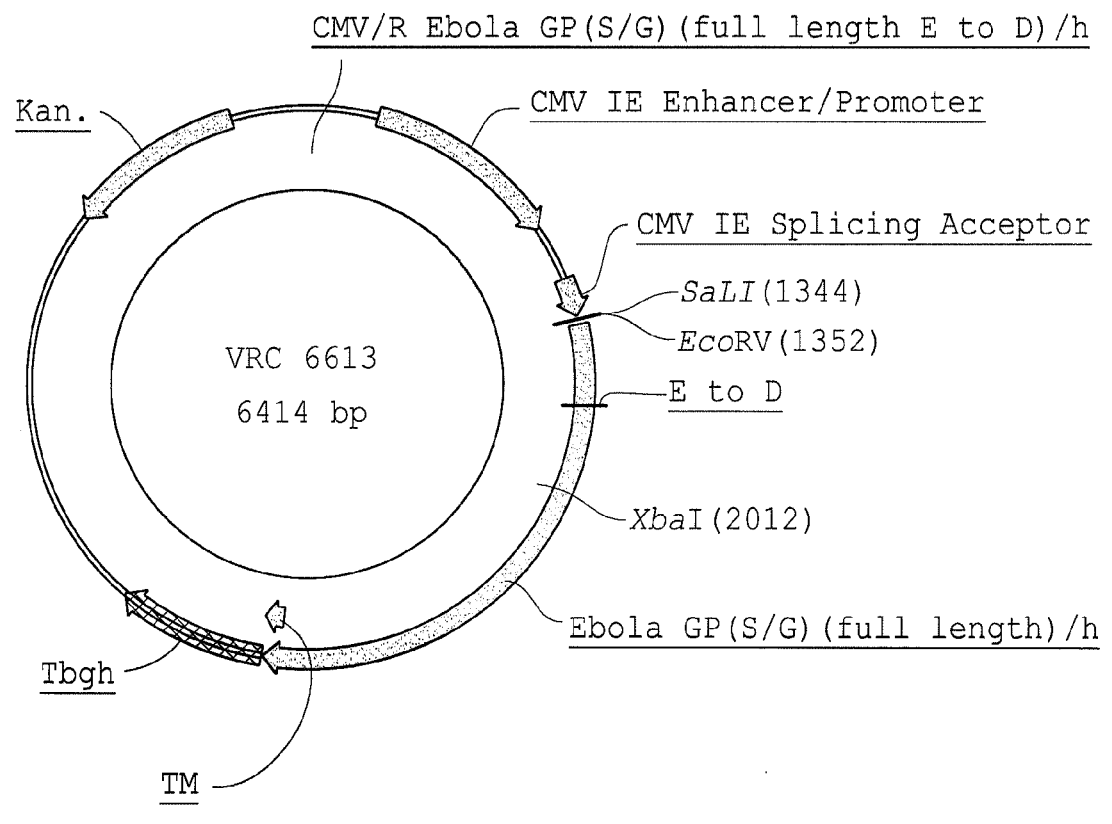

FIG. 3. A) VRC6613 (pCMV/R-Ebola GP (S/G) (E to D)/h) construct map (see human codon-optimized Ebola/Marburg plasmids in Table 2). B) Nucleotide sequence of VRC6613 (SEQ ID NO: 3).

FIG. 4. A) VRC6616 (pCMV/R-Ebola GP (Z) (full length E to D)/h) construct map (see human codon-optimized Ebola/Marburg plasmids in Table 2). B) Nucleotide sequence of VRC6613 (SEQ ID NO: 4).

FIG. 13. Comparative efficacy of wild type and point mutant glycoprotein vaccines against lethal Ebola virus challenge. A) Kaplan-Meier survival curve of macaques: immunization and challenge were performed with the 1995 Zaire subtype Ebola virus as in FIG. 11A. B) Immune responses in immunized animals. Left and middle panels: intracellular flow cytometry was performed to quantify TNF-α production from Ebola-specific CD4 or CD8 lymphocytes, respectively, from animals immunized as indicated. Immune responses were measured at 3 weeks post-immunization. Circle, diamond, square: responses for individual animals. Horizontal line: average of individual responses in the immunization group. Results represent the percent cytokine positive in the gated lymphocyte group and background stimulation (DMSO alone) has been subtracted from each sample. Right panel: ELISA titers of Ebola GP-specific antibodies in serum of vaccinated animals collected at week 3 post-immunization. ELISA results represent endpoint dilution titers determined by optical density as described in Example 1.

FIG. 14. Elimination of GP cytopathic effects with single point mutation. A) Expression of point mutants in 293 cells. Ebola GP proteins from supernatants and cell lysates in (A) were visualized by SDS-PAGE and Western blot using a polyclonal antibody against Ebola GP. B) Reactivity of point mutants with a conformation-dependent antibody. 293 cells were transfected with a control plasmid (Con), or plasmids expressing wild type (GP(Z)) or mutant (E71D(Z)) proteins. Eighteen hours post-transfection, cells were harvested, stained with a GP-specific antibody and cell surface GP expression was analyzed by flow cytometry. C) Elimination of cell rounding by amino acid substitution at position 71. 293 cells were transfected with a plasmid encoding vector control, wild type Ebola glycoprotein from Zaire (GP(Z)) or Sudan-Gulu (GP(S/O)) or their respective point mutations (E71D (Z)), E71D(S/G)). Cell monolayers were visualized under phase contrast using a Nikon 40× objective and photographed at 24 hours post transfection.

FIG. 17. Comparative efficacy of wild type GP vs. point mutant immunogens.

FIG. 20. Ebola Zaire GP amino acid sequence (SEQ ID NO: 9).

TABLE 1

Filovirus Genbank Accession Numbers

Figure 5A:
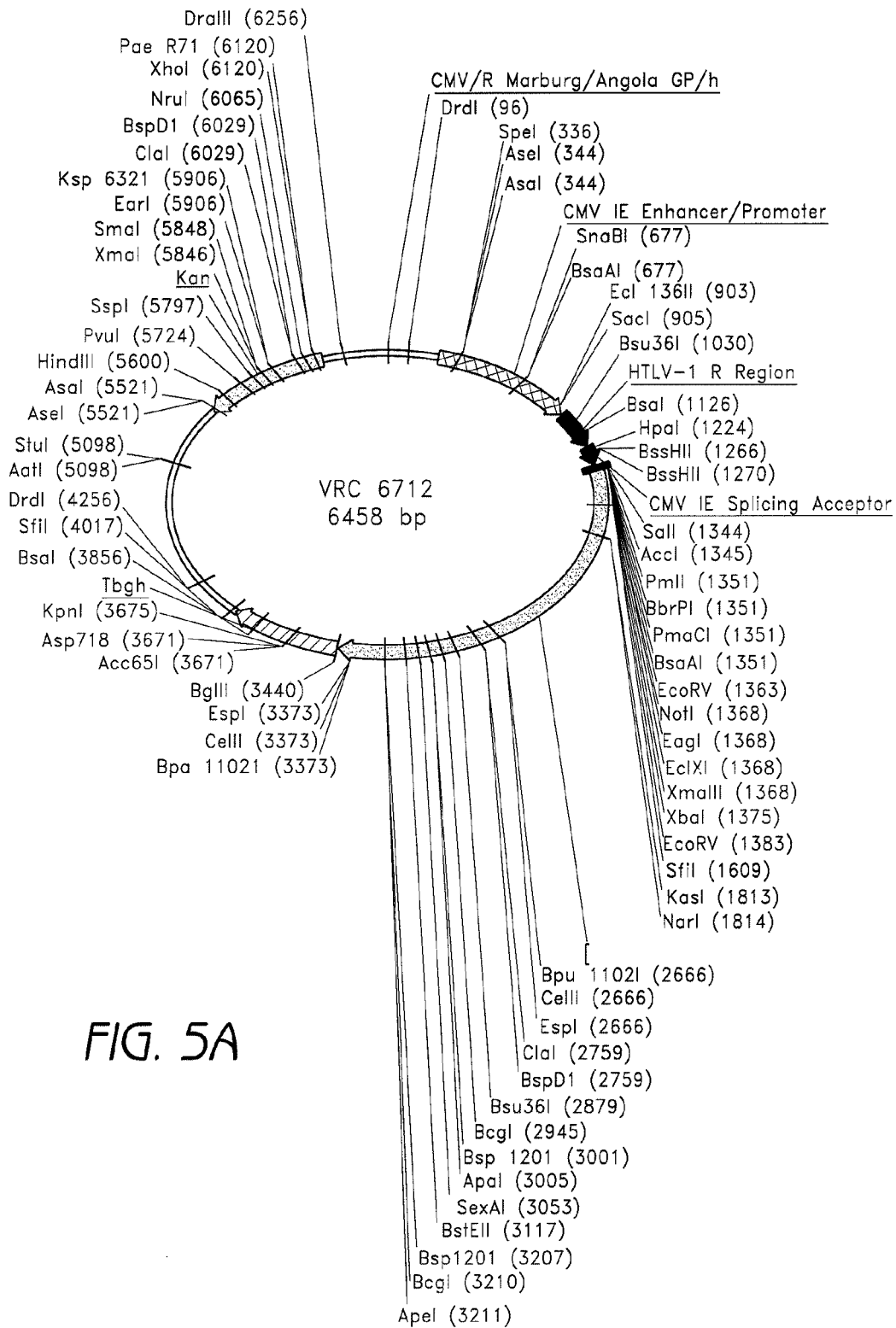
FIG. 5. A) VRC6712 (pCMV/R-Marburg/Angola GP/h) construct map (see human codon-optimized Ebola/Marburg plasmids in Table 2). B) Nucleotide sequence of VRC6712 (SEQ ID NO: 5).
Figure 6A:
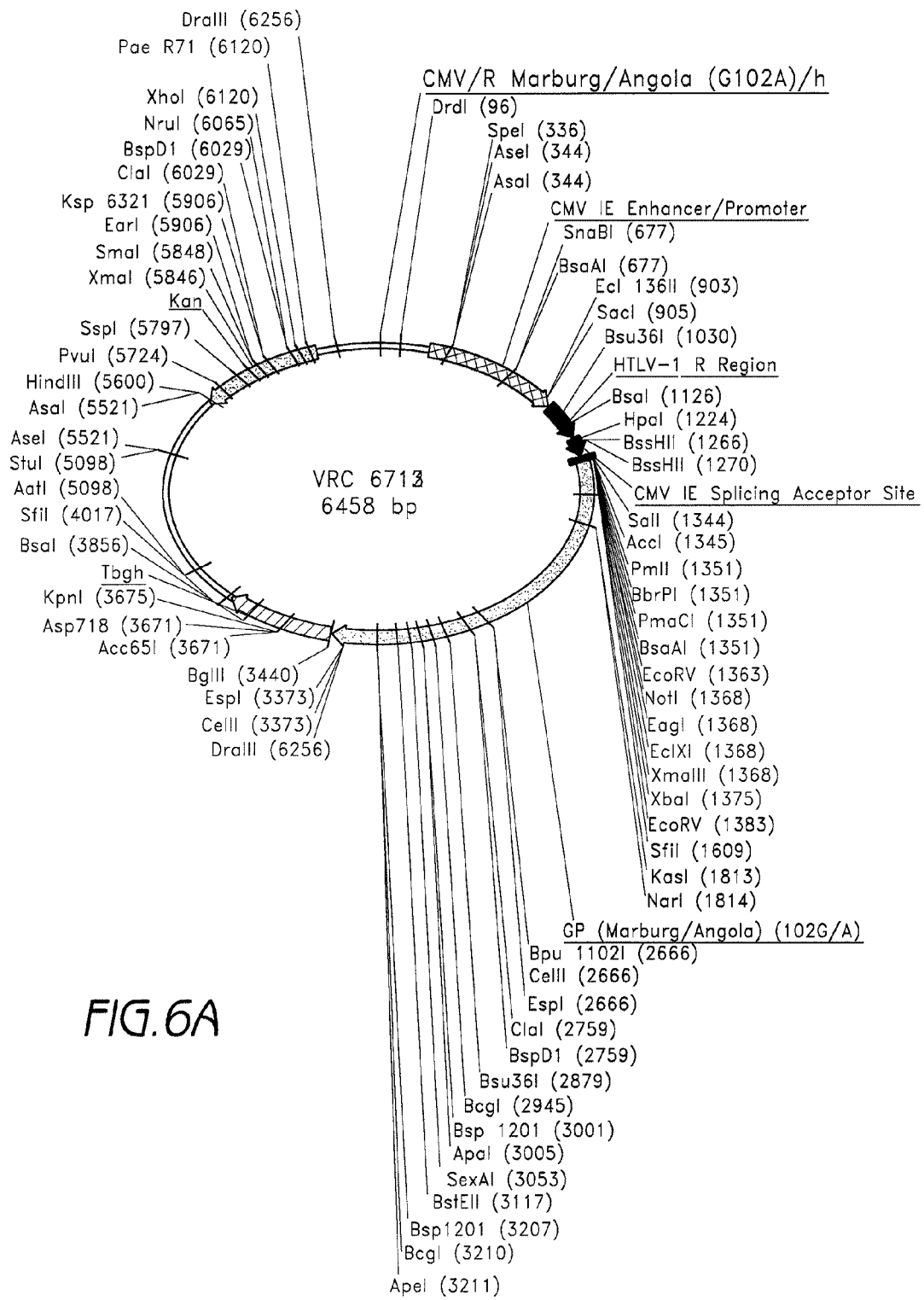
FIG. 6. A) VRC6713 (pCMV/R Marburg/Angola GP (G102A)/h) construct map (see human codon-optimized Ebola/Marburg plasmids in Table 2). B) Nucleotide sequence of VRC6713 (SEQ ID NO: 6).
Figure 7A:
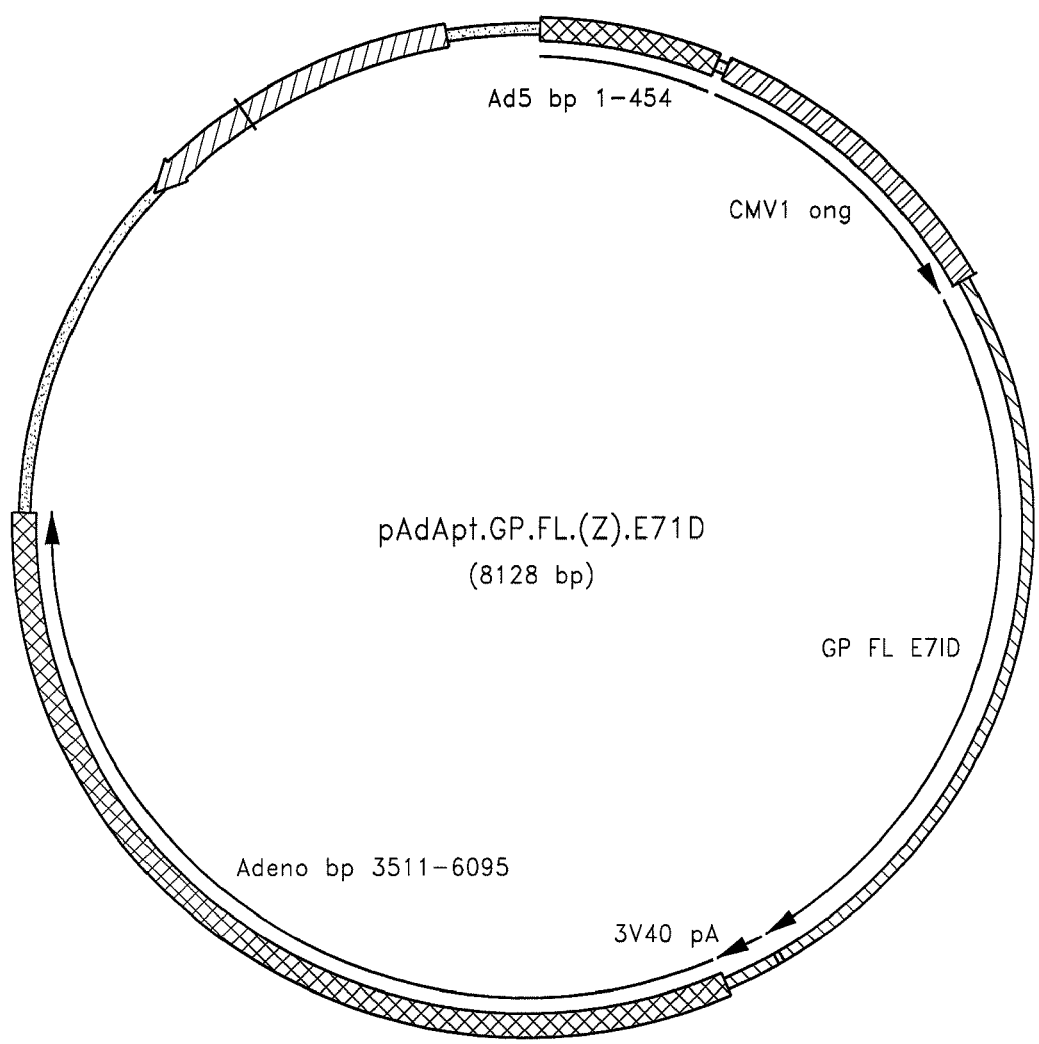
FIG. 7. A) pAdApt.Ebo.GP.FL.(Z).E71D (adenoviral adaptor plasmid-Ebola/Zaire GP (full length E71D)/h). B) Nucleotide sequence of pAdApt.Ebo.GP.FL.(Z).E71D (SEQ ID NO: 7). Upper case is the coding sequence Ebo.GP.FL.(Z).E71D, the boxed region shows the E71D mutation and restriction site sequences used for cloning are bold and underlined.
Figure 8A:
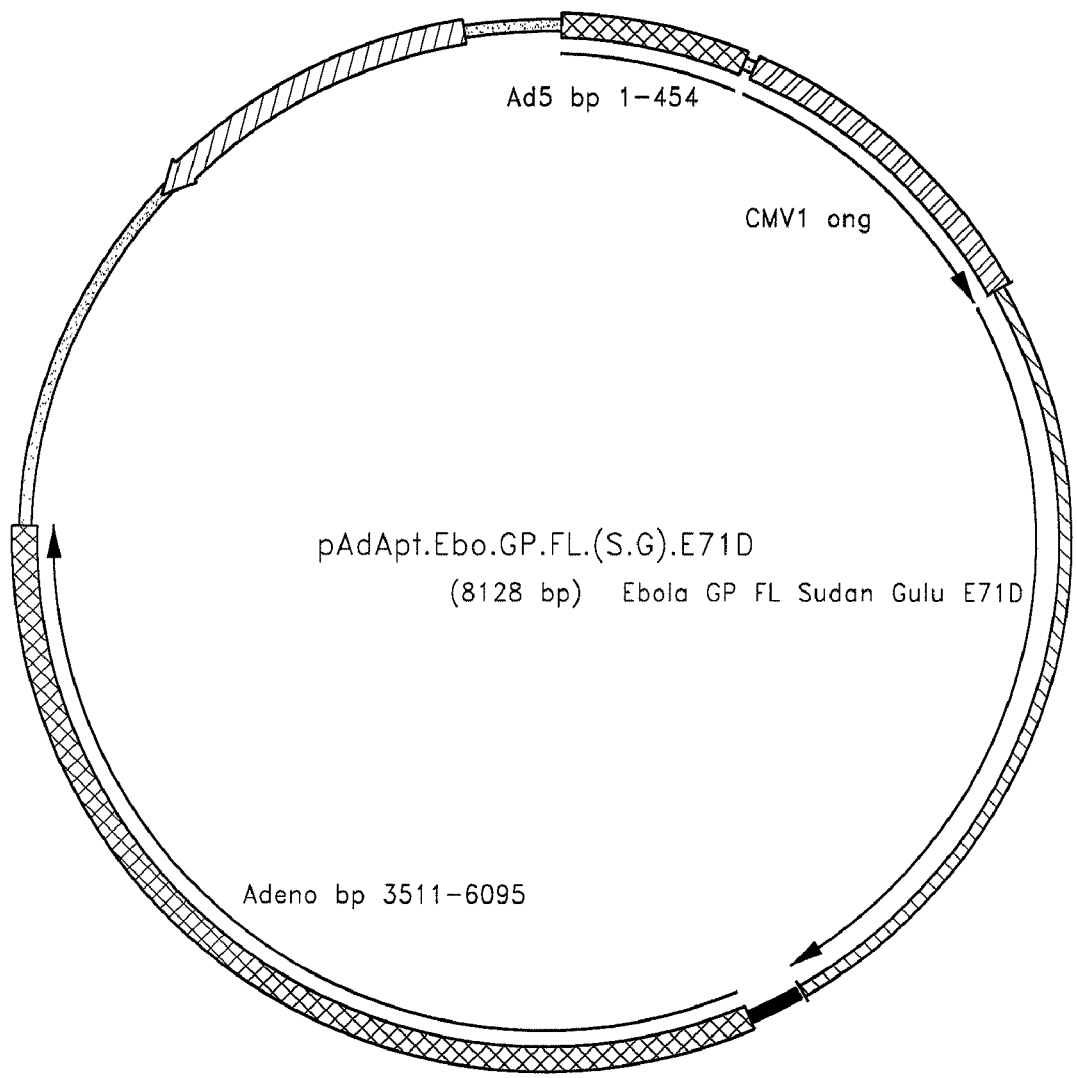
FIG. 8. A) pAdApt.Ebo.GP.FL.(S/G).E71D (adenoviral adaptor plasmid-Ebola/(Sudan/Gulu) GP (full length E71D)/h). B) Nucleotide sequence of pAdApt.Ebo.GP.FL.(S/G).E71D (SEQ ID NO: 8). Upper case is the coding sequence Ebo.GP.FL.(S/G).E71D, the boxed region shows the E71D mutation and restriction site sequences used for cloning are bold and underlined.
Figure 8B:
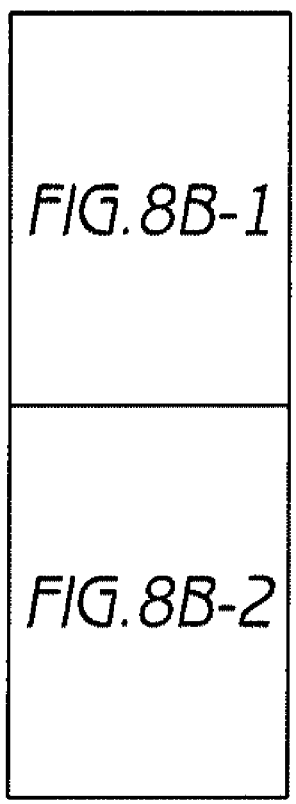
Figure 9:
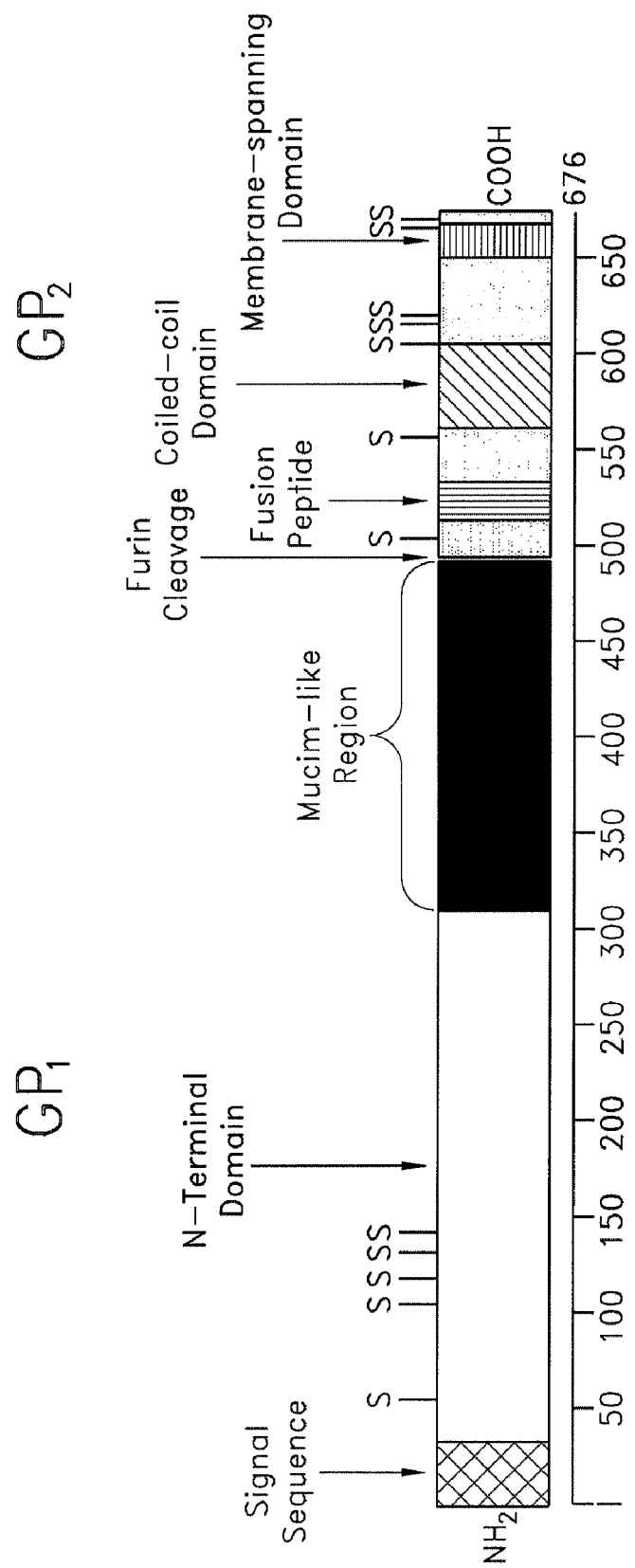
FIG. 9. Schematic representation of Ebola virus GP. The GP1 and GP2 subunits of GP are drawn to scale (residue numbers are indicated below the diagram). The positions of the signal sequence, conserved cysteine residues (S), the mucin-like region (region of O-linked glycosylation), the furin cleavage site, the fusion peptide, the coiled-coil domain, and the membrane spanning domain are indicated.

| Virus | Subtype | Strain | "aa71" | "aa102" | Genbank Accession No. |
|---|---|---|---|---|---|
| Ebola | Ivory Coast | Coto d'Ivore-Tai Forest, 1994 | E | G | U28006 |
| | Reston | Reston, 1989 | E | G | U23152, NC_004161, AF034645 |
| | | Philippines, 1989 | E | G | U23416 |
| | | Pennsylvania | E | G | AY769362, AF522874 |
| | | Siena, 1992 | E | G | U23417 |
| | | Texas, 1996 | | | |
| | Sudan | Boniface, 1976 | E | G | U28134 |
| | | Maleo, 1979 | E | G | U23069, Q66798 |
| | | Gulu-Uganda, 2000-2001 | E | G | AY729654, AY344234, AY316199 |
| | Zaire | Mayinga-Zaire, 1976 | E | G | AY142960, AF499101, AF272001, AF086833, U23187, NC_002549 |
| | | Zaire-Zaire, 1976 | E | G | AY354458, U28077, U31033, P87666 |
| | | Eckron-Zaire, 1976 | E | G | U81161 |
| | | Bouee-96 | E | G | AY058898 |
| | | Tandala-Zaire, 1977 | | | |
| | | Kikwit-Zaire, 1995 | | | |
| | | Gabon-Zaire, 1994-1997 | E | G | U77384 |
| | | Mendemba A, 2001 | G | G | AY526105 (G at 71) |
| | | Mvoula, 2003 | E | G | AY526104 |
| | | Yembelengoye, 2002 | | G | AY526103 (partial seq, unknown at 71) |
| | | Entsiami, 2002 | G | G | AY526102 (G at 71) |
| | | Makoukou, 2001 | G | G | AY526101 (G at 71) |
| | | Etkangaye, 2001 | G | G | AY526100 (G at 71) |
| | | Olloba | G | G | AY526099 (G at 71) |
| | | Mendemba B, 2001 | G | G | AY526098 (G at 71) |
| Marburg | | Musoke-Kenya, 1980 | | G | Z12132 |
| | | Ratayczak-West Germany, 1967 | | G | AF005735 |
| | | Popp-West Germany, 1967 | | G | NC_001608, Z29337, X68493 |
| | | Voege-Yugoslavia, 1967 | | | |
| | | Ozolin-Zimbabwe, 1987 | | G | AY358025, AF005733 |
| | | Ravn-Kenya, 1987 | | G | AF005734 |
| | | Angola, 2004-2005 | | G | (see FIG. 5 and SEQ ID NO: 5, human codon-optimized) |
| | | pp3 guinea pig lethal variant | | G | AY430365 |
| | | pp4 guinea pig nonlethal variant | | G | AY430366 |

TABLE 2

Human Codon-Optimized Ebola/Marburg Plasmids

| Construct | Construct Name/Description | Construct Map Name | SEQ ID NO | Figure |
|---|---|---|---|---|
| VRC6612 | pCMV/R-Ebola GP (S/G) (G to A)/h* | CMV/R-Ebola GP (S/G) (G to A)/h | 1 | 1 |
| VRC6615 | pCMV/R-Ebola GP (Z) (full length G to A)/h | CMV/R-Ebola GP (Z) (full length G to A)/h | 2 | 2 |
| VRC6613 | pCMV/R-Ebola GP (S/G) (E to D)/h | CMV/R-Ebola GP (S/G) (E to D)/h | 3 | 3 |
| VRC6616 | pCMV/R-Ebola GP (Z) (full length E to D)/h | CMV/R-Ebola GP (Z) (full length E to D)/h | 4 | 4 |
| VRC6712 | pCMV/R-Marburg/Angola GP/h | CMV/R-Marburg/Angola GP/h | 5 | 5 |
| VRC6713 | pCMV/R Marburg/Angola GP (G102A)/h | CMV/R Marburg/Angola GP (G102A)/h | 6 | 6 |
| pAdApt.Ebo.GP.FL.(Z).E71D | pAdApt.Ebo.GP.FL.(Z).E71D (adenoviral adaptor plasmid-Ebola/Zaire GP (full length E71D)/h) | AdApt.Ebo.GP.FL.(Z).E71D (adenoviral adaptor plasmid-Ebola/Zaire GP (full length E71D)/h) | 7 | 7 |
| pAdApt.Ebo.GP.FL.(S/G).E71D | pAdApt.Ebo.GP.FL.(S/G).E71D (adenoviral adaptor plasmid-Ebola/(Sudan/Gulu) GP (full length E71D)/h) | AdApt.Ebo.GP.FL.(S/G).E71D (adenoviral adaptor plasmid-Ebola/(Sudan/Gulu) GP (full length E71D)/h) | 8 | 8 |

*h = human codon-optimized

DETAILED DESCRIPTION OF THE PREFERRED EMBODIMENT

In the absence of effective therapies for Ebola virus infection, the development of a vaccine becomes an important strategy to contain outbreaks. Immunization with DNA and/or replication-defective adenoviral (rAd) vectors encoding the Ebola glycoprotein (GP) and nucleoprotein (NP) has been previously shown to confer specific protective immunity in nonhuman primates (Sullivan, N. J. et al. 2000 Nature 408: 605-609; Sullivan, N. J. et al. 2003 Nature 424:681-684). GP can exert cytopathic effects on transfected cells in vitro (Yang, Z.-Y. et al. 2000 Nat Med 6:886-889) and multiple GP forms have been identified in nature, raising the question of which would be optimal for a human vaccine. To address this question, we have explored the efficacy of mutant GPs from multiple Ebola virus strains with reduced in vitro cytopathicity and analyzed their protective effects in the primate challenge model, with or without NP. Deletion of the GP transmembrane domain eliminated in vitro cytopathicity but reduced its protective efficacy by at least one order of magnitude. In contrast, single point mutations were identified that abolish in vitro cytopathicity but retained immunogenicity and conferred immune protection in the absence of NP. The minimal effective rAd dose was established at $10^{10}$ particles, two logs lower than used previously. Expression of specific GPs alone vectored by rAd are sufficient to confer protection against lethal challenge in a relevant nonhuman primate model, providing the basis for identification of a vaccine.

Definitions

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology* $3^{rd}$ ed., J. Wiley & Sons, Chichester, N.Y., 2001, and *Fields Virology* $4^{th}$ ed., Knipe D. M. and Howley P. M. eds, Lippincott Williams & Wilkins, Philadelphia 2001.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a modified filovirus structural gene product; and DNA molecules which comprise a sequence substantially different from those described above but which, due to the degeneracy of the genetic code, still encode an ORF of a modified filovirus structural gene product. Of course, the genetic code is well known in the art. Degenerate variants optimized for human codon usage are preferred.

A filovirus structural gene product, e.g., glycoprotein (GP), the sole structural protein making up the virion surface spikes that mediate virus entry into susceptible host cells through receptor binding, is modified by having at least one amino acid change that decreases in vitro cytotoxicity and retains immunogenicity when compared to in vitro cytotoxicity and immunogenicity of a wild type (e.g., naturally occurring) filovirus GP. The amino acids of particular importance to the in vitro cytotoxicity are by no means limited to the exact position as defined for the, e.g., Zaire strain of Ebola virus but are simply used in an exemplary manner to point out the preferred amino acids being at that position or corresponding to that position in other strains such as found in Sudan strain of Ebola virus or Angola strain of Marburg virus and filoviruses in general since they are highly conserved. For filoviruses other than the Ebola Zaire strain the numbering of the positions of the preferred amino acids is often different but an expert in the field of the molecular biology of filoviruses will easily identify these preferred amino acids by their position relative to the highly conserved amino acids of said glycoprotein.

The present invention is further directed to fragments of the nucleic acid molecules described herein. By a fragment of a nucleic acid molecule having the nucleotide sequence of an ORF encoding a modified filovirus structural gene product is intended fragments at least about 15 nt., and more preferably at least about 20 nt., still more preferably at least about 30 nt., and even more preferably, at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a modified filovirus structural gene product. By a fragment at least 20 nt. in length, for example, is intended fragments which include 20 or more contiguous bases from the nucleotide sequence of the ORF encoding a modified filovirus structural gene product.

Preferred nucleic acid fragments of the present invention include nucleic acid molecules encoding epitope-bearing portions of the filovirus structural protein. In particular, such nucleic acid fragments of the present invention include nucleic acid molecules encoding epitope-bearing domains of a filovirus structural protein, where the domain is the N-terminal domain, the mucin-like domain, the furin cleavage site, the fusion peptide domain, the coiled-coli domain, the membrane spanning domain, and the intracellular domain, and any combination thereof, for example, a filovirus glycoprotein having a truncation at the carboxy terminus to delete the membrane spanning and intracellular domain, a filovirus glycoprotein having a truncation at the carboxy terminus to delete the coiled-coil domain and membrane-spanning and intracellular domain, a filovirus glycoprotein having a truncation at the carboxy terminus to delete the fusion peptide domain, coiled-coil domain, and membrane-spanning and intracellular domain, a filovirus glycoprotein having a truncation at the carboxy terminus to delete the furin cleavage site, fusion peptide domain, coiled-coil domain, and membrane-spanning and intracellular domain, a filovirus glycoprotein having a truncation at the carboxy terminus to delete the mucin-like domain, furin cleavage site, fusion peptide domain, coiled-coil domain, and membrane-spanning and intracellular domain. Another example is a filovirus glycoprotein having an amino, internal, or carboxy deletion to delete the mucin-like domain, the furin cleavage site, the fusion peptide domain, the coiled-coil domain, the membrane-spanning domain, or the intracellular domain.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), and more preferably at least about 20 nt., still more preferably at least about 30 nt., and even more preferably about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the filovirus structural gene product or portions thereof. Also especially preferred in this regard are conservative substitutions.

Further embodiments of the invention include nucleic acid molecules comprising a polynucleotide having a nucleotide sequence at least 95% identical, and more preferably at least 96%, 97%, 98% or 99% identical to a nucleotide sequence encoding a polypeptide having the amino acid sequence of a modified filovirus structural gene product or fragment thereof or a nucleotide sequence complementary thereto.

By a polynucleotide having a nucleotide sequence at least, for example, 95% "identical" to a reference nucleotide sequence encoding a filovirus structural gene product is intended that the nucleotide sequence of the polynucleotide is identical to the reference sequence except that the polynucleotide sequence may include up to five point mutations per each 100 nucleotides of the reference nucleotide sequence encoding the Ebola virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman 1981 *Advances in Applied Mathematics* 2:1482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences described herein which encode a polypeptide having Ebola or Marburg polypeptide activity. By "a polypeptide having Ebola or Marburg, polypeptide activity" is intended polypeptides exhibiting Ebola or Marburg polypeptide activity in a particular biological assay. For example, GP polypeptide activity can be measured for changes in biological activity such as receptor binding activity, connection between GP1 and GP2, and contribution to the formation of the stalk structure of the virion peplomer, and modified GP polypeptide activity by decrease of in vitro cytotoxicity while retaining immunogenicity.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence described herein will encode a polypeptide "having Ebola or Marburg polypeptide activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ebola or Marburg polypeptide activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides a filovirus polypeptide having the amino acid sequence encoded by an open reading frame (ORF) of a modified filovirus structural gene, or a peptide or polypeptide comprising a portion thereof (e.g., soluble GP). It will be recognized in the art that some amino acid sequences of the filovirus polypeptides can be varied without significant effect of the structure or function of the protein. If such differences in sequence are contemplated, it should be remembered that there will be critical areas on the protein which determine activity.

Thus, the invention further includes variations of the filovirus polypeptide which show substantial filovirus polypeptide activity or which include regions of filovirus protein such as the protein portions discussed below. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table A).

TABLE A

| Conservative Amino Acid Substitutions | |
|---|---|
| Aromatic | Phenylalanine |
|  | Tryptophan |
|  | Tyrosine |
| Ionizable: Acidic | Aspartic Acid |
|  | Glutamic Acid |
| Ionizable: Basic | Arginine |
|  | Histidine |
|  | Lysine |
| Nonionizable Polar | Asparagine |
|  | Glutamine |
|  | Selenocystine |
|  | Serine |
|  | Threonine |

TABLE A-continued

| Conservative Amino Acid Substitutions | |
|---|---|
| Nonpolar (Hydrophobic) | Alanine |
|  | Glycine |
|  | Isoleucine |
|  | Leucine |
|  | Proline |
|  | Valine |
| Sulfur Containing | Cysteine |
|  | Methionine |

Of course, the number of amino acid substitutions a skilled artisan would make depends on many factors, including those described above. Generally speaking, the number of amino acid substitutions for any given filovirus polypeptide will not be more than 50, 40, 30, 20, 10, 5 or 3.

Amino acids in the filovirus polypeptides of the present invention that are essential for function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as receptor binding activity, connection between GP1 and GP2, and contribution to the formation of the stalk structure of the virion peplomer, and modified GP polypeptide activity by decrease of in vitro cytotoxicity while retaining immunogenicity.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus polypeptide can be substantially purified by the one-step method described in Smith and Johnson 1988 *Gene* 67:31-40.

The polypeptides of the present invention include a polypeptide comprising a polypeptide having the amino acid sequence of a modified filovirus structural gene product or portion thereof or encoded by a nucleic acid sequence described herein; as well as polypeptides which are at least 95% identical, and more preferably at least 96%, 97%, 98%, or 99% identical to those described above and also include portions of such polypeptides with at least 30 amino acids and more preferably at least 50 amino acids.

By a polypeptide having an amino acid sequence at least, for example, 95% "identical" to a reference amino acid sequence of an filovirus polypeptide is intended that the amino acid sequence of the polypeptide is identical to the reference sequence except that the polypeptide sequence may include up to five amino acid alterations per each 100 amino acids of the reference amino acid of the filovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides portions of the polypeptides described herein with at least 30 amino acids and more preferably at least 50 amino acids. Preferred portions of the present invention include polypeptides comprising an epitope-bearing portion of a filovirus structural protein. In particular, preferred portions of the present invention include polypeptides comprising an epitope-bearing domain of a filovirus structural protein, where the domain is the N-terminal domain, the mucin-like domain, the furin cleavage site, the fusion peptide domain, the coiled-coil domain, the membrane-spanning domain, and the intracellular domain, and any combination thereof, for example, a filovirus glycoprotein having a truncation at the carboxy terminus to delete the membrane spanning and intracellular domain, a filovirus glycoprotein having a truncation at the carboxy terminus to delete the coiled-coil domain and membrane spanning and intracellular domain, a filovirus glycoprotein having a truncation at the carboxy terminus to delete the fusion peptide domain, coiled-coil domain, and membrane-spanning and intracellular domain, a filovirus glycoprotein having a truncation at the carboxy terminus to delete the furin cleavage site, fusion peptide domain, coiled-coil domain, and membrane-spanning and intracellular domain, and a filovirus glycoprotein having a truncation at the carboxy terminus to delete the mucin-like domain, furin cleavage site, fusion peptide domain, coiled-coil domain, and membrane-spanning and intracellular domain. Another example is a filovirus glycoprotein having an amino, internal, or carboxy deletion to delete the mucin-like domain, the furin cleavage site, the fusion peptide domain, the coiled-coil domain, the membrane-spanning domain, or the intracellular domain.

The polypeptides of the invention may be produced by any conventional means (Houghten, R. A. 1985 *PNAS USA* 82:5131-5135). The "Simultaneous Multiple Peptide Synthesis (SMPS)" process is described in U.S. Pat. No. 4,631,211 to Houghten et al. (1986).

The present invention also relates to vectors which include the nucleic acid molecules of the present invention, host cells which are genetically engineered with the recombinant vectors, and the production of filovirus polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells Appropriate culture mediums and conditions for the above-described host cells are known in the art.

Among vectors preferred for use in bacteria include pQE70, pQE60, and pQE-9, available from Qiagen; pBS vectors, Phagescript vectors, Bluescript vectors, pNH8A, pNH16a, pHN18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The filovirus polypeptides can be recovered and purified from recombinant cell cultures by well known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Antibodies

Also comprehended by the present invention are antibodies (e.g., monoclonal and polyclonal antibodies, single chain antibodies, chimeric antibodies, humanized, human, and CDR-grafted antibodies, including compounds which include CDR sequences which specifically recognize a polypeptide of the invention) and other binding proteins specific for filovirus GP polypeptides or fragments thereof. The term "specific for" indicates that the variable regions of the antibodies of the invention recognize and bind a filovirus GP polypeptide exclusively (i.e., are able to distinguish a filovirus GP polypeptide from related polypeptides despite sequence identity, homology, or similarity found in the family of polypeptides), but may also interact with other proteins through interactions with sequences outside the variable region of the antibodies, and in particular, in the constant region of the molecule. Screening assays to determine binding specificity of an antibody of the invention are well known and routinely practiced in the art. For a comprehensive discussion of such assays, see *Antibodies A Laboratory Manual*, Harlow et al. (Eds), Cold Spring Harbor Laboratory; Cold Spring Harbor, N.Y. (1988), Chapter 6. Antibodies that recognize and bind fragments of the filovirus GP polypeptides of the invention arm also contemplated, provided that the antibodies are first and foremost specific for, as defined above, a filovirus GP polypeptide of the invention from which the fragment was derived. The specific antibodies of the invention are envisioned as having utility for diagnostic purposes and passive immunization.

Use of Recombinant Virus to Induce Immune Response to Antigen

The present invention relates to generation of a CD8+ T cell immune response against an antigen and also eliciting an antibody response. More particularly, the present invention relates to "accelerated" immunization regimes in which the immune response is induced by administration of a single dose form and "prime and boost" immunization regimes in which the immune response induced by administration of a priming composition is boosted by administration of a boosting composition. The present invention, in one embodiment, is based on the inventors' experimental demonstration that effective immunization can be achieved using recombinant virus, e.g., adenovirus, optionally as boosting compositions following priming with any of a variety of different types of priming compositions.

A major protective component of the immune response against a number of pathogens is mediated by T lymphocytes of the CD8+ type, also known as cytotoxic T lymphocytes (CTL). An important function of CD8+ cells is secretion of gamma interferon (IFNγ), and this provides a measure of CD8+ T cell immune response. A second component of the immune response is antibody directed to the proteins of the pathogen.

The present invention, in one embodiment, employs recombinant virus, e.g., adenovirus, which, as the experiments described below show, has been found to be an effective means for inducing a CD8+ T cell immune response, optionally as a boosting composition primed by antigen using any of a variety of different priming compositions, and for eliciting an antibody response.

Replication-deficient adenovirus derived from human serotype 5 has been developed as a live viral vector by Graham and colleagues (Graham & Prevec 1995 *Mol Biotechnol* 3:207-20; Bett et al. 1994 *PNAS USA* 91:8802-6). Adenoviruses are non-enveloped viruses containing a linear double-stranded DNA genome of around 36 kb. Recombinant viruses can be constructed by in vitro recombination between an adenovirus genome plasmid and a shuttle vector containing the gene of interest together with a strong eukaryotic promoter, in a permissive cell line which allows viral replication. High viral titres can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens including tick-borne encephalitis virus NS1 protein (Jacobs et al. 1992 *J Virol* 66:2086-95) and measles virus nucleoprotein (Fooks et al. 1995 *Virology* 210:456-65).

Remarkably, the experimental work described below demonstrates that use of embodiments of the present invention allows for recombinant adenovirus expressing an antigen to induce an immune response, optionally as a boosting composition primed by a DNA vaccine. The adenovirus was found to induce an immune a CD8+ T cell and antibody response after intramuscular immunization. In prime/boost vaccination regimes the recombinant virus, e.g., adenovirus, is also envisioned as being able to prime an immune response that can be boosted by a different recombinant virus or recombinantly produced antigen.

Non-human primates immunized with recombinant virus, e.g., adenovirus, optionally as a boosting composition following priming with plasmid DNA were protected against challenge. Both recombinant adenovirus and plasmid DNA are vaccines that are safe for use in humans. Advantageously, the inventors found that a vaccination regime using single dose immunization, optionally prime and boost immunization, can be employed, constituting a general immunization regime suitable for inducing an immune response, e.g., in humans.

The present invention in various aspects and embodiments employs a recombinant virus, e.g., adenovirus, encoding an antigen for inducing an immune response to the antigen, optionally for boosting an immune response primed by previous administration of the antigen or nucleic acid encoding the antigen.

A general aspect of the present invention provides for the use of a recombinant virus, e.g., adenovirus, for inducing, optionally boosting an immune response to an antigen.

One aspect of the present invention provides a method of inducing, optionally boosting an immune response to an antigen in an individual, the method including provision in the individual of a recombinant virus, e.g., adenovirus, including nucleic acid encoding the antigen operably linked to regulatory sequences for production of antigen in the individual by expression from the nucleic acid, whereby an immune response to the antigen is induced or an immune response to the antigen previously primed in the individual is boosted.

An immune response to an antigen may be primed by plasmid DNA immunization, by infection with an infectious agent, or by development of a recombinantly produced antigen.

A further aspect of the invention provides a method of inducing an immune response to an antigen in an individual, the method comprising administering to the individual a single dose of composition comprising the antigen or nucleic acid encoding the antigen or a priming composition comprising the antigen or nucleic acid encoding the antigen and then administering a boosting composition which comprises a recombinant virus, e.g., adenovirus, including nucleic acid encoding the antigen operably linked to regulatory sequences for production of antigen in the individual by expression from the nucleic acid.

A further aspect provides for use of a recombinant virus, e.g., adenovirus, as disclosed, in the manufacture of a medicament for administration to a mammal to induce, optionally to boost an immune response to an antigen. Such a medicament is optionally for administration in single dose form or following prior administration of a priming composition comprising the antigen or nucleic acid encoding the antigen.

The inducing, boosting, or priming composition may comprise any viral vector, including adenoviral, or other than adenoviral, such as a vaccinia virus vector such as a replication-deficient strain such as modified virus Ankara (MVA) (Mayr et al. 1978 *Zentralbl Bakteriol* 167:375-90; Sutter and Moss 1992 *PNAS USA* 89:10847-51; Sutter et al. 1994 *Vaccine* 12:1032-40) or NYVAC (Tartaglia et al. 1992 *Virology* 118:217-32), an avipox vector such as fowlpox or canarypox, e.g., the strain known as ALVAC (Kanapox, Paoletti et al. 1994 *Dev Biol Stand* 82:65-9), a herpes virus vector, a vesicular stomatitis virus vector, or an alphavirus vector.

The inducing or priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular, prime and boost embodiments of the various aspects of the present invention, administration of a priming composition is followed by boosting with a boosting composition or first and second boosting compositions, the first and second boosting compositions being the same or different from one another. Still further boosting compositions may be employed without departing from the present invention. In one embodiment, a triple immunization regime employs DNA, then adenovirus as a first boosting composition, and then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be included in respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the recombinant virus, e.g., adenovirus, regulatory sequences for expression of the encoded antigen will include a promoter. By "promoter" is meant a sequence of nucleotides from which transportation may be initiated of DNA operably linked downstream (i.e., in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, enhancer sequences, marker genes, internal ribosome entry site (IRES) and other sequences may be included as appropriate, in accordance with the knowledge and practice of the ordinary person skilled in the art: see, for example, Molecular Cloning: a Laboratory Manual, 2nd edition, Sambrook et al. 1989 Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1994.

Suitable promoters for use in aspects and embodiments of the present invention include the cytomegalovirus immediate early (CMV IE) promoter, with or without intron A, and any other promoter that is active in mammalian cells.

Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-1, GcMAF, B-alethine, MPC-026, Adjuvax, CpG ODN, Betafectin, Alum, and MF59 (see Kim et al., 2000 *Vaccine* 18:597 and references therein).

Other contemplated adjuvants that may be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, and IL-12 or encoding nucleic acids therefore.

Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks.

Preferably, administration of single dose composition, boosting composition, or priming composition is intramuscular immunization.

Intramuscular administration of adenovirus vaccines or plasmid DNA may be achieved by using a needle to inject a suspension of the virus or plasmid DNA. An alternative is the use of a needless injection device to administer a virus or plasmid DNA suspension (using, e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus is a virus with an excellent safety record in human immunizations. The generation of recombinant viruses can be accomplished simply, and they can be manufactured reproducibly in large quantities. Intramuscular administration of recombinant adenovirus is therefore highly suitable for prophylactic or therapeutic vaccination of humans against diseases which can be controlled by an immune response.

The individual may have a disease or disorder such that delivery of the antigen and generation of an immune response to the antigen is of benefit or has a therapeutically beneficial effect.

Most likely, administration will have prophylactic aim to generate an immune response against a pathogen or disease before infection or development of symptoms.

Diseases and disorders that may be treated or prevented in accordance with the present invention include those in which an immune response may play a protective or therapeutic role.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

As noted, administration is preferably intradermal, subcutaneous or intramuscular.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able, to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A slow-release formulation may be employed.

Following production of adenoviral particles and optional formulation of such particles into compositions, the particles may be administered to an individual, particularly human or other primate.

Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

In one preferred regimen, DNA is administered (preferably intramuscularly) at a dose of 10 micrograms to 50 milligrams/injection, followed by adenovirus (preferably intramuscularly) at a dose of $5 \times 10^7$-$1 \times 10^{12}$ particles/injection.

The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against disease or pathogens.

Specific Modifications of Ebola GP Optimize Vaccine Efficacy in Nonhuman Primates To develop an optimal Ebola vaccine using rAd vectors, we first analyzed mutant forms of GP in which the transmembrane domain had been removed. Though we have previously reported that deletion of the mucin domain eliminates cytotoxicity (Yang, Z.-Y. et al. 2000 Nat Med 6:886-889), this deletion removes nearly 200 amino acids, eliminating many potential T- and B-cell epitopes. Previous data suggested that the in vitro cytopathic effects of GP may be mediated at or near the cell surface and require transmembrane anchoring of the protein (Sullivan, N. J. et al. 2005 J Virol 79:547-553; Takada, A. et al. 2000 Virology 278:20-26; Chan, S. Y. et al. 2000 J Gen Virol 81:2155-2159). An alternative approach to the elimination of the GP-induced cytopathic effects was therefore explored by removal of the 26 amino acid putative transmembrane and cytoplasmic domains.

Figure 10A:
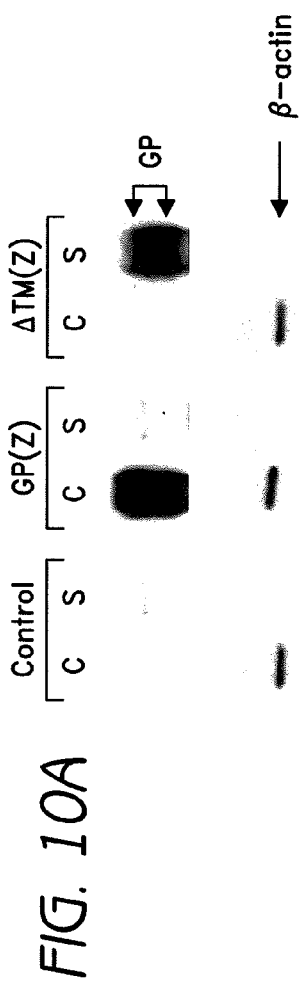
FIG. 10. Elimination of GP cytopathic effects and expression of transmembrane-deleted protein. A) Expression of GP(ΔTM) in 293 cells. Ebola GP proteins from supernatants and cell lysates in (A) were visualized by SDS-PAGE and Western blot using a polyclonal antibody against Ebola GP. B) Elimination of cell rounding by GP(ΔTM). 293 cells were transfected with a plasmid encoding vector control, Ebola GP or Ebola GP(ΔTM). Cell monolayers were visualized under phase contrast using a Nikon 40× objective and photographed at 24 hours post transfection.
Figure 10B:
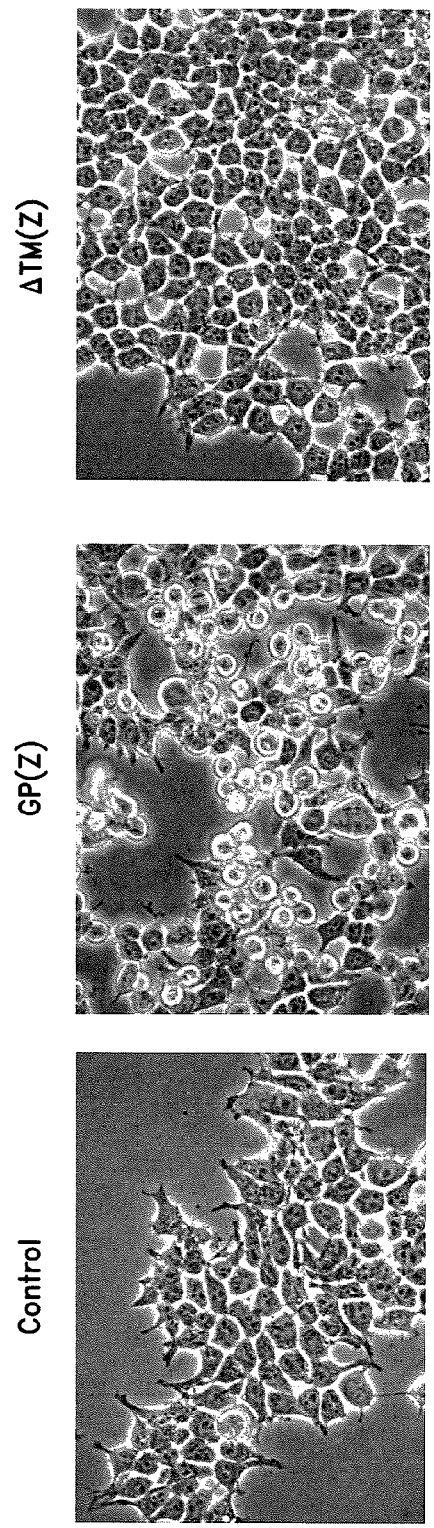
Figure 11A:
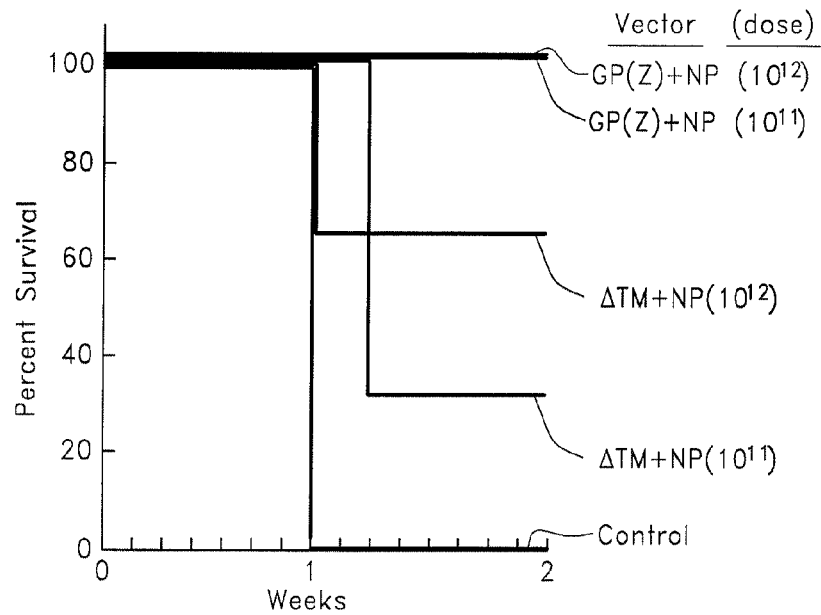
FIG. 11. Comparative efficacy of GP and GP(ΔTM) for protection against Ebola virus challenge. A) Kaplan-Meier survival curve of macaques, immunized as indicated, and challenged with 1000 PFU of Ebola virus (1995 Zaire subtype) one month post immunization. The x-axis indicates weeks post-challenge. n=3 in different immunization groups except for the GP(Z)+NP ($10^{12}$) group, n=4, and Control, n=1. B) Immune responses in immunized animals. Left and middle panels: intracellular flow cytometry was performed to quantify TNF-α production from Ebola-specific CD4$^+$ or CD8$^+$ lymphocytes, respectively, from animals immunized as indicated. Immune responses were measured at 3 weeks post-immunization. Circle, diamond, square, triangle: responses for individual animals. Horizontal line: average of individual responses in the immunization group. Results represent the percent cytokine positive in the gated lymphocyte group and background stimulation (DMSO alone) has been subtracted from each sample. Right panel: ELISA titers of Ebola GP-specific antibodies in serum of vaccinated animals collected at week 3 post-immunization. ELISA results represent endpoint dilution titers determined by optical density as described in Example 1.
Figure 11B:
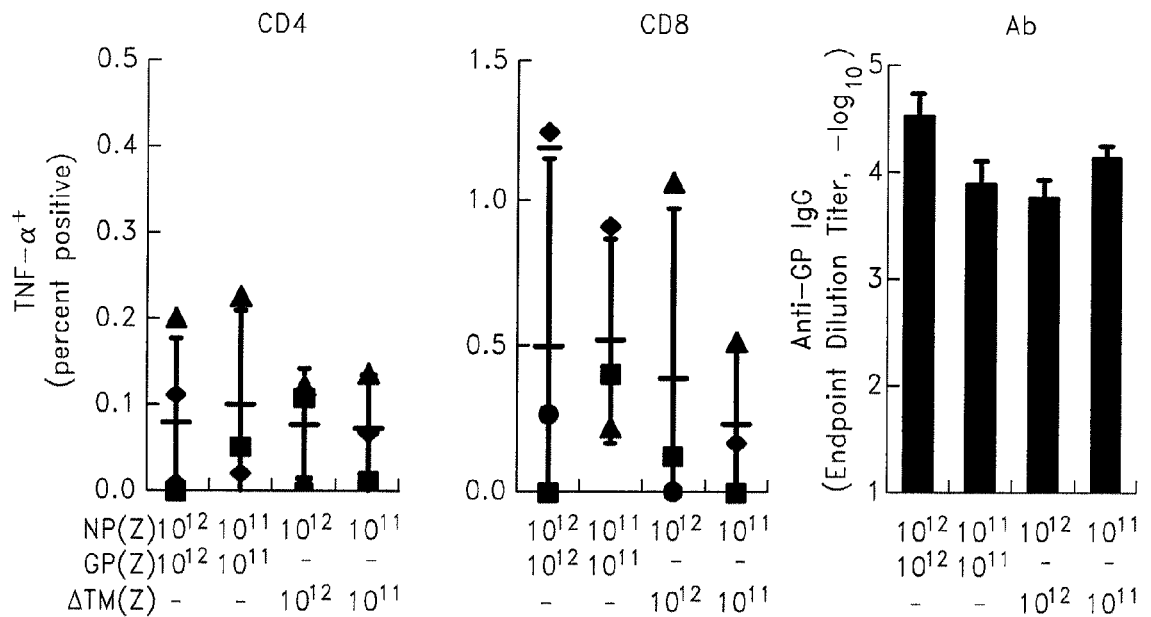

Diminished Immune Protection of a Mutant GP Lacking a Transmembrane Anchor Domain GP protein was readily detected in the supernatants of cells transfected with the transmembrane-deleted vector $\Delta$TM(Z), confirming its secretion, in contrast to supernatants from cells transfected with the wild type GP(Z) (FIG. 10A). Furthermore, synthesis of the two previously defined forms of GP, generated by post-translational processing (Volchkov, V. E. et al. 1995 Virology 214:421-430; Sanchez, A. et al. 1998 J Virol 72:6442-6447), was readily detected at comparable levels. Deletion of the transmembrane domain eliminated GP-induced cytopathicity in transfected 293 cells in contrast to wild type GP (FIG. 10B), but total $\Delta$TM expression was equivalent to wild type protein levels (FIG. 10A). To determine whether the $\Delta$TM mutant of the Zaire strain could protect against infectious Ebola challenge, cynomolgus macaques were immunized with rAd vectors encoding NP and either $\Delta$TM (Z), or GP(Z). Immunization with GP(Z)+NP protected all animals vaccinated with either $10^{11}$ or $10^{12}$ adenoviral particles and challenged with 1000 pfu of the Zaire strain of Ebola virus 28 days later (FIG. 11A). In contrast, survival frequencies decreased in animals receiving the $\Delta$TM(Z) vaccine. In the group vaccinated with $10^{12}$ adenoviral particles, protective immunity was decreased by 33% and at $10^{11}$, by 66%, indicating a substantial decrease in efficacy in animals vaccinated with $\Delta$TM+NP vs GP+NP (p<0.05). In a separate experiment, $10^{11}$ particles of $\Delta$TM alone failed to protect against infection. Analysis of cell-mediated immune responses showed that CD4$^+$ and CD8$^+$ T-cell responses were present in the majority of animals by 3 weeks post-immunization (FIG. 11B, left and middle panels, respectively) and did not correlate with the differences in survival: antigen specific cellular responses measured by intracellular cytokine (TNF-$\alpha$) secretion were indistinguishable between GP(Z)- and $\Delta$TM(Z)-vaccinated animals. Similarly, humoral immune responses measured by anti-Ebola GP ELISA IgG titers were comparable in all vaccinated animals (FIG. 11B, right panel). Neutralizing antibody titers were low, and were absent in some surviving animals. These results suggested that deletion of the GP transmembrane domain reduces vaccine efficacy, with no readily apparent correlates of protection.

Figure 12A:
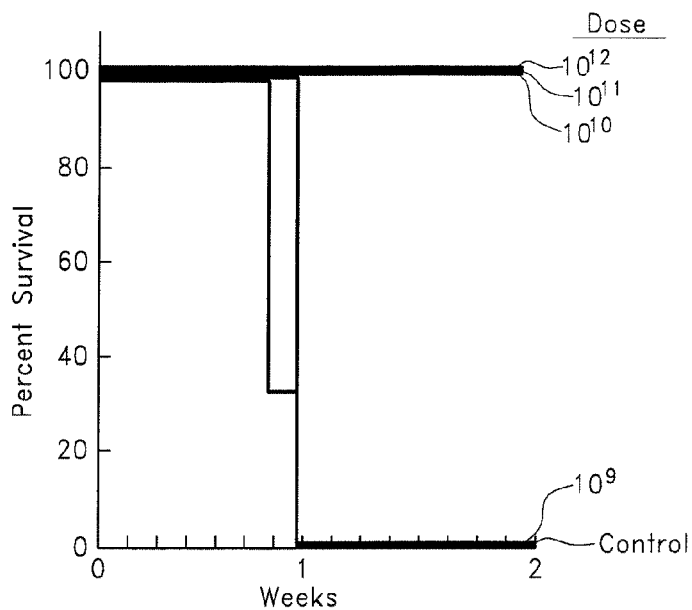
FIG. 12. Determination of lowest vaccine dose for immune protection against Ebola virus challenge by adenoviral vector vaccine. A) Kaplan-Meier survival curve of macaques: immunization and challenge were performed with the 1995 Zaire subtype Ebola virus as in FIG. 11A. B) Immune responses in immunized animals. Intracellular flow cytometry was performed to quantify TNF-α production from Ebola-specific CD4 (left panel) or CD8 (right panel) lymphocytes, respectively, from animals immunized as indicated. Immune responses were measured at 3 weeks post-immunization. Circle, diamond, square: responses for individual animals. Horizontal line: average of individual responses in the immunization group. Results represent the percent cytokine positive in the gated lymphocyte group and background stimulation (DMSO alone) has been subtracted from each sample (p-values obtained using unpaired Student's t-test. n.s.=not significant). C) Antibody responses in immunized animals. Anti-GP ELISA titers (left panel) and serum neutralizing antibody responses (right panel) were measured as described in Example 1.
Figure 12B:
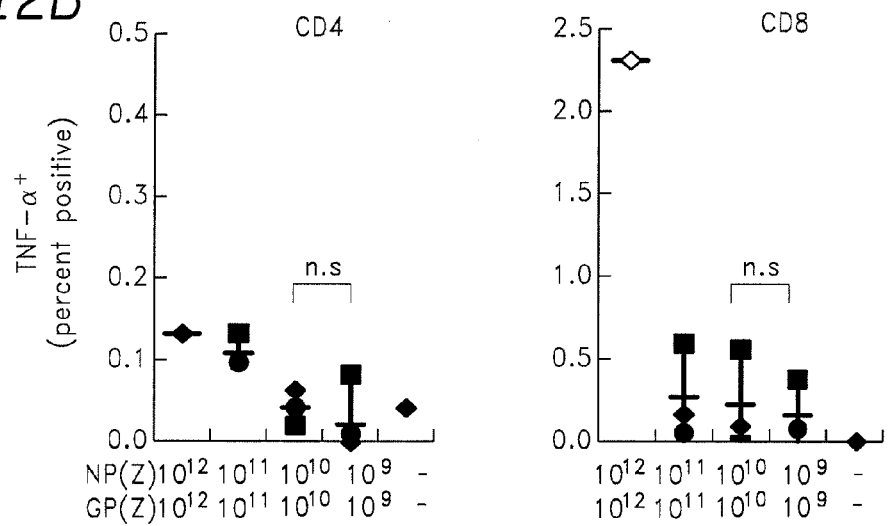
Figure 12C:
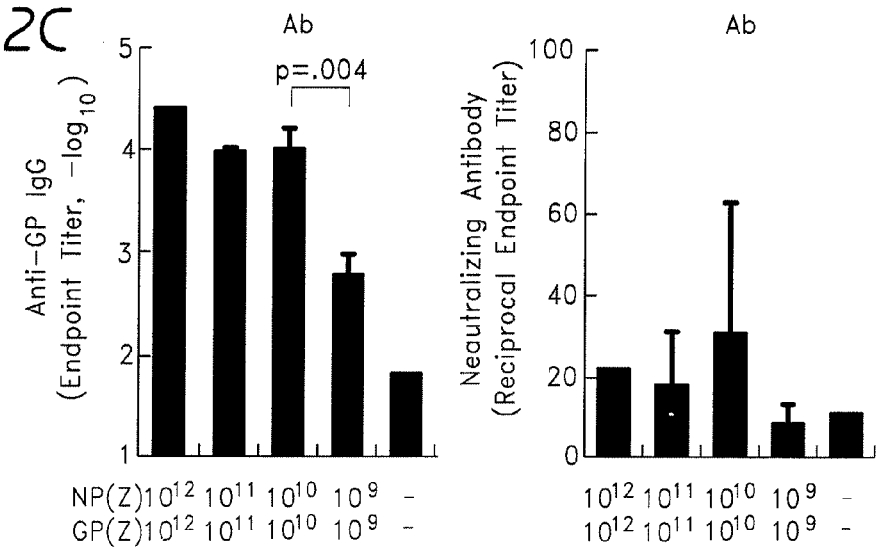
Figure 15:
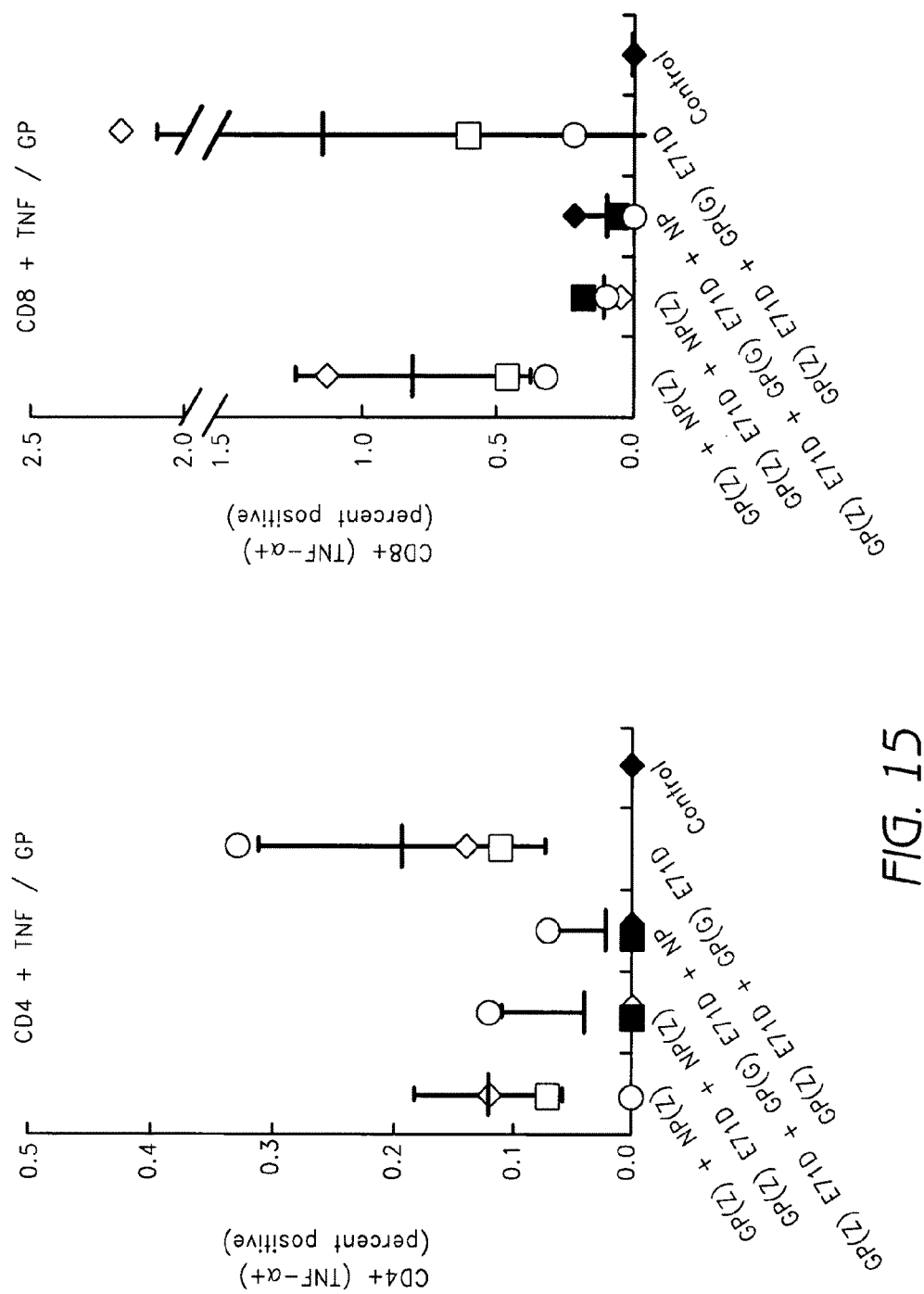
FIG. 15. Cellular immune responses generated in NHP immunized with GP(Z) E71D/NP.
Figure 16:
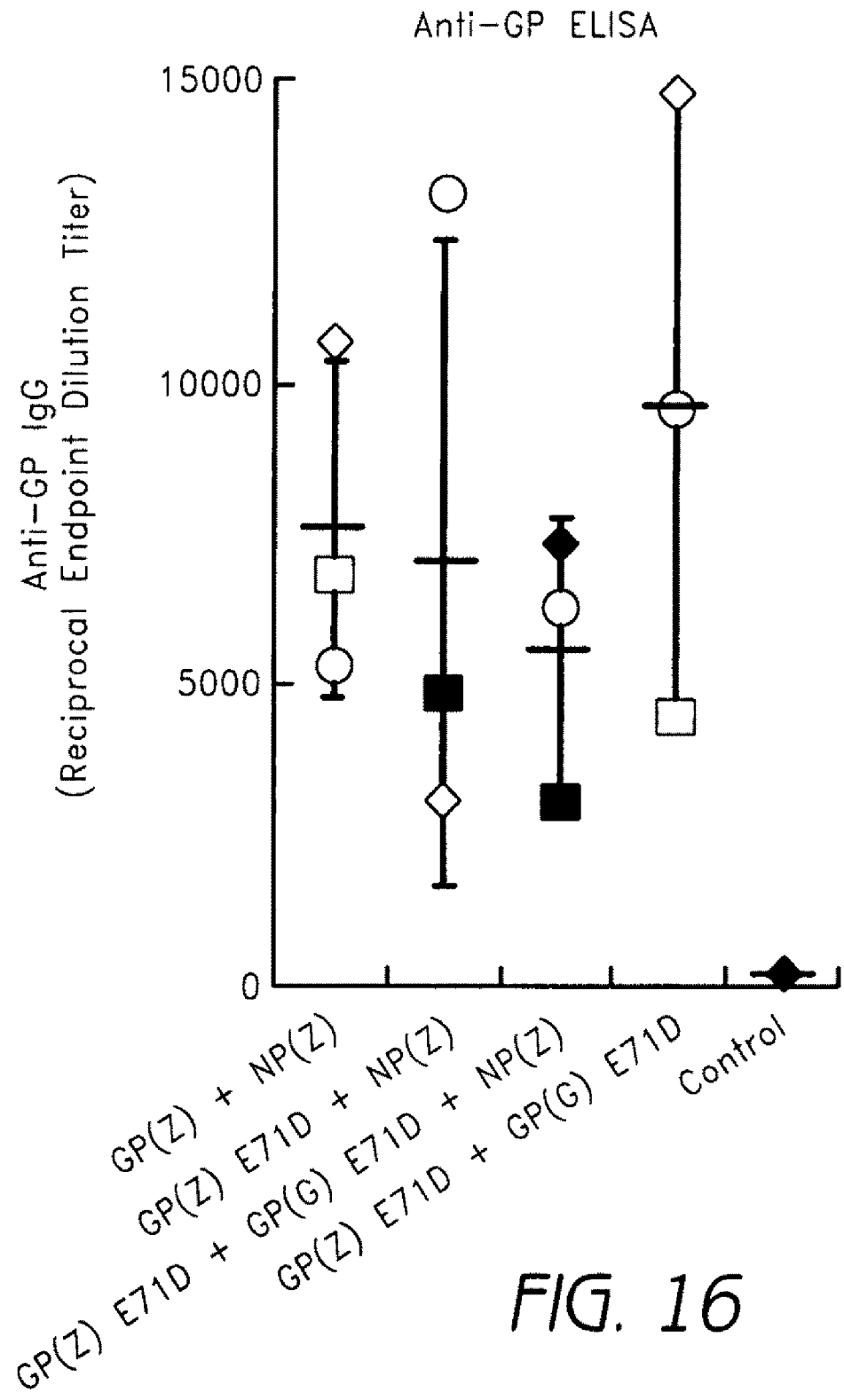
FIG. 16. Humoral immune responses generated in NHP immunized with GP(Z) E71D/NP.
Figure 18:
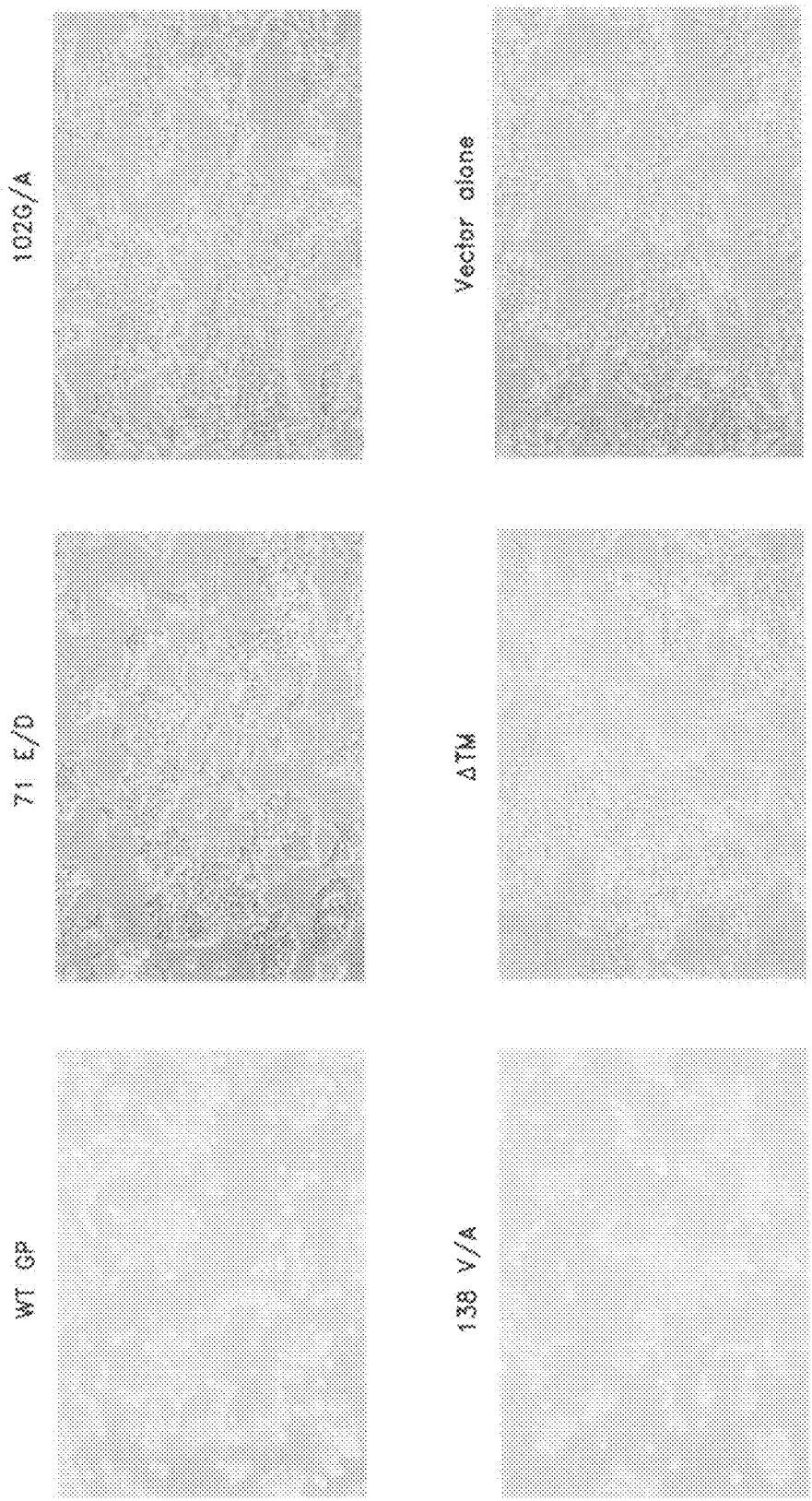
FIG. 18. Elimination of GP cytopathic effects with single point mutation. Elimination of cell rounding by amino acid substitution at position 71 or 102. 293 cells were transfected with a plasmid encoding vector control, wildtype Ebola Zaire glycoprotein, WT GP, or point mutations 71E/D, 102G/A, 138V/A or a mutation in which the transmembrane domain is deleted, ΔTM. Cell monolayers were visualized under phase contrast using a Nikon 40× objective and photographed at. 24 hours post transfection. Cell rounding is eliminated with mutation at residue 71 or 102, and with transmembrane deletion.
Figure 19:
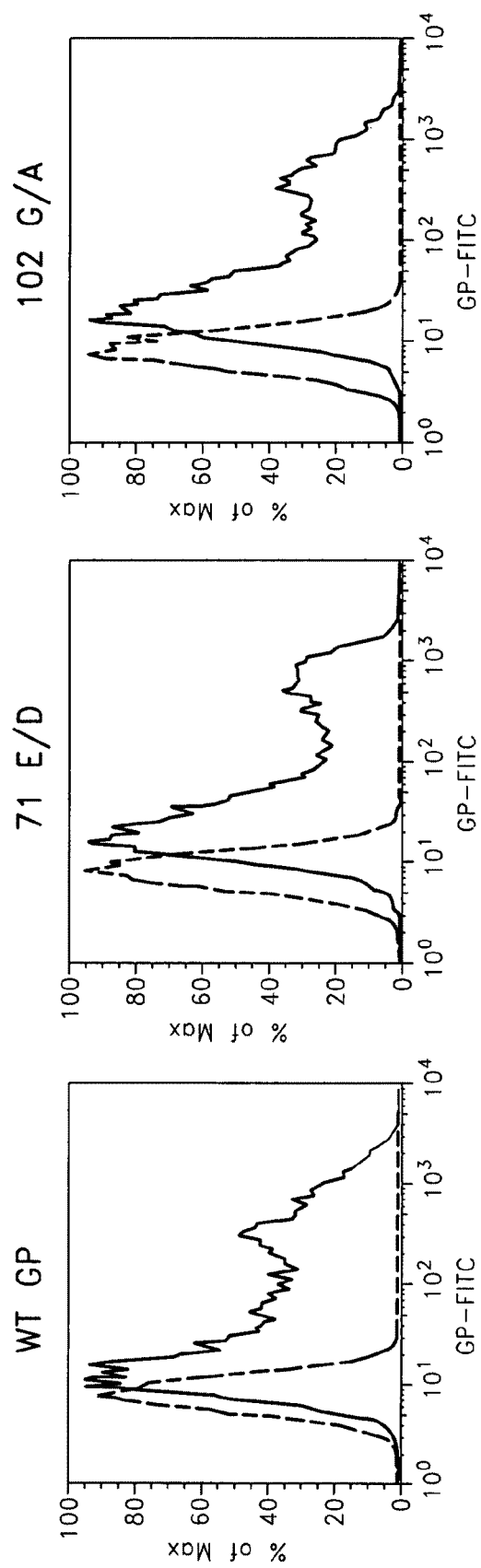
FIG. 19. Single point mutation in GP and retention of reactivity with neutralizing antibodies. Reactivity of point mutants with a conformation-dependent antibody. 293 cells were transfected with a control plasmid, dashed line, or plasmids expressing wildtype Ebola GP (WT GP) or mutant (71E/D 102G/A), solid line, proteins. Eighteen hours post transfection, cells were harvested, stained with a GP-specific neutralizing antibody and cell surface GP expression was analyzed by flow cytometry.

Definition of Minimal Protective Vaccine Dose for Protection with a rAd Vaccine Encoding GP and NP In the previous experiment, a log decrease in dose of the GP(Z)+NP vaccine was protective, in comparison to previous studies using $10^{12}$ rAd particles. To establish the lowest dose of adenoviral vectors that would afford protection against Ebola infection, a dose-response analysis was performed. Animals were immunized with rAd vectors encoding GP(Z) and NP at increasing doses from $10^9$ to $10^{12}$ particles per animal. Survival was 100% in all groups receiving a dose of $10^{10}$ or greater, whereas challenge infection was uniformly lethal in the $10^9$ dose group (FIG. 12A). Virus isolation by plaque assay on Vero cells was negative for all surviving animals. Pre-challenge CD4+ T-cell responses for TNF-α were unremarkable as reported previously for immunized cynomolgus macaques (FIG. 12B). CD8+ T-cell responses were similar across vaccine dose groups, except for the higher responder immunized at $10^{12}$ rAd particles. Antigen-specific IgG was also generated in immunized animals, and the levels were equivalent among animals in the groups that survived Ebola virus challenge (FIG. 12C, left). However, there was a difference in more than one log (p=0.004) in IgG levels between survivors immunized at $10^{10}$ and fatalities immunized at $10^9$ rAd particles, suggesting that such levels may correlate with protection for this immunization regimen. Neutralizing antibody titers against GP did not differ significantly between survivors and fatalities (FIG. 12C, right). These results indicated that the threshold for immune protection lies at about ~$10^{10}$ rAd particles. Therefore, subsequent experiments were carried out using this dose to increase sensitivity to detect differences in antigenic strength between various immunogens.

Identification of GP Point Mutants with Diminished in Vitro Cytotoxicity that Confer Effective Immune Protection We sought to identify other mutants of GP that do not exhibit cytopathic effects yet retain native antigenic structures when expressed in vitro. Relatively conserved regions of GP were identified, and point mutations were systematically introduced. GP proteins bearing single amino acid changes were screened for decreased induction of cell rounding but wild type levels of expression and reactivity with conformation-dependent antibodies. Substitution of aspartic for glutamic acid at position 71 in Ebola GP from the Zaire or Sudan/Gulu subtypes (E71D(Z), E71D(S/G), respectively) abolished the cell rounding phenotype in transfected 293 cells but did not alter protein expression or reactivity with antibodies whose binding properties are sensitive to changes in protein conformation (FIG. 14).

Figures 13A, 13B:
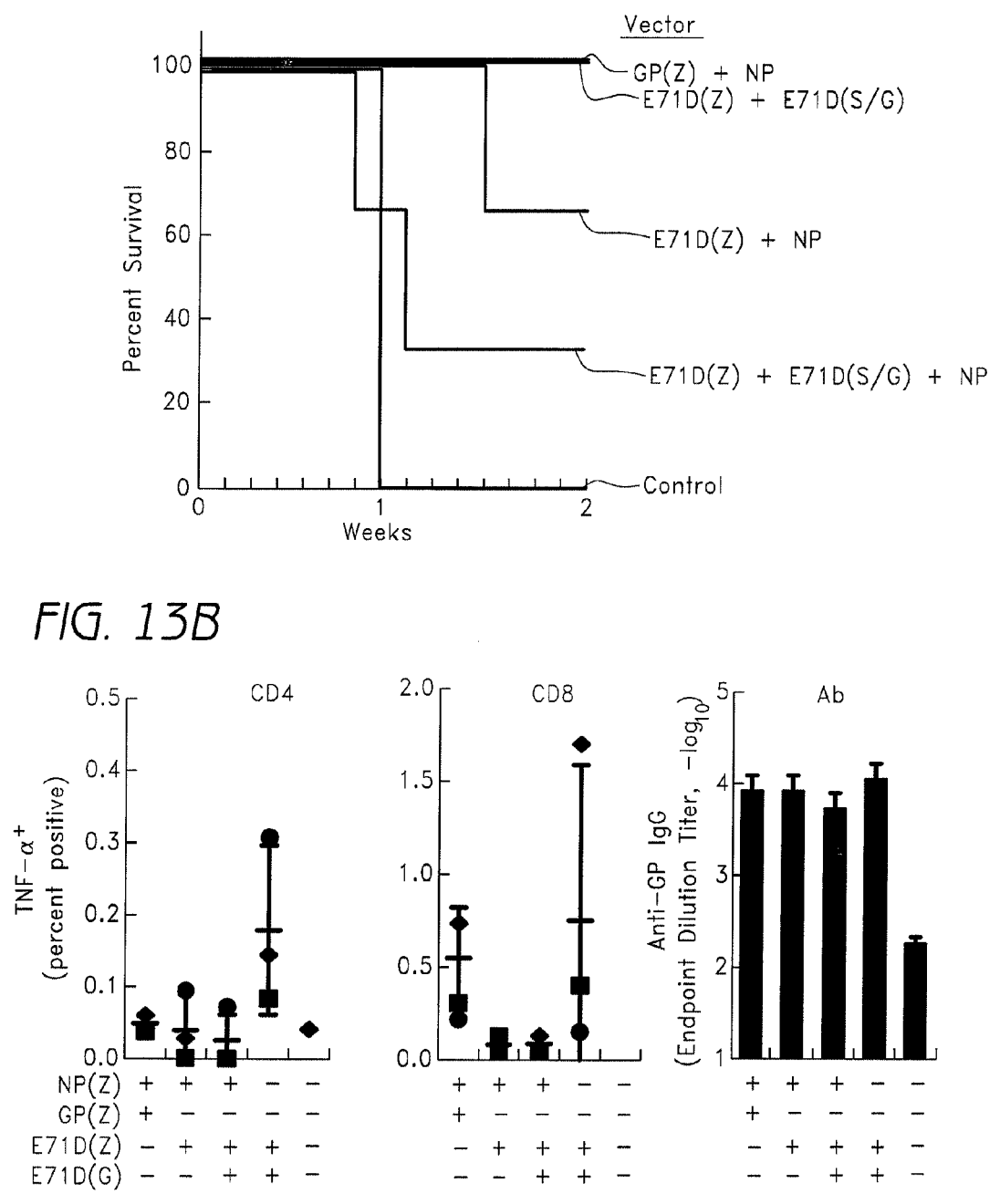

The E71D mutants were evaluated for their ability to induce protective immunity alone or in combination with NP. When E71D from Zaire and Sudan-Gulu were combined with NP, survival of cynomolgus macaques immunized in these groups was diminished by 33% and 66%, respectively (FIG. 13A). In contrast, complete protection was achieved in animals immunized with E71D(Z) and E71D(S/G), as it was in animals receiving wild type GP(Z) plus NP. Ebola GP-specific responses in T-lymphocytes detected by intracellular staining of TNF-α did not show statistically significant differences in the CD4+ population between different immunization groups (FIG. 13B, left panel). Similarly, individual differences in the CD8+ response did not correlate with survival, though there was a trend toward diminished survival in groups with lower antigen-specific CD8+ cellular responses (FIG. 13B, middle panel. Antigen-specific ELISA IgG was also stimulated in all immunized animals (FIG. 13B, right panel). The results of this experiment illustrate that NP may not be necessary for protective immunity against Ebola infection and that it may diminish protection when combined with modified GP immunogens at the lower limits of protective vaccine doses.

Ebola virus outbreaks are associated with high lethality due to the absence of treatment options or a licensed vaccine. Both DNA priming and rAd vector boosting, as well as rAd alone can confer protection to lethal challenge in an animal model that closely parallels human disease (Geisbert, T. W. et al. 2003 *Am J Pathol* 163:2347-2370). The rAd vector vaccine conferred protection in an accelerated vaccine regimen in nonhuman primates (Sullivan, N. J. et al. 2003 *Nature* 424: 681-684). Although in vitro cytopathicity has been observed by over expression of Ebola GP, one of the vaccine components, we have not seen toxicity in animals vaccinated by vectors expressing Ebola GP. However, because this hypothetical complication has been raised, we sought to modify GP to eliminate in vitro cytopathicity yet retain antigenic properties that are necessary for protective immunity. Here, the efficacies of different forms of GP were evaluated using doses at the threshold of protection in the accelerated vaccination model. We have identified a vaccine with decreased in vitro cytopathicity that retained immunogenicity necessary to protect against Ebola infection.

We find that alternative forms of GP confer differential immune protection. Deletion of the GP transmembrane domain abolished cytopathic effects in transfected 293 cells, but the corresponding ΔTM(Z) vaccine was less efficacious than wild type GP(Z) in protecting nonhuman primates against infection. Though cellular and humoral immune responses were indistinguishable between groups receiving the different immunogen forms, the inherent variability in quantitating the responses in outbred macaques may obscure our ability to identify immune responses responsible for higher survival. Alternatively, ΔTM(Z) may differ from wild type GP(Z) in antigenic qualities that are not captured by measurements of total antigen-specific IgG or intracellular cytokine responses stimulated by a broad peptide pool. For example, the transmembrane-deleted protein is secreted and likely shows conformational differences from the membrane anchored protein. Subsequent modifications of the glycoprotein to retain membrane attachment and a more native envelope structure yielded a mutant, E71D, with reduced in vitro cytopathicity. Recently, it has been suggested that this region of GP contributes to viral receptor binding (Manicassamy, B. et al. 2005 *J Virol* 79:4793-4805). It is noteworthy that the envelope glycoprotein cytopathicity of other viruses such as HIV is linked to receptor binding and fusion (Cao, J. et al. 1996 *J Virol* 70:1340-1354), raising the possibility that Ebola GP shares similar properties.

Ongoing outbreaks of both Ebola and Marburg viruses illustrate the importance of developing a filovirus vaccine for human use. This report shows that protective immunity against Ebola infection is achieved in nonhuman primates by the generation of antigen-specific immune responses to a single protein, GP, which has been modified to eliminate in vitro cytopathic effects. The accelerated vaccine strategy has since been repeated using vesicular stomatitis virus (VSV) vectors (Jones S. M. et al. 2005 *Nat Med*, published online Jun. 5, 2005), validating the promise of vaccines for Ebola. However, there are concerns about the use of VSV as a human vaccine because it is replication-competent and derives from a virus that is pathogenic in animals. In contrast, the rAd vector vaccine is non-replicating, can be manufactured to high yields, and safety data exist for this platform. Immunity follows a single injection with $10^{10}$ rAd particles, a dose that is two orders of magnitude lower than previously reported for this single modality vaccine. Such doses of rAd vectors have proven to be well-tolerated and immunogenic for other recombinant genes in vivo and can be evaluated for the vectors reported here, alone or in DNA prime/rAd boost combinations. Immunization with $10^{10}$ rAd particles of E71D(Z)+E71D(S/G) was effective against infectious challenge with Ebola Zaire, and protection did not require NP. Elimination of NP from the vaccine and dose reductions to $10^{10}$ rAd particles do not diminish protection and simplify the vaccine for future development in human trials.

EXAMPLE 1

Vector Construction and Transfections

E1/E3-deleted, replication-incompetent Ad5 vectors were generated in PER.C6® cells (Fallaux, F. J. et al. 1998 *Hum Gene Ther* 9:1909-1917) using a pBR322-based adaptor plasmid pAdApt together with cosmid pWE.Ad.AflII-rITRΔE3 essentially as described elsewhere (Havenga, M. J. et al. 2001 *J Virol* 75:3335-3342). The adaptor plasmid contained the left portion of the Ad5 genome (nucleotides 1-454), followed by transcriptional control elements and the adaptor Ad5 DNA region (nucleotides 3511-6095 in Ad5). Ebola GP encoding genes were cloned into the expression cassette in the adaptor plasmids under transcriptional control of the human full-length immediate-early CMV promoter and the SV40 polyadenylation signal. Adenoviruses containing Ebola GP, GPΔTM, and point mutations were generated by cotransfection of linearized pAdApt-Ebola GP plasmids together with the linearized cosmid pWE.Ad.AflII-rITRΔE3 containing the right portion of the Ad5 genome to PER.C6® cells using Lipofectamine (Invitrogen). PER.C6® cells were cultured in DMEM supplemented with 10% fetal bovine serum (GIBCO) and incubated at 37° C. under humified atmosphere and 10% $CO_2$. Homologous recombination led to the generation of rAd5-Ebola GP viruses. Adenoviral vectors in crude lysates were plaque purified using limiting dilutions and agar overlays, and Ad vector clones were analyzed for presence and expression of the transgene. Positive clones were amplified for large-scale production using PER.C6® cells in 48 triple-layer 3×175 $cm^2$ flasks. Viruses were purified by standard two-step CsCl gradient ultracentrifugation and subsequently desalted and formulated by three consecutive dialysis steps into TRIS-Cl pH 8.0 containing 2.5% glycerol. Purified Ad vectors were stored as single use aliquots at –80° C. Virus particle (vp) titers were determined by anion-exchange high-performance liquid chromatography based on described procedures (Shabram, P. W. et al. 1997 *Hum Gene Ther* 8:453-465). Infectivity was assessed by TCID50 using 911 cells. Ebola GP expression was assessed by infection of A549 cells followed by analysis of culture lysates on western blot. The identity of the purified vectors was confirmed by PCR. Expression vectors p1012, pGP and pΔTM and point mutants contain a CMV enhancer promoter that have been described previously (Sullivan, N. J. et al. 2000 *Nature* 408:605-609). The pΔTM contains a deletion from amino acid 651 to 676 and was created by digesting with BspMI/Kenow, and then fusing to TGA. The resulting plasmid also contained four extra amino acids at the C-terminus (MAAS). 293 human embryonal kidney cells were cultured in DMEM supplemented with 10% fetal bovine serum (GIBCO). Transfections to measure protein expression and cell rounding were performed in 293 cells with 2 µg DNA per well of a 6-well plate using calcium phosphate (Invitrogen) according to the manufacturer's instructions. Protein expression was evaluated by SDS-PAGE followed by Western blot with a GP-specific antibody kindly provided by A. Sanchez.

Animal Study and Safety

Cynomolgus macaques (*M. fascicularis*), 3-5 years old and weighing 2-3 kg, obtained from Covance, were used for immunization and challenge experiments. The monkeys, housed singly, were anesthetized with ketamine to obtain blood specimens and to administer vaccines. In conducting this research, the investigators adhered to the *Guide for the Care and Use of Laboratory Animals*, prepared by the Institute of Laboratory Animal Resources, National Research Council (National Academy Press, Washington, D.C., 1996). The facilities are fully accredited the Association for Assessment and Accreditation of Laboratory Animal Care International. They received regular enrichment according to the Guide for the Care and Use of Laboratory Animals (DHEW No. NIH 86-23). Before Ebola virus challenge and to the end of each experiment, the animals were maintained in the Maximum Containment Laboratory (BSL-4) and fed and checked daily.

Macaque Immunization and Challenge

Cynomolgus macaques were injected intramuscularly with a 1.0 ml equal mixture of immunogens at the doses indicated. Viral challenge was performed by inoculation of animals in the left or right caudal thigh with 0.5 ml of viral stock that contained a target dose of ~1000 PFU EBOV (Zaire species) at four weeks after the initial immunization. No adverse effects of the adenovirus vaccination were observed acutely. The Ebola virus used in this study was originally obtained from a fatally infected human from the former Zaire in 1995 (Jahrling, P. B. et al. 1996 *Arch Virol Suppl* 11:135-140). Collection of serum and blood for viral load and ELISA titers was performed as previously described (Sullivan, N. J. et al. 2000 *Nature* 408:605-609).

Flow Cytometry and Antibodies

Transfected cells were collected after incubation with PBS (3 mM EDTA) and incubated with control Ig or rabbit anti-sGP/GP serum (generously provided by Dr. A. Sanchez) for 30 minutes on ice. The cells were washed twice with ice-cold PBS containing 2.5% fetal bovine serum, incubated with FITC- or PE-conjugated secondary antibodies (Jackson ImmunoResearch Laboratories and Sigma, respectively) for 30 minutes on ice, followed by washing. Analysis was conducted using a Becton Dickinson 4-color Calibur flow cytometer and FlowJo analysis software (Tree Star, Inc).

ELISA

Nunc-Immuno Maxisorp plates (Nunc, Rochester, N.Y.) were coated with Ebola GP from 293 cell supernatants and incubated at 4° C. until use. All further incubations were carried out at room temperature. Plates were then washed six times with PBS containing Tween 20. Test sera were diluted in PBS containing Tween 20 and 1% fetal calf serum and allowed to react with the Ag-coated wells for 60 minutes. After washing plates six times, goat anti-human IgG (H+L; Chemicon, Temecula, Calif.) conjugated to horseradish peroxidase was used as a detection antibody. Bound IgG was detected by Sigma Fast o-Phenylenediamine Dihydrochloride Tablet Sets (Sigma-Aldrich, St. Louis, Mo.) and the optical density was determined. A panel of normal sera was run each time the assay was performed.

Neutralizing Antibody Analysis

Ebola GP(Z) pseudotyped lentiviral virions were produced as previously described (Yang, 2004 *J Virol* 78:5642-5650). Briefly, 293T cells were plated in 10-cm-diameter tissue culture dishes and transfected the next day by calcium phosphate reagent (Invitrogen) with pCMVΔR8.2, pHR'CMV-Luc and CMV/R Ebola GP(Z) plasmid DNA. Cells were transfected overnight, washed, and replenished with fresh medium. Forty-eight hours later, supernatants containing pseudotyped virus were harvested, filtered through a 0.45-µm-pore-size syringe filter, and stored in aliquots at –80° C. Neutralization assays were performed on HUVECs (Cambrex CC-2517) plated in a 24 well plate 1 day prior to infection. Virus stocks were incubated at 37° C. for 1 hour in the presence of serum from immunized cynomolgus macaques. The culture media was removed from the cells and replaced with the virus/serum media in the presence of polybrene (Sigma-Aldrich, 107689) at a final concentration of 5 ug/mL. 72 hours post infection cells were lysed and assayed by Luciferase Assay System (Promega, E1501/E1531). Luciferase activity was determined using a Veritas Microplate Luminometer from Turner Biosystems.

Intracellular Cytokine Analysis

Peripheral blood mononuclear cells (PBMC) were isolated from cynomolgus macaque whole blood samples by separation over Ficoll. Approximately $1\times10^6$ cells were stimulated in 200 µl RPMI medium (GIBCO) for 6 hours at 37° C. with anti-CD28 and -CD49d antibodies, brefeldin A, and either DMSO or a pool of 15-mer peptides spanning the Ebola GP Zaire (Mayinga strain) open reading frame. The peptides were 15-mers overlapping by 11 spanning the entire Ebola glycoprotein at a final concentration of 2 µg/ml. Cells were fixed and permeablized with FACS Lyse (Becton Dickinson) supplemented with Tween 20, and stained with a mixture of antibodies against lineage markers (CD3-PE, CD4-PerCP, CD8-FITC) and either TNF-APC. Samples were run on a FACS Calibur or FACS Aria and analyzed using the software FlowJo. Positive gating for lymphocytes using forward vs. side scatter was followed by $CD3^+/CD8^-$ and $CD3^+/CD4^-$ gating, and specific populations were further defined by anti-CD4 and anti-CD8 positivity, respectively. Cytokine positive cells were defined as a percentage within these individual lymphocyte subsets and at least 200,000 events were analyzed for each sample.

\*\*\*

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated nucleic acid molecule having SEQ ID NO:5.
2. An isolated plasmid DNA comprising a CMV immediate early enhancer promoter, an HTLV-1 R region and the Marburg/Angola GP/h insert of SEQ ID NO:5.
3. An isolated recombinant virus comprising the Marburg/Angola GP/h insert of SEQ ID NO:5.
4. An isolated adenovirus comprising the Marburg/Angola GP/h insert of SEQ ID NO:5.
5. An immunogenic composition comprising the nucleic acid molecule of claim 1 in a immunogenically effective dose.
6. A method of boosting an immune response to a Marburg virus antigen in a primate, the method comprising administration to the primate of the recombinant virus of claim 3, whereby an immune response to the antigen previously primed in the primate is boosted.
7. A method of inducing an immune response to a Marburg virus antigen in a primate, the method comprising administration to the primate of the nucleic acid molecule of claim 1, whereby an immune response to the antigen in the primate is induced.

8. A method of inducing an immune response to a Marburg virus antigen in a primate, the method comprising administration to the primate of a priming composition comprising the nucleic acid molecule of claim 1 and then administration to the primate of a boosting composition comprising the antigen or a recombinant virus encoding the antigen.

* * * * *

SEQUENCE LISTING

```
<160> NUMBER OF SEQ ID NOS: 9

<210> SEQ ID NO 1
<211> LENGTH: 6426
<212> TYPE: DNA
<213> ORGANISM: Ebola virus (Sudan, Gulu)

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc      480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960 tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atgagggcc tgagcctgct    1380
```

```
gcagctgccc agggacaagt tcaggaagag cagcttcttc gtgtgggtga tcatcctgtt    1440
ccagaaggcc ttcagcatgc ccctgggcgt ggtgaccaac agcaccctgg aggtgaccga    1500
gatcgaccag ctggtgtgca aggaccacct ggccagcacc gaccagctga gagcgtggg     1560 cctgaacctg gagggcagcg gcgtgagcac cgacatcccc agcgccacca agaggtgggg    1620
cttcaggagc ggcgtgcctc ccaaggtggt gagctacgag gccgccagt gggccgagaa     1680 ctgctacaac ctggagatca agaagcccga cggcagcgag tgcctgcctc ctcctcctga    1740
cggcgtgagg ggcttcccca ggtgcaggta cgtgcaagg gcccagggca ccggcccctg     1800
ccccggcgac tacgccttcc acaaggacgg cgccttcttc ctgtacgaca ggctggccag    1860
caccgtgatc tacaggggcg tgaacttcgc cgagggcgtg atcgccttcc tgatcctggc    1920
caagcccaag gagaccttcc tgcagagccc tcccatcagg gaggccgtga actacaccga    1980
gaacaccagc agctactacg ccaccagcta tctagagtac gagatcgaga acttcggcgc    2040
ccagcacagc accaccctgt tcaagatcga caacaacacc ttcgtgaggc tggacaggcc    2100
ccacacccct cagttcctgt tccagctgaa cgacaccatc cacctgcacc agcagctgag    2160
caacaccacc ggcaggctga tctggaccct ggacgccaac atcaacgccg acatcggcga    2220
gtgggccttc tgggagaaca agaagaacct gagcgagcag ctgaggggcg aggagctgag    2280
cttcgaggcc ctgagcctga cgagaccga ggacgacgac gccgccagca gcaggatcac     2340
caagggcagg atcagcgaca gggccaccag gaagtacagc gacctggtgc caagaacag     2400 ccccggcatg gtgcccctgc catccccga gggcgagacc accctgccca gcagaacag     2460 caccgagggc aggagggtgg gcgtgaacac ccaggagacc atcaccgaga ccgccgccac    2520
catcatcggc accaacggca accacatgca gatcagcacc atcggcatca ggcccagcag    2580
cagccagatc cccagcagca gccccaccac cgccccctag cccgaggccc agaccccac    2640 cacccacacc agcggaccca gcgtgatggc caccgaggag cccaccaccc ctcccggcag    2700
cagccccgga cccaccaccg aggcccctac cctgaccacc cctgagaaca tcaccaccgc    2760
cgtgaagacc gtgctgcccc aggagagcac cagcaacggc ctgatcacca gcaccgtgac    2820
cggcatcctg ggcagcctgg gcctgaggaa gaggagcagg aggcagacca acaccaaggc    2880
caccggcaag tgcaacccca acctgcacta ctggaccgcc caggagcagc acaacgccgc    2940
cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctacacca tcctgaacag    3120
gaaggccatc gacttcctgc tgaggaggtg gggcggcacc tgcaggattc tgggccccga    3180
ctgctgcatc gagccccacg actggaccaa gaacatcacc gacaagatca ccagatcat     3240 ccacgacttc atcgacaacc ctctgcccaa ccaggacaac gacgcacaact ggtggaccgg    3300 ctggcggcag tggataccctg ccggcatcgg catcaccggc atcatcatcg ccatcatcgc    3360
tctgctgtgc gtgtgcaagc tgctgtgctg agaattcaga tctacacgat ctgctgtgcc    3420
ttctagttgc cagccatctg ttgtttgccc ctccccgtg ccttccttga ccctggaagg     3480
tgccactccc actgtccttt cctaataaaa tgaggaaatt gcatcgcatt gtctgagtag    3540
gtgtcattct attctggggg gtggggtggg gcaggacagc aaggggagg attgggaaga     3600 caatagcagg catgctgggg atgcggtggg ctctatgggt acccaggtgc tgaagaattg    3660
acccggttcc tcctgggcca gaaagaagca ggcacatccc cttctctgtg acacaccctg    3720
tccacgcccc tggttcttag ttccagcccc actcatagga cactcatagc tcaggagggc    3780
```

```
tccgccttca atcccacccg ctaaagtact tggagcggtc tctccctccc tcatcagccc    3840
accaaaccaa acctagcctc caagagtggg aagaaattaa agcaagatag gctattaagt    3900
gcagagggag agaaaatgcc tccaacatgt gaggaagtaa tgagagaaat catagaattt    3960
taaggccatg atttaaggcc atcatggcct taatcttccg cttcctcgct cactgactcg    4020
ctgcgctcgg tcgttcggct gcggcgagcg gtatcagctc actcaaaggc ggtaatacgg    4080
ttatccacag aatcagggga taacgcagga agaacatgt gagcaaaagg ccagcaaaag    4140
gccaggaacc gtaaaaaggc cgcgttgctg gcgtttttcc ataggctccg ccccctgac    4200 gagcatcaca aaaatcgacg ctcaagtcag aggtggcgaa acccgacagg actataaaga    4260
taccaggcgt ttccccctgg aagctccctc gtgcgctctc ctgttccgac cctgccgctt    4320
accggatacc tgtccgcctt tctcccttcg ggaagcgtgg cgctttctca tagctcacgc    4380
tgtaggtatc tcagttcggt gtaggtcgtt cgctccaagc tgggctgtgt gcacgaaccc    4440
cccgttcagc ccgaccgctg cgccttatcc ggtaactatc gtcttgagtc caacccggta    4500
agacacgact tatcgccact ggcagcagcc actggtaaca ggattagcag agcgaggtat    4560
gtaggcggtg ctacagagtt cttgaagtgg tggcctaact acggctacac tagaagaaca    4620
gtatttggta tctgcgctct gctgaagcca gttaccttcg gaaaaagagt tggtagctct    4680
tgatccggca aacaaaccac cgctggtagc ggtggttttt tgtttgcaa gcagcagatt    4740 acgcgcagaa aaaaggatc tcaagaagat cctttgatct tttctacggg gtctgacgct    4800
cagtggaacg aaaactcacg ttaagggatt ttggtcatga gattatcaaa aaggatcttc    4860
acctagatcc ttttaaatta aaaatgaagt tttaaatcaa tctaaagtat atatgagtaa    4920
acttggtctg acagttacca atgcttaatc agtgaggcac ctatctcagc gatctgtcta    4980
tttcgttcat ccatagttgc ctgactcggg gggggggggc gctgaggtct gcctcgtgaa    5040
gaaggtgttg ctgactcata ccaggcctga atcgccccat catccagcca gaaagtgagg    5100
gagccacggt tgatgagagc tttgttgtag gtggaccagt tggtgatttt gaacttttgc    5160
tttgccacgg aacggtctgc gttgtcggga agatgcgtga tctgatcctt caactcagca    5220
aaagttcgat ttattcaaca aagccgccgt cccgtcaagt cagcgtaatg ctctgccagt    5280
gttacaacca attaaccaat tctgattaga aaaactcatc gagcatcaaa tgaaactgca    5340
atttattcat atcaggatta tcaataccat attttgaaa aagccgtttc tgtaatgaag    5400
gagaaaactc accgaggcag ttccatagga tggcaagatc ctggtatcgg tctgcgattc    5460
cgactcgtcc aacatcaata aaccctatta atttcccctc gtcaaaaata aggttatcaa    5520
gtgagaaatc accatgagtg acgactgaat ccggtgagaa tggcaaaagc ttatgcattt    5580
ctttccagac ttgttcaaca ggccagccat tacgctcgtc atcaaaatca ctcgcatcaa    5640
ccaaaccgtt attcattcgt gattgcgcct gagcgagacg aaatacgcga tcgctgttaa    5700
aaggacaatt acaaacagga atcgaatgca accggcgcag gaacactgcc agcgcatcaa    5760
caatattttc acctgaatca ggatattctt ctaatacctg gaatgctgtt ttcccgggga    5820
tcgcagtggt gagtaaccat gcatcatcag gagtacggat aaaatgcttg atggtcggaa    5880
gaggcataaa ttccgtcagc cagtttagtc tgaccatctc atctgtaaca tcattggcaa    5940
cgctaccttt gccatgtttc agaaacaact ctggcgcatc gggcttccca tacaatcgat    6000
agattgtcgc acctgattgc ccgacattat cgcgagccca tttataccca tataaatcag    6060
catccatgtt ggaatttaat cgcggcctcg agcaagacgt ttcccgttga atatggctca    6120
taacacccct tgtattactg tttatgtaag cagacagttt tattgttcat gatgatatat    6180
```

```
ttttatcttg tgcaatgtaa catcagagat tttgagacac aacgtggctt tccccccccc    6240
cccattattg aagcatttat cagggttatt gtctcatgag cggatacata tttgaatgta    6300
tttagaaaaa taaacaaata ggggttccgc gcacatttcc ccgaaaagtg ccacctgacg    6360
tctaagaaac cattattatc atgacattaa cctataaaaa taggcgtatc acgaggccct    6420
ttcgtc                                                              6426

<210> SEQ ID NO 2
<211> LENGTH: 6424
<212> TYPE: DNA
<213> ORGANISM: Ebola (Zaire)

<400> SEQUENCE: 2
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga cttttccattg acgtcaatgg gtggagtatt tacggtaaac     540
tgcccacttg gcagtacatc aagtgtatca tatgccaagt acgccccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atgggcgtga ccggcatcct    1380
gcagctgccc agggacaggt tcaagaggac cagcttcttc ctgtgggtga tcatcctgtt    1440 ccagagggacc ttcagcatcc ccctgggcgt gatccacaac agcacctgc aggtgagcga    1500 cgtggacaag ctggtgtgca gggacaagct gagcagcacc aaccagctga ggagcgtggg    1560
cctgaacctg gagggcaacg gcgtggccac cgacgtgccc agcgccacca agaggtgggg    1620
cttcaggagc ggcgtgcctc ccaaggtggt gaactacgag gccgcgagt gggccgagaa    1680 ctgctacaac ctggagatca agaagcccga cggcagcgag tgcctgcccg ccgcccctga    1740
cggcatcagg ggcttcccca ggtgcaggta cgtgcacaag gtgagcggca ccggcccctg    1800
cgccggcgac ttcgccttcc acaaggaggg cgccttcttc ctgtacgaca ggctggccag    1860
```

```
caccgtgatc tacaggggca ccaccttcgc cgagggcgtg gtggccttcc tgatcctgcc   1920
ccaggccaag aaggacttct tcagcagcca ccctctgagg gagcccgtga acgccaccga   1980 ggacccagc agcggctact acagcaccac catcaggtac caggccaccg cttcggcac    2040 caacgagacc gagtacctgt tcgaggtgga caacctgacc tacgtgcagc tggagtctag   2100
attcacccct cagttcctgc tgcagctgaa cgagaccatc tacaccagcg gcaagaggag   2160
caacaccacc ggcaagctga tctggaaggt gaaccccgag atcgacacca ccatcggcga   2220
gtgggccttc tgggagacca agaagaacct gaccaggaag atcaggagcg aggagctgag   2280
cttcaccgtc gtgagcaacg ggccaagaa catcagcggc cagagccccg ccaggaccag   2340
cagcgacccc ggcaccaaca ccaccaccga ggaccacaag atcatggcca gcgagaacag   2400
cagcgccatg gtgcaggtgc acagccaggg cagggaggcc gccgtgagcc acctgaccac   2460
cctggccacc atcagcacca gccctcagtc tttaaccacc aagcccggcc ccgacaacag   2520
cacccacaac acccctgtgt acaagctgga catcagcgag gccacccagg tggagcagca   2580
ccacaggagg accgacaacg acagcaccgc cagcgacacc ccttccgcca ccaccgccgc   2640
cggccctccg aaggccgaga acaccaacac cagcaagagc accgactttc tggatcccgc   2700
caccaccacc agccctcaga accacagcga accgccggc aacaacaaca cccaccacca   2760
ggacaccggc gaggagagcg ccagcagcgg caagctgggc ctgatcacca acaccatcgc   2820
cggcgtggcc ggcctgatca ccggcggcag gaggaccagg agggaggcca tcgtgaacgc   2880
ccagcccaag tgcaaccccca acctgcacta ctggaccacc caggacgagg cgccgccat   2940 cggcctggcc tggattccct acttcggccc cgccgccgag ggcatctaca tcgagggcct   3000
gatgcacaac caggacggcc tgatctgcgg cctgaggcag ctggccaacg agaccaccca   3060
ggccctgcag ctgttcctga gggccaccac cgagctgagg accttcagca tcctgaacag   3120
gaaggccatc gacttcctgc tgcagaggtg gggcggcacc tgccacatcc tgggccccga   3180
ctgctgcatc gagccccacg actggaccaa gaacatcacc gacaagatcg accagatcat   3240
ccacgacttc gtggacaaga ccctgccaga ccagggcgac aacgacaact ggtggaccgg   3300
ctggcggcag tggataccty ccggcatcgg cgtgaccggc gtggtgatcg ccgtgatcgc   3360
tctgttctgc atctgcaagt tcgtgttctg aacacgtgga attcagatct gctgtgcctt   3420
ctagttgcca gccatctgtt gtttgcccct cccccgtgcc ttccttgacc ctggaaggtg   3480
ccactcccac tgtcctttcc taataaaatg aggaaattgc atcgcattgt ctgagtaggt   3540
gtcattctat tctggggggt ggggtggggc aggacagcaa gggggaggat tgggaagaca   3600
atagcaggca tgctggggat gcggtgggct ctatgggtac ccaggtgctg aagaattgac   3660
ccggttcctc ctgggccaga agaagcagg cacatcccct tctctgtgac acccctgtc    3720 cacgcccctg gttcttagtt ccagcccac tcataggaca ctcatagctc aggagggctc   3780
cgccttcaat cccacccgct aaagtacttg gagcggtctc tccctccctc atcagcccac   3840
caaaccaaac ctagcctcca agagtgggaa gaaattaaag caagataggc tattaagtgc   3900
agagggagag aaaatgcctc caacatgtga ggaagtaatg agagaaatca tagaattta    3960 aggccatgat ttaaggccat catggcctta atcttccgct tcctcgctca ctgactcgct   4020
gcgctcggtc gttcggctgc ggcgagcggt atcagctcac tcaaaggcgg taatacggtt   4080
atccacagaa tcaggggata acgcaggaaa gaacatgtga gcaaaaggcc agcaaaggc    4140 caggaaccgt aaaaaggccg cgttgctggc gtttttccat aggctccgcc ccctgacga    4200 gcatcacaaa aatcgacgct caagtcagag gtggcgaaac ccgacaggac tataaagata   4260
```

```
ccaggcgttt cccctggaa gctccctcgt gcgctctcct gttccgaccc tgccgcttac   4320
cggatacctg tccgcctttc tcccttcggg aagcgtggcg ctttctcata gctcacgctg   4380
taggtatctc agttcggtgt aggtcgttcg ctccaagctg ggctgtgtgc acgaaccccc   4440
cgttcagccc gaccgctgcg ccttatccgg taactatcgt cttgagtcca acccggtaag   4500
acacgactta tcgccactgg cagcagccac tggtaacagg attagcagag cgaggtatgt   4560
aggcggtgct acagagttct tgaagtggtg gcctaactac ggctacacta aagaacagt    4620 atttggtatc tgcgctctgc tgaagccagt taccttcgga aaaagagttg gtagctcttg   4680
atccggcaaa caaaccaccg ctggtagcgg tggttttttt gtttgcaagc agcagattac   4740
gcgcagaaaa aaaggatctc aagaagatcc tttgatcttt tctacggggt ctgacgctca   4800
gtggaacgaa aactcacgtt aagggatttt ggtcatgaga ttatcaaaaa ggatcttcac   4860
ctagatcctt ttaaattaaa aatgaagttt taaatcaatc taaagtatat atgagtaaac   4920
ttggtctgac agttaccaat gcttaatcag tgaggcacct atctcagcga tctgtctatt   4980
tcgttcatcc atagttgcct gactcggggg ggggggcgc tgaggtctgc ctcgtgaaga   5040
aggtgttgct gactcatacc aggcctgaat cgccccatca tccagccaga aagtgaggga   5100
gccacggttg atgagagctt tgttgtaggt ggaccagttg gtgattttga acttttgctt   5160
tgccacggaa cggtctgcgt tgtcgggaag atgcgtgatc tgatccttca actcagcaaa   5220
agttcgattt attcaacaaa gccgccgtcc cgtcaagtca gcgtaatgct ctgccagtgt   5280
tacaaccaat taaccaattc tgattagaaa aactcatcga gcatcaaatg aaactgcaat   5340
ttattcatat caggattatc aataccatat ttttgaaaaa gccgtttctg taatgaagga   5400
gaaaactcac cgaggcagtt ccataggatg gcaagatcct ggtatcggtc tgcgattccg   5460
actcgtccaa catcaataca acctattaat ttcccctcgt caaaaataag gttatcaagt   5520
gagaaatcac catgagtgac gactgaatcc ggtgagaatg gcaaaagctt atgcatttct   5580
ttccagactt gttcaacagg ccagccatta cgctcgtcat caaaatcact cgcatcaacc   5640
aaaccgttat tcattcgtga ttgcgcctga gcgagacgaa atacgcgatc gctgttaaaa   5700
ggacaattac aaaacaggaat cgaatgcaac cggcgcagga acactgccag cgcatcaaca   5760
atattttcac ctgaatcagg atattcttct aatacctgga atgctgtttt cccggggatc   5820
gcagtggtga gtaaccatgc atcatcagga gtacggataa aatgcttgat ggtcggaaga   5880
ggcataaatt ccgtcagcca gtttagtctg accatctcat ctgtaacatc attggcaacg   5940
ctacctttgc catgtttcag aaacaactct ggcgcatcgg gcttcccata caatcgatag   6000
attgtcgcac ctgattgccc gacattatcg cgagcccatt tatacccata taaatcagca   6060
tccatgttgg aatttaatcg cggcctcgag caagacgttt cccgttgaat atggctcata   6120 acacccccttg tattactgtt tatgtaagca gacagttta ttgttcatga tgatatattt   6180
ttatcttgtg caatgtaaca tcagagattt tgagacacaa cgtggctttc cccccccccc   6240
cattattgaa gcatttatca gggttattgt ctcatgagcg gatacatatt tgaatgtatt   6300
tagaaaaata aacaaatagg ggttccgcgc acatttcccc gaaagtgcc acctgacgtc   6360 taagaaacca ttattcat gacattaacc tataaaaata ggcgtatcac gaggcccttt   6420
cgtc                                                                6424
```

<210> SEQ ID NO 3
<211> LENGTH: 6414
<212> TYPE: DNA
<213> ORGANISM: Ebola virus (Sudan, Gulu)

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcaggcgcg  tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca      960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atggagggcc tgagcctgct    1380
gcagctgccc agggacaagt tcaggaagag cagcttcttc gtgtgggtga tcatcctgtt    1440
ccagaaggcc ttcagcatgc ccctgggcgt ggtgaccaac agcaccctgg aggtgaccga    1500
gatcgaccag ctggtgtgca aggaccacct ggccagcacc gaccagctga agagcgtggg    1560
cctgaacctg gacggcagcg gcgtgagcac cgacatcccc agcgccacca gaggtgggg     1620
cttcaggagc ggcgtgcctc ccaaggtggt gagctacgag gccggcgagt gggccgagaa    1680
ctgctacaac ctggagatca agaagcccga cggcagcgag tgcctgcctc ctcctcctga    1740
cggcgtgagg ggcttcccca ggtgcaggta cgtgcacaag gcccagggca ccggcccctg    1800
ccccggcgac tacgccttcc acaaggacgc cgccttcttc ctgtacgaca ggctggccag    1860
caccgtgatc tacaggggcg tgaacttcgc cgagggcgtg atcgccttcc tgatcctggc    1920
caagcccaag gagaccttcc tgcagagccc tcccatcagg gaggccgtga actacaccga    1980
gaacaccagc agctactacg ccaccagcta tctagagtac gagatcgaga acttcggcgc    2040
ccagcacagc accaccctgt tcaagatcga caacaacacc ttcgtgaggc tggacaggcc    2100
ccacacccct cagttcctgt tccagctgaa cgacaccatc cacctgcacc agcagctgag    2160
caacaccacc ggcaggctga tctggaccct ggacgccaac atcaacgccg acatcggcga    2220
gtgggccttc tgggagaaca gaagaacct  gagcgagcag ctgaggggcg aggagctgag    2280
cttcgaggcc ctgagcctga acgagaccga ggacgacgac gccgccagca gcaggatcac    2340
```

```
caagggcagg atcagcgaca gggccaccag gaagtacagc gacctggtgc ccaagaacag    2400
ccccggcatg gtgcccctgc acatccccga gggcgagacc accctgccca gccagaacag    2460
caccgagggc aggagggtgg gcgtgaacac ccaggagacc atcaccgaga ccgccgccac    2520
catcatcggc accaacggca accacatgca gatcagcacc atcggcatca ggcccagcag    2580
cagccagatc cccagcagca gccccaccac cgccccctagc cccgaggccc agaccccac    2640 cacccacacc agcggaccca gcgtgatggc caccgaggag cccaccaccc ctcccggcag    2700
cagccccgga cccaccaccg aggcccctac cctgaccacc cctgagaaca tcaccaccgc    2760
cgtgaagacc gtgctgcccc aggagagcac cagcaacggc ctgatcacca gcaccgtgac    2820
cggcatcctg ggcagcctgg gcctgaggaa gaggagcagg aggcagacca caccaaggc    2880 caccggcaag tgcaaccca acctgcacta ctggaccgcc caggagcagc acaacgccgc    2940
cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctacacca tcctgaacag    3120
gaaggccatc gacttcctgc tgaggaggtg gggcggcacc tgcaggattc tgggccccga    3180
ctgctgcatc gagccccacg actggaccaa gaacatcacc gacaagatca ccagatcat    3240 ccacgacttc atcgacaacc ctctgcccaa ccaggacaac gacgacaact ggtggaccgg    3300
ctggcggcag tggataacctg ccggcatcgg catcaccggc atcatcatcg ccatcatcgc    3360
tctgctgtgc gtgtgcaagc tgctgtgctg aacacgatct gctgtgcctt ctagttgcca    3420
gccatctgtt gtttgcccct cccccgtgcc ttccttgacc ctggaaggtg ccactcccac    3480
tgtcctttcc taataaaatg aggaaattgc atcgcattgt ctgagtaggt gtcattctat    3540 tctgggggt ggggtgggc aggacagcaa ggggggaggat tgggaagaca atagcaggca    3600
tgctggggat gcgtgggct ctatgggtac ccaggtgctg aagaattgac ccggttcctc    3660
ctgggccaga agaagcagg cacatcccct tctctgtgac acccctgtc cacgcccctg    3720 gttcttagtt ccagccccac tcataggaca ctcatagctc aggagggctc cgccttcaat    3780
cccacccgct aaagtacttg gagcggtctc tccctccctc atcagcccac caaaccaaac    3840
ctagcctcca agagtgggaa gaaattaaag caagataggc tattaagtgc agagggagag    3900
aaaatgcctc caacatgtga ggaagtaatg agagaaatca tagaattta aggccatgat    3960 ttaaggccat catggcctta atcttccgct tcctcgctca ctgactcgct gcgctcggtc    4020
gttcggctgc ggcgagcggt atcagctcac tcaaaggcgg taatacggtt atccacagaa    4080 tcagggata acgcaggaaa gaacatgtga gcaaaaggcc agcaaaaggc caggaaccgt    4140
aaaaaggccg cgttgctggc gtttttccat aggctccgcc ccctgacga gcatcacaaa    4200 aatcgacgct caagtcagag gtggcgaaac ccgacaggac tataaagata ccaggcgttt    4260 cccctggaa gctccctcgt gcgctctcct gttccgaccc tgccgcttac cggatacctg    4320 tccgccttc tcccttcggg aagcgtggcg ctttctcata gctcacgctg taggtatctc    4380
agttcggtgt aggtcgttcg ctccaagctg ggctgtgtgc acgaaccccc cgttcagccc    4440
gaccgctgcg ccttatccgg taactatcgt cttgagtcca acccggtaag acacgactta    4500
tcgccactgg cagcagccac tggtaacagg attagcagag cgaggtatgt aggcggtgct    4560
acagagttct tgaagtggtg gcctaactac ggctacacta agaacagt atttggtatc    4620 tgcgctctgc tgaagccagt taccttcgga aaaagagttg gtagctcttg atccggcaaa    4680
caaaccaccg ctggtagcgg tggttttttt gtttgcaagc agcagattac gcgcagaaaa    4740
```

| | |
|---|---|
| aaaggatctc aagaagatcc tttgatcttt tctacggggt ctgacgctca gtggaacgaa | 4800 |
| aactcacgtt aagggatttt ggtcatgaga ttatcaaaaa ggatcttcac ctagatcctt | 4860 |
| ttaaattaaa aatgaagttt taaatcaatc taaagtatat atgagtaaac ttggtctgac | 4920 |
| agttaccaat gcttaatcag tgaggcacct atctcagcga tctgtctatt tcgttcatcc | 4980 |
| atagttgcct gactcggggg ggggggggcgc tgaggtctgc ctcgtgaaga aggtgttgct | 5040 |
| gactcatacc aggcctgaat cgccccatca tccagccaga aagtgaggga gccacggttg | 5100 |
| atgagagctt tgttgtaggt ggaccagttg gtgattttga acttttgctt tgccacggaa | 5160 |
| cggtctgcgt tgtcggaag atgcgtgatc tgatccttca actcagcaaa agttcgattt | 5220 |
| attcaacaaa gccgccgtcc cgtcaagtca gcgtaatgct ctgccagtgt tacaaccaat | 5280 |
| taaccaattc tgattagaaa aactcatcga gcatcaaatg aaactgcaat ttattcatat | 5340 |
| caggattatc aataccatat ttttgaaaaa gccgtttctg taatgaagga gaaaactcac | 5400 |
| cgaggcagtt ccataggatg caagatcct ggtatcggtc tgcgattccg actcgtccaa | 5460 |
| catcaataca acctattaat ttcccctcgt caaaaataag gttatcaagt gagaaatcac | 5520 |
| catgagtgac gactgaatcc ggtgagaatg gcaaaagctt atgcatttct ttccagactt | 5580 |
| gttcaacagg ccagccatta cgctcgtcat caaaatcact cgcatcaacc aaaccgttat | 5640 |
| tcattcgtga ttgcgcctga gcgagacgaa atacgcgatc gctgttaaaa ggacaattac | 5700 |
| aaacaggaat cgaatgcaac cggcgcagga acactgccag cgcatcaaca atattttcac | 5760 |
| ctgaatcagg atattcttct aatacctgga atgctgtttt cccggggatc gcagtggtga | 5820 |
| gtaaccatgc atcatcagga gtacggataa aatgcttgat ggtcggaaga ggcataaatt | 5880 |
| ccgtcagcca gtttagtctg accatctcat ctgtaacatc attggcaacg ctacctttgc | 5940 |
| catgtttcag aaacaactct ggcgcatcgg gcttcccata caatcgatag attgtcgcac | 6000 |
| ctgattgccc gacattatcg cgagcccatt tatacccata taaatcagca tccatgttgg | 6060 |
| aatttaatcg cggcctcgag caagacgttt cccgttgaat atggctcata caccccttg | 6120 |
| tattactgtt tatgtaagca gacagtttta ttgttcatga tgatatattt ttatcttgtg | 6180 |
| caatgtaaca tcagagattt tgagacacaa cgtggctttc ccccccccc cattattgaa | 6240 |
| gcatttatca gggttattgt ctcatgagcg gatacatatt tgaatgtatt tagaaaaata | 6300 |
| aacaaatagg ggttccgcgc acatttcccc gaaaagtgcc acctgacgtc taagaaacca | 6360 |
| ttattatcat gacattaacc tataaaaata ggcgtatcac gaggccctt cgtc | 6414 |

<210> SEQ ID NO 4
<211> LENGTH: 6424
<212> TYPE: DNA
<213> ORGANISM: Ebola Virus (Zaire)

<400> SEQUENCE: 4

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |

```
catagtaacg ccaatacggga ctttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacga tatcgccgcc atgggcgtga ccggcatcct   1380
gcagctgccc agggacaggt tcaagaggac cagcttcttc ctgtgggtga tcatcctgtt   1440
ccagaggacc ttcagcatcc cctgggcgt gatccacaac agcaccctgc aggtgagcga    1500
cgtggacaag ctggtgtgca gggacaagct gagcagcacc aaccagctga ggagcgtggg   1560
cctgaacctg gacggcaacg gcgtggccac cgacgtgccc agcgccacca agaggtgggg   1620
cttcaggagc ggcgtgcctc ccaaggtggt gaactacgag gccggcgagt gggccgagaa   1680
ctgctacaac ctggagatca agaagcccga cggcagcgag tgcctgcccg ccgcccctga   1740
cggcatcagg ggcttcccca ggtgcaggta cgtgcacaag gtgagcggca ccggccctg    1800
cgccggcgac ttcgccttcc acaaggaggg cgccttcttc ctgtacgaca ggctggccag   1860
caccgtgatc tacaggggca ccaccttcgc cgagggcgtg gtggccttcc tgatcctgcc   1920
ccaggccaag aaggacttct tcagcagcca ccctctgagg gagcccgtga acgccaccga   1980
ggacccccagc agcggctact acagcaccac catcaggtac caggccaccg gcttcggcac   2040
caacgagacc gagtacctgt cgaggtgga caacctgacc tacgtgcagc tggagtctag   2100
attcaccccct cagttcctgc tgcagctgaa cgagaccatc tacaccgcg gcaagaggag    2160
caacaccacc ggcaagctga tctggaaggt gaaccccgag atcgacacca ccatcggcga   2220
gtgggccttc tgggagacca agaagaacct gaccaggaag atcaggagcg aggagctgag   2280
cttcaccgtc gtgagcaacg ggccaagaa catcagcggc cagagcccg ccaggaccag    2340
cagcgacccc ggcaccaaca ccaccaccga ggaccacaag atcatggcca gcagaacag   2400
cagcgccatg gtgcaggtgc acagccaggg caggaaggcc gccgtgagcc acctgaccac   2460
cctggccacc atcagcacca gccctcagtc tttaaccacc aagcccggcc ccgacaacag   2520
cacccacaac accctgtgt acaagctgga catcagcgag gccacccagg tgagcagca    2580
ccacaggagg accgacaacg acagcaccgc cagcgacacc ccttccgcca ccaccgccgc   2640
cggccctccg aaggccgaga acaccaacac cagcaagagc accgactttc tggatcccgc   2700
caccaccacc agccctcaga accacagcga accgccggc aacaacaaca cccaccacca    2760
ggaccccggc gaggagagcg ccagcagcgg caagctgggc ctgatcacca acaccatcgc   2820
cggcgtggcc ggcctgatca ccggcggcag gaggaccagg agggaggcca tcgtgaacgc   2880
```

```
ccagcccaag tgcaaccccca acctgcacta ctggaccacc caggacgagg gcgccgccat   2940
cggcctggcc tggattccct acttcggccc cgccgccgag ggcatctaca tcgagggcct   3000
gatgcacaac caggacggcc tgatctgcgg cctgaggcag ctggccaacg agaccaccca   3060
ggccctgcag ctgttcctga gggccaccac cgagctgagg accttcagca tcctgaacag   3120
gaaggccatc gacttcctgc tgcagaggtg gggcggcacc tgccacatcc tgggccccga   3180
ctgctgcatc gagccccacg actggaccaa gaacatcacc gacaagatcg accagatcat   3240
ccacgacttc gtggacaaga ccctgccaga ccagggcgac aacgacaact ggtggaccgg   3300
ctggcggcag tggatacctg ccggcatcgg cgtgaccggc gtggtgatcg ccgtgatcgc   3360
tctgttctgc atctgcaagt tcgtgttctg aacacgtgga attcagatct gctgtgcctt   3420
ctagttgcca gccatctgtt gtttgcccct cccccgtgcc ttccttgacc ctggaaggtg   3480
ccactcccac tgtcctttcc taataaaatg aggaaattgc atcgcattgt ctgagtaggt   3540
gtcattctat tctgggggt ggggtggggc aggacagcaa gggggaggat tgggaagaca   3600
atagcaggca tgctggggat gcggtgggct ctatgggtac ccaggtgctg aagaattgac   3660
ccggttcctc ctgggccaga aagaagcagg cacatcccct tctctgtgac acaccctgtc   3720
cacgcccctg gttcttagtt ccagcccac tcataggaca ctcatagctc aggagggctc   3780
cgccttcaat cccacccgct aaagtacttg gagcggtctc tccctccctc atcagcccac   3840
caaaccaaac ctagcctcca agagtgggaa gaaattaaag caagataggc tattaagtgc   3900
agagggagag aaaatgcctc caacatgtga ggaagtaatg agagaaatca tagaattta   3960
aggccatgat ttaaggccat catggcctta atcttccgct tcctcgctca ctgactcgct   4020
gcgctcggtc gttcggctgc ggcgagcggt atcagctcac tcaaaggcgg taatacggtt   4080
atccacagaa tcaggggata acgcaggaaa gaacatgtga gcaaaaggcc agcaaaaggc   4140
caggaaccgt aaaaaggccg cgttgctggc gtttttccat aggctccgcc ccctgacga   4200
gcatcacaaa aatcgacgct caagtcagag gtggcgaaac ccgacaggac tataaagata   4260
ccaggcgttt cccctggaa gctccctcgt gcgctctcct gttccgaccc tgccgcttac   4320
cggatacctg tccgccttc tcccttcggg aagcgtggcg ctttctcata gctcacgctg   4380
taggtatctc agttcggtgt aggtcgttcg ctccaagctg ggctgtgtgc acgaaccccc   4440
cgttcagccc gaccgctgcg ccttatccgg taactatcgt cttgagtcca acccggtaag   4500
acacgactta tcgccactgg cagcagccac tggtaacagg attagcagag cgaggtatgt   4560
aggcggtgct acagagttct tgaagtggtg gcctaactac ggctacacta agaacagt   4620
atttggtatc tgcgctctgc tgaagccagt taccttcgga aaagagttg gtagctcttg   4680
atccggcaaa caaaccaccg ctggtagcgg tggttttttt gtttgcaagc agcagattac   4740
gcgcagaaaa aaaggatctc aagaagatcc tttgatcttt tctacggggt ctgacgctca   4800
gtggaacgaa aactcacgtt aagggatttt ggtcatgaga ttatcaaaaa ggatcttcac   4860
ctagatcctt ttaaattaaa aatgaagttt taaatcaatc taaagtatat atgagtaaac   4920
ttggtctgac agttaccaat gcttaatcag tgaggcacct atctcagcga tctgtctatt   4980
tcgttcatcc atagttgcct gactcggggg gggggggcgc tgaggtctgc ctcgtgaaga   5040
aggtgttgct gactcatacc aggcctgaat cgccccatca tccagccaga aagtgaggga   5100
gccacggttg atgagagctt tgttgtaggt ggaccagttg gtgattttga acttttgctt   5160
tgccacggaa cggtctgcgt tgtcgggaag atgcgtgatc tgatccttca actcagcaaa   5220
agttcgattt attcaacaaa gccgccgtcc cgtcaagtca gcgtaatgct ctgccagtgt   5280
```

```
tacaaccaat taaccaattc tgattagaaa aactcatcga gcatcaaatg aaactgcaat      5340
ttattcatat caggattatc aataccatat ttttgaaaaa gccgtttctg taatgaagga      5400
gaaaactcac cgaggcagtt ccataggatg gcaagatcct ggtatcggtc tgcgattccg      5460
actcgtccaa catcaataca acctattaat ttccctcgt caaaaataag gttatcaagt       5520
gagaaatcac catgagtgac gactgaatcc ggtgagaatg gcaaaagctt atgcatttct      5580
ttccagactt gttcaacagg ccagccatta cgctcgtcat caaaatcact cgcatcaacc      5640
aaaccgttat tcattcgtga ttgcgcctga gcgagacgaa atacgcgatc gctgttaaaa      5700
ggacaattac aaacaggaat cgaatgcaac cggcgcagga acactgccag cgcatcaaca      5760
atattttcac ctgaatcagg atattcttct aatacctgga atgctgtttt cccggggatc      5820
gcagtggtga gtaaccatgc atcatcagga gtacggataa aatgcttgat ggtcggaaga      5880
ggcataaatt ccgtcagcca gtttagtctg accatctcat ctgtaacatc attggcaacg      5940
ctacctttgc catgtttcag aaacaactct ggcgcatcgg gcttcccata caatcgatag      6000
attgtcgcac ctgattgccc gacattatcg cgagcccatt tatacccata taaatcagca      6060
tccatgttgg aatttaatcg cggcctcgag caagacgttt cccgttgaat atggctcata      6120 acacccttg tattactgtt tatgtaagca gacagtttta ttgttcatga tgatatattt       6180
ttatcttgtg caatgtaaca tcagagattt tgagacacaa cgtggctttc cccccccccc      6240
cattattgaa gcatttatca gggttattgt ctcatgagcg gatacatatt tgaatgtatt      6300
tagaaaaata aacaaatagg ggttccgcgc acatttcccc gaaagtgcc acctgacgtc       6360 taagaaacca ttattatcat gacattaacc tataaaaata ggcgtatcac gaggcccttt      6420
cgtc                                                                   6424

<210> SEQ ID NO 5
<211> LENGTH: 6458
<212> TYPE: DNA
<213> ORGANISM: Marburg virus (Angola)

<400> SEQUENCE: 5
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
catagtaacg ccaatagggn cttttccattg acgtcaatgg gtggagtatt tacggtaaac       540
tgcccacttg gcagtacatc aagtgtatca tatgccaagt acgccccta ttgacgtcaa        600 tgacggtaaa tggcccgcct ggcattatgc ccagtacatg accttatggg actttcctac       660
ttggcagtac atctacgtat tagtcatcgc tattaccatg gtgatgcggt tttggcagta       720
catcaatggg cgtggatagc ggtttgactc acggggattt ccaagtctcc accccattga       780
cgtcaatggg agtttgtttt ggcaccaaaa tcaacgggac tttccaaaat gtcgtaacaa       840
ctccgcccca ttgacgcaaa tgggcggtag gcgtgtacgg tgggaggtct atataagcag       900
agctcgttta gtgaaccgtc agatcgcctg gagacgccat ccacgctgtt tgacctcca        960
```

```
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140 cttttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagag   1380
atatcgccgc catgaagacc acctgcctgc tgatcagcct gatcctgatc cagggcgtga   1440 agacccctgcc catcctggag atcgccagca catccagcc ccagaacgtg acagcgtgt   1500 gcagcggcac cctgcagaag accgaggacg tgcacctgat gggcttcacc ctgagcggcc   1560
agaaggtggc cgacagccct ctggaggcca gcaagaggtg ggccttcagg gccggcgtgc   1620
cccccaagaa cgtggagtac accgagggcg aggaggccaa gacctgctac aacatcagcg   1680
tgaccgaccc cagcggcaag agcctgctgc tggaccctcc caccaacatc agggactacc   1740
ctaagtgcaa gaccatccac cacatccagg gccagaaccc tcacgcccag gcatcgcccc   1800
tgcacctgtg gggcgccttc ttcctgtacg acaggatcgc cagcaccacc atgtacagag   1860
gaaaagtgtt cacagaggga aacatcgctg ctatgatcgt gaacaagacc gtgcataaga   1920
tgatcttcag cagacaggga cagggatata gacatatgaa cctgacatcc acaaacaagt   1980
actggacaag cagcaacgga acacagacaa acgatacagg atgttttgga acactgcagg   2040
aatacaactc caccaagaac cagacatgtg cccctagcaa gaagcctctg cctctgccta   2100
cagctcatcc tgaagtgaag ctgacatcca aagcacaga tgccacaaag ctgaacacaa   2160
cagatcctaa tagcgacgac gaggatctga caacaagcgg atccggatcc ggagaacagg   2220
aaccttatac aacaagcgac gctgctacaa aacaggact gtcctccaca atgcctccta   2280
cacctagccc tcagcctagc acacctcagc agggaggcaa caacacaaac cattcccagg   2340
gagtggtgac agaacctgga aagacaaaca acagccca gcctagcatg cctcctcata   2400
acacaacaac aatcagcaca aacaacacct ccaagcacaa tctgagcaca cctagcgtgc   2460
ctattcagaa tgccaccaac tacaacacac agtccacagc ccctgaaaac gaacagacct   2520
ccgccccttc caaaacaacc ctgctgccta cagaaaaccc tacaacagcc aagagcacaa   2580
acagcacaaa gagccctaca caacagtgc ctaacacaac aaacaagtat agcacaagcc   2640
ctagccctac acctaattcc acagctcagc atctggtgta ttttagaaga aagagaaaca   2700
tcctgtggag agaaggagat atgttccctt ttctggatgg actgatcaac gctcctatcg   2760
attttgatcc tgtgcctaac acaaagacaa tctttgatga aagcagcagc agcggagcct   2820
ccgccgaaga agatcagcat gcctccccta acatcagcct gacactgagc tatttcccta   2880
aggtgaacga aaacacagcc cattccggag aaaacgaaaa cgattgtgat gccgaactga   2940
gaatctggag cgtgcaggaa gatgatctgg ccgccggact gagctggatc ccttttttg   3000 ggcccggaat tgaaggactg tacaccgccg gcctgatcaa gaaccagaac aacctggtgt   3060
gcaggctgag gaggctggcc aaccagaccg ccaagagcct ggagctgctg ctgagggtga   3120
ccaccgagga gaggaccttc agcctgatca acaggcacgc catcgacttc ctgctggcta   3180
ggtggggcgg cacctgcaag gtgctgggcc ccgactgctg catcggcatc gaggacctga   3240
gcaggaacat cagcgagcag atcgaccaga tcaagaagga cgagcagaag gagggcaccg   3300 gctgggggcct gggcggcaag tggtggacca gcgactgggg agtgctgaca aacctgggaa   3360
```

```
tcctgctgct gctgagcatt gccgtgctca ttgctctgtc ctgtatctgt agaatcttta   3420
ccaagtacat cggatgatag atctgctgtg ccttctagtt gccagccatc tgttgtttgc   3480
ccctcccccg tgccttcctt gaccctggaa ggtgccactc ccactgtcct ttcctaataa   3540
aatgaggaaa ttgcatcgca ttgtctgagt aggtgtcatt ctattctggg gggtggggtg   3600
gggcaggaca gcaaggggga ggattgggaa gacaatagca ggcatgctgg ggatgcggtg   3660
ggctctatgg gtacccaggt gctgaagaat tgacccggtt cctcctgggc cagaaagaag   3720
caggcacatc cccttctctg tgacacaccc tgtccacgcc cctggttctt agttccagcc   3780
ccactcatag gacactcata gctcaggagg gctccgcctt caatcccacc cgctaaagta   3840
cttggagcgg tctctcccte cctcatcagc ccaccaaacc aaacctagcc tccaagagtg   3900
ggaagaaatt aaagcaagat aggctattaa gtgcagaggg agagaaaatg cctccaacat   3960
gtgaggaagt aatgagagaa atcatagaat tttaaggcca tgatttaagg ccatcatggc   4020
cttaatcttc cgcttcctcg ctcactgact cgctgcgctc ggtcgttcgg ctgcggcgag   4080
cggtatcagc tcactcaaag gcggtaatac ggttatccac agaatcaggg gataacgcag   4140
gaaagaacat gtgagcaaaa ggccagcaaa aggccaggaa ccgtaaaaag gccgcgttgc   4200
tggcgttttt ccataggctc cgcccccctg acgagcatca aaaaatcga cgctcaagtc   4260 agaggtggcg aaacccgaca ggactataaa gataccaggc gtttccccct ggaagctccc   4320
tcgtgcgctc tcctgttccg accctgccgc ttaccggata cctgtccgcc tttctccctt   4380
cgggaagcgt ggcgctttct catagctcac gctgtaggta tctcagttcg gtgtaggtcg   4440
ttcgctccaa gctgggctgt gtgcacgaac cccccgttca gcccgaccgc tgcgccttat   4500
ccggtaacta tcgtcttgag tccaacccgg taagacacga cttatcgcca ctggcagcag   4560
ccactggtaa caggattagc agagcgaggt atgtaggcgg tgctacagag ttcttgaagt   4620
ggtggcctaa ctacggctac actagaagaa cagtatttgg tatctgcgct ctgctgaagc   4680
cagttacctt cggaaaaaga gttggtagct cttgatccgg caaacaaacc accgctggta   4740
gcggtggttt ttttgtttgc aagcagcaga ttacgcgcag aaaaaaagga tctcaagaag   4800
atcctttgat cttttctacg gggtctgacg ctcagtggaa cgaaaactca cgttaaggga   4860
ttttggtcat gagattatca aaaaggatct cacctagat cctttttaaat taaaaatgaa   4920 gttttaaatc aatctaaagt atatatgagt aaacttggtc tgacagttac caatgcttaa   4980
tcagtgaggc acctatctca gcgatctgtc tatttcgttc atccatagtt gcctgactcg   5040
gggggggggg gcgctgaggt ctgcctcgtg aagaaggtgt tgctgactca taccaggcct   5100
gaatcgcccc atcatccagc cagaaagtga gggagccacg gttgatgaga gctttgttgt   5160
aggtggacca gttggtgatt ttgaactttt gctttgccac ggaacggtct gcgttgtcgg   5220
gaagatgcgt gatctgatcc ttcaactcag caaaagttcg atttattcaa caaagccgcc   5280
gtcccgtcaa gtcagcgtaa tgctctgcca gtgttacaac caattaacca attctgatta   5340
gaaaaactca tcgagcatca atgaaactg catttattc atatcaggat tatcaatacc   5400 atattttga aaaagccgtt tctgtaatga aggagaaaac tcaccgaggc agttccatag   5460
gatggcaaga tcctggtatc ggtctgcgat tccgactcgt ccaacatcaa tacaacctat   5520
taattttccc tcgtcaaaaa taaggttatc aagtgagaaa tcaccatgag tgacgactga   5580
atccggtgag aatggcaaaa gcttatgcat ttctttccag acttgttcaa caggccagcc   5640
attacgctcg tcatcaaaat cactcgcatc aaccaaaccg ttattcattc gtgattgcgc   5700
ctgagcgaga cgaaatacgc gatcgctgtt aaaaggacaa ttacaaacag gaatcgaatg   5760
```

| | |
|---|---|
| caaccggcgc aggaacactg ccagcgcatc aacaatattt tcacctgaat caggatattc | 5820 |
| ttctaatacc tggaatgctg ttttcccggg gatcgcagtg gtgagtaacc atgcatcatc | 5880 |
| aggagtacgg ataaaatgct tgatggtcgg aagaggcata aattccgtca gccagtttag | 5940 |
| tctgaccatc tcatctgtaa catcattggc aacgctacct ttgccatgtt tcagaaacaa | 6000 |
| ctctggcgca tcgggcttcc catacaatcg atagattgtc gcacctgatt gcccgacatt | 6060 |
| atcgcgagcc catttatacc catataaatc agcatccatg ttggaattta atcgcggcct | 6120 |
| cgagcaagac gtttcccgtt gaatatggct cataacaccc cttgtattac tgtttatgta | 6180 |
| agcagacagt tttattgttc atgatgatat atttttatct tgtgcaatgt aacatcagag | 6240 |
| attttgagac acaacgtggc tttccccccc cccccattat tgaagcattt atcagggtta | 6300 |
| ttgtctcatg agcggataca tatttgaatg tatttagaaa aataaacaaa taggggttcc | 6360 |
| gcgcacattt ccccgaaaag tgccacctga cgtctaagaa accattatta tcatgacatt | 6420 |
| aacctataaa aataggcgta tcacgaggcc ctttcgtc | 6458 |

<210> SEQ ID NO 6
<211> LENGTH: 6458
<212> TYPE: DNA
<213> ORGANISM: Marburg virus (Angola)

<400> SEQUENCE: 6

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgccgg cgctctagag | 1380 |
| atatcgccgc catgaagacc acctgcctgc tgatcagcct gatcctgatc cagggcgtga | 1440 |

```
agaccctgcc catcctggag atcgccagca acatccagcc ccagaacgtg gacagcgtgt    1500
gcagcggcac cctgcagaag accgaggacg tgcacctgat gggcttcacc ctgagcggcc    1560
agaaggtggc cgacagccct ctggaggcca gcaagaggtg ggccttcagg gccggcgtgc    1620
cccccaagaa cgtggagtac accgaggccg aggaggccaa gacctgctac aacatcagcg    1680
tgaccgaccc cagcggcaag agcctgctgc tggaccctcc caccaacatc agggactacc    1740
ctaagtgcaa gaccatccac cacatccagg gccagaaccc tcacgcccag gcatcgccc     1800 tgcacctgtg gggcgccttc ttcctgtacg acaggatcgc cagcaccacc atgtacagag    1860
gaaaagtgtt cacagaggga aacatcgctg ctatgatcgt gaacaagacc gtgcataaga    1920
tgatcttcag cagacaggga caggatata gacatatgaa cctgacatcc acaaacaagt     1980
actggacaag cagcaacgga acacagacaa acgatacagg atgttttgga acactgcagg    2040
aatacaactc caccaagaac cagacatgtg ccctagcaa gaagcctctg cctctgccta     2100
cagctcatcc tgaagtgaag ctgacatcca caagcacaga tgccacaaag ctgaacacaa    2160
cagatcctaa tagcgacgac gaggatctga caacaagcgg atccggatcc ggagaacagg    2220
aaccttatac aacaagcgac gctgctacaa aacaggact gtcctccaca atgcctccta     2280
cacctagccc tcagcctagc acacctcagc agggaggcaa caacacaaac cattcccagg    2340
gagtggtgac agaacctgga aagacaaaca acacagccca gcctagcatg cctcctcata    2400
acacaacaac aatcagcaca aacaacacct ccaagcacaa tctgagcaca cctagcgtgc    2460
ctattcagaa tgccaccaac tacaacacac agtccacagc ccctgaaaac gaacagacct    2520
ccgccccttc caaaacaacc ctgctgccta cagaaaaccc tacaacagcc aagagcacaa    2580
acagcacaaa gagccctaca caacagtgc ctaacacaac aaacaagtat agcacaagcc     2640
ctagccctac acctaattcc acagctcagc atctggtgta ttttagaaga agagaaaca    2700 tcctgtggag agaaggagat atgttccctt ttctggatgg actgatcaac gctcctatcg    2760
attttgatcc tgtgcctaac acaaagacaa tctttgatga agcagcagc agcggagcct    2820 ccgccgaaga agatcagcat gcctccccta acatcagcct gacactgagc tatttttccta    2880 aggtgaacga aaacacagcc cattccggag aaaacgaaaa cgattgtgat gccgaactga    2940
gaatctggag cgtgcaggaa gatgatctgg ccgccggact gagctggatc cctttttttg     3000
ggcccggaat tgaaggactg tacaccgccg gcctgatcaa gaaccagaac aacctggtgt    3060
gcaggctgag gaggctggcc aaccagaccg ccaagagcct ggagctgctg ctgagggtga    3120
ccaccgagga gaggaccttc agcctgatca acaggcacgc catcgacttc ctgctggcta    3180
ggtggggcgg cacctgcaag gtgctgggcc ccgactgctg catcggcatc gaggacctga    3240
gcaggaacat cagcgagcag atcgaccaga tcaagaagga cgagcagaag gagggcaccg    3300
gctgggccct gggcggcaag tggtggacca cgactgggg agtgctgaca aacctgggaa     3360
tcctgctgct gctgagcatt gccgtgctca ttgctctgtc ctgtatctgt agaatcttta    3420
ccaagtacat cggatgatag atctgctgtg ccttctagtt gccagccatc tgttgtttgc    3480
ccctcccccg tgccttcctt gaccctggaa ggtgccactc ccactgtcct ttcctaataa    3540
aatgaggaaa ttgcatcgca ttgtctgagt aggtgtcatt ctattctggg gggtggggtg    3600
gggcaggaca gcaaggggga ggattggaa gacaatagca ggcatgctgg ggatgcggtg     3660
ggctctatgg gtacccaggt gctgaagaat tgacccggtt cctcctgggc cagaagaag     3720 caggcacatc cccttctctg tgacacaccc tgtccacgcc cctggttctt agttccagcc    3780
ccactcatag gacactcata gctcaggagg gctccgcctt caatcccacc cgctaaagta    3840
```

```
cttggagcgg tctctccctc cctcatcagc ccaccaaacc aaacctagcc tccaagagtg   3900
ggaagaaatt aaagcaagat aggctattaa gtgcagaggg agagaaaatg cctccaacat   3960
gtgaggaagt aatgagagaa atcatagaat tttaaggcca tgatttaagg ccatcatggc   4020
cttaatcttc cgcttcctcg ctcactgact cgctgcgctc ggtcgttcgg ctgcggcgag   4080
cggtatcagc tcactcaaag gcggtaatac ggttatccac agaatcaggg gataacgcag   4140
gaaagaacat gtgagcaaaa ggccagcaaa aggccaggaa ccgtaaaaag ccgcgttgc   4200
tggcgttttt ccataggctc cgcccccctg acgagcatca caaaaatcga cgctcaagtc   4260
agaggtggcg aaacccgaca ggactataaa gataccaggc gtttccccct ggaagctccc   4320
tcgtgcgctc tcctgttccg accctgccgc ttaccggata cctgtccgcc tttctccctt   4380
cgggaagcgt ggcgctttct catagctcac gctgtaggta tctcagttcg gtgtaggtcg   4440
ttcgctccaa gctgggctgt gtgcacgaac cccccgttca gcccgaccgc tgcgccttat   4500
ccggtaacta tcgtcttgag tccaacccgg taagacacga cttatcgcca ctggcagcag   4560
ccactggtaa caggattagc agagcgaggt atgtaggcgg tgctacagag ttcttgaagt   4620
ggtggcctaa ctacggctac actagaagaa cagtatttgg tatctgcgct ctgctgaagc   4680
cagttacctt cggaaaaaga gttggtagct cttgatccgg caaacaaacc accgctggta   4740
gcggtggttt ttttgtttgc aagcagcaga ttacgcgcag aaaaaaagga tctcaagaag   4800
atcctttgat cttttctacg ggtctgacg ctcagtggaa cgaaaactca cgttaaggga   4860
ttttggtcat gagattatca aaaggatct cacctagat cctttaaat taaaaatgaa   4920
gttttaaatc aatctaaagt atatatgagt aaacttggtc tgacagttac caatgcttaa   4980
tcagtgaggc acctatctca gcgatctgtc tatttcgttc atccatagtt gcctgactcg   5040
ggggggggg gcgctgaggt ctgcctcgtg aagaaggtgt tgctgactca taccaggcct   5100
gaatcgcccc atcatccagc cagaaagtga gggagccacg gttgatgaga gctttgttgt   5160
aggtggacca gttggtgatt ttgaactttt gctttgccac ggaacggtct gcgttgtcgg   5220
gaagatgcgt gatctgatcc ttcaactcag caaaagttcg atttattcaa caaagccgcc   5280
gtcccgtcaa gtcagcgtaa tgctctgcca gtgttacaac caattaacca attctgatta   5340
gaaaaactca tcgagcatca aatgaaactg caatttattc atatcaggat tatcaatacc   5400
atatttttga aaagccgtt tctgtaatga aggagaaaac tcaccgaggc agttccatag   5460
gatggcaaga tcctggtatc ggtctgcgat tccgactcgt ccaacatcaa tacaacctat   5520
taatttcccc tcgtcaaaaa taaggttatc aagtgagaaa tcaccatgag tgacgactga   5580
atccggtgag aatggcaaaa gcttatgcat ttctttccag acttgttcaa caggccagcc   5640
attacgctcg tcatcaaaat cactcgcatc aaccaaaccg ttattcattc gtgattgcgc   5700
ctgagcgaga cgaaatacgc gatcgctgtt aaaaggacaa ttacaaacag gaatcgaatg   5760
caaccggcgc aggaacactg ccagcgcatc aacaatattt tcacctgaat caggatattc   5820
ttctaatacc tggaatgctg ttttcccggg gatcgcagtg gtgagtaacc atgcatcatc   5880
aggagtacgg ataaaatgct tgatggtcgg aagaggcata aattccgtca gccagtttag   5940
tctgaccatc tcatctgtaa catcattggc aacgctacct ttgccatgtt cagaaacaa   6000
ctctggcgca tcgggcttcc catacaatcg atagattgtc gcacctgatt gcccgacatt   6060
atcgcgagcc catttatacc catataaatc agcatccatg ttggaattta atcgcggcct   6120
cgagcaagac gtttcccgtt gaatatggct cataacaccc cttgtattac tgtttatgta   6180
agcagacagt tttattgttc atgatgatat attttatct tgtgcaatgt aacatcagag   6240
```

| | | |
|---|---|---|
| attttgagac acaacgtggc tttcccccc cccccattat tgaagcattt atcagggtta | | 6300 |
| ttgtctcatg agcggataca tatttgaatg tatttagaaa aataaacaaa taggggttcc | | 6360 |
| gcgcacattt ccccgaaaag tgccacctga cgtctaagaa accattatta tcatgacatt | | 6420 |
| aacctataaa aataggcgta tcacgaggcc ctttcgtc | | 6458 |

<210> SEQ ID NO 7
<211> LENGTH: 8128
<212> TYPE: DNA
<213> ORGANISM: Ebola virus (Zaire)

<400> SEQUENCE: 7

| | | |
|---|---|---|
| ttaattaacc gcaattctca tgtttgacag cttatcatca tcaataatat accttatttt | | 60 |
| ggattgaagc caatatgata tgaggggt ggagtttgtg acgtggcgcg gggcgtggga | | 120 |
| acggggcggg tgacgtagta gtgtggcgga agtgtgatgt tgcaagtgtg gcggaacaca | | 180 |
| tgtaagcgac ggatgtggca aaagtgacgt ttttggtgtg cgccggtgta cacaggaagt | | 240 |
| gacaattttc gcgcggtttt aggcggatgt tgtagtaaat ttgggcgtaa ccgagtaaga | | 300 |
| tttggccatt ttcgcgggaa aactgaataa gaggaagtga aatctgaata attttgtgtt | | 360 |
| actcatagcg cgtaatattt gtctagggcc gcggggactt tgaccgttta cgtggagact | | 420 |
| cgcccaggtg ttttctcag gtgttttccg cgttccgggt caaagttggc gttttattat | | 480 |
| tatagtcagt acgtaccagt gcactggcct aggtggtcaa tattggccat tagccatatt | | 540 |
| attcattggt tatatagcat aaatcaatat tggctattgg ccattgcata cgttgtatcc | | 600 |
| atatcataat atgtacattt atattggctc atgtccaaca ttaccgccat gttgacattg | | 660 |
| attattgact agttattaat agtaatcaat tacggggtca ttagttcata gcccatatat | | 720 |
| ggagttccgc gttacataac ttacggtaaa tggcccgcct ggctgaccgc ccaacgaccc | | 780 |
| ccgcccattg acgtcaataa tgacgtatgt tcccatagta acgccaatag ggactttcca | | 840 |
| ttgacgtcaa tgggtggagt atttacggta aactgcccac ttggcagtac atcaagtgta | | 900 |
| tcatatgcca gtacgccccc ctattgacgt caatgacggt aaatggcccg cctggcatta | | 960 |
| tgcccagtac atgaccttat gggactttcc tacttggcag tacatctacg tattagtcat | | 1020 |
| cgctattacc atggtgatgc ggttttggca gtacatcaat gggcgtggat agcggtttga | | 1080 |
| ctcacgggga tttccaagtc tccaccccat tgacgtcaat gggagtttgt tttggcacca | | 1140 |
| aaatcaacgg gactttccaa aatgtcgtaa caactccgcc ccattgacgc aaatgggcgg | | 1200 |
| taggcgtgta cggtgggagg tctatataag cagagctcgt ttagtgaacc gtcagatcgc | | 1260 |
| ctggagacgc catccacgct gttttgacct ccatagaaga caccgggacc gatccagcct | | 1320 |
| ccgcggccgg gaacggtgca ttggaagctt gccgccatgg gcgttacagg aatattgcag | | 1380 |
| ttacctcgtg atcgattcaa gaggacatca ttctttcttt gggtaattat ccttttccaa | | 1440 |
| agaacatttt ccatcccact tggagtcatc acaatagca cattacaggt tagtgatgtc | | 1500 |
| gacaaactag tttgtcgtga caaactgtca tccacaaatc aattgagatc agttggactg | | 1560 |
| aatctcgatg gcaatggagt ggcaactgac gtgccatctg caactaaaag atggggcttc | | 1620 |
| aggtccggtg tcccaccaaa ggtggtcaat tatgaagctg gtgaatgggc tgaaaactgc | | 1680 |
| tacaatcttg aaatcaaaaa acctgacggg agtgagtgtc taccagcagc gccagacggg | | 1740 |
| attcggggct tccccggtg ccggtatgtg cacaaagtat caggaacggg accgtgtgcc | | 1800 |
| ggagactttg ccttccataa agagggtgct ttcttcctgt atgatcgact tgcttccaca | | 1860 |
| gttatctacc gaggaacgac tttcgctgaa ggtgtcgttg catttctgat actgccccaa | | 1920 |

```
gctaagaagg acttcttcag ctcacacccc ttgagagagc cggtcaatgc aacggaggac    1980
ccgtctagtg gctactattc taccacaatt agatatcagg ctaccggttt tggaaccaat    2040
gagacagagt acttgttcga ggttgacaat ttgacctacg tccaacttga atcaagattc    2100
acaccacagt ttctgctcca gctgaatgag acaatatata caagtgggaa aaggagcaat    2160
accacgggaa aactaatttg gaaggtcaac cccgaaattg atacaacaat cggggagtgg    2220
gccttctggg aaactaaaaa aaacctcact agaaaaattc gcagtgaaga gttgtctttc    2280
acagttgtat caaacggagc caaaaacatc agtggtcaga gtccggcgcg aacttcttcc    2340
gacccaggga ccaacacaac aactgaagac cacaaaatca tggcttcaga aaattcctct    2400
gcaatggttc aagtgcacag tcaaggaagg gaagctgcag tgtcgcatct aacaacccct    2460
gccacaatct ccacgagtcc ccaatccctc acaaccaaac caggtccgga caacagcacc    2520
cataatacac ccgtgtataa acttgacatc tctgaggcaa ctcaagttga acaacatcac    2580
cgcagaacag acaacgacag cacagcctcc gacactccct ctgccacgac cgcagccgga    2640
cccccaaaag cagagaacac caacacgagc aagagcactg acttcctgga ccccgccacc    2700
acaacaagtc cccaaaaacca cagcgagacc gctggcaaca caacactca tcaccaagat    2760 accggagaag agagtgccag cagcgggaag ctaggcttaa ttaccaatac tattgctgga    2820
gtcgcaggac tgatcacagg cgggagaaga actcgaagag aagcaattgt caatgctcaa    2880
cccaaatgca accctaattt acattactgg actactcagg atgaaggtgc tgcaatcgga    2940
ctggcctgga taccatattt cgggccagca gccgagggaa tttacataga ggggctaatg    3000
cacaatcaag atggtttaat ctgtgggttg agacagctgg ccaacgagac gactcaagct    3060
cttcaactgt tcctgagagc cacaactgag ctacgcacct tttcaatcct caaccgtaag    3120
gcaattgatt tcttgctgca gcgatggggc ggcacatgcc acattctggg accggactgc    3180
tgtatcgaac cacatgattg gaccaagaac ataacagaca aaattgatca gattattcat    3240
gattttgttg ataaaacct tccggaccag ggggacaatg acaattggtg gacaggatgg    3300
agacaatgga taccggcagg tattggagtt acaggcgttg taattgcagt tatcgcttta    3360
ttctgtatat gcaaatttgt cttttagtaa tctagacgag atccgaactt gtttattgca    3420
gcttataatg gttacaaata aagcaatagc atcacaaatt tcacaaataa agcatttttt    3480
tcactgcatt ctagttgtgg tttgtccaaa ctcatcaatg tatcttatca tgtctagatc    3540
tgtactgaaa tgtgtgggcg tggcttaagg gtgggaaaga atatataagg tgggggtctt    3600
atgtagtttt gtatctgttt tgcagcagcc gccgccgcca tgagcaccaa ctcgtttgat    3660
ggaagcattg tgagctcata tttgacaacg cgcatgcccc catgggccgg ggtgcgtcag    3720
aatgtgatgg gctccagcat tgatggtcgc cccgtcctgc ccgcaaactc tactaccttg    3780
acctacgaga ccgtgtctgg aacgccgttg gagactgcag cctccgccgc cgcttcagcc    3840
gctgcagcca ccgcccgcgg gattgtgact gactttgctt cctgagcccc gcttgcaagc    3900
agtgcagctt cccgttcatc cgcccgcgat gacaagttga cggctctttt ggcacaattg    3960
gattctttga cccgggaact taatgtcgtt tctcagcagc tgttggatct cgccagcag    4020 gtttctgccc tgaaggcttc ctcccctccc aatgcggttt aaaacataaa taaaaaacca    4080
gactctgttt ggatttggat caagcaagtg tcttgctgtc tttatttagg ggttttgcgc    4140
gcgcggtagg cccgggacca gcggtctcgg tcgttgaggg tcctgtgtat ttttccagg    4200 acgtggtaaa ggtgactctg gatgttcaga tacatgggca taagcccgtc tctggggtgg    4260
aggtagcacc actgcagagc ttcatgctgc ggggtggtgt tgtagatgat ccagtcgtag    4320
```

```
caggagcgct gggcgtggtg cctaaaaatg tctttcagta gcaagctgat tgccaggggc    4380
aggcccttgg tgtaagtgtt tacaaagcgg ttaagctggg atgggtgcat acgtggggat    4440
atgagatgca tcttggactg tattttagg ttggctatgt tcccagccat atccctccgg    4500
ggattcatgt tgtgcagaac caccagcaca gtgtatccgg tgcacttggg aaatttgtca    4560
tgtagcttag aaggaaatgc gtggaagaac ttggagacgc ccttgtgacc tccaagattt    4620
tccatgcatt cgtccataat gatggcaatg ggcccacggg cggcggcctg ggcgaagata    4680
tttctgggat cactaacgtc atagttgtgt tccaggatga gatcgtcata ggccattttt    4740
acaaagcgcg ggcggagggt gccagactgc ggtataatgg ttccatccgg cccaggggcg    4800 tagttacccct cacagatttg catttcccac gctttgagtt cagatggggg gatcatgtct    4860
acctgcgggg cgatgaagaa aacggtttcc ggggtagggg agatcagctg ggaagaaagc    4920
aggttcctga gcagctgcga cttaccgcag ccggtgggcc cgtaaatcac acctattacc    4980
ggctgcaact ggtagttaag agagctgcag ctgccgtcat ccctgagcag gggggccact    5040
tcgttaagca tgtccctgac tcgcatgttt tccctgacca aatccgccag aaggcgctcg    5100
ccgcccagcg atagcagttc ttgcaaggaa gcaaagtttt tcaacggttt gagaccgtcc    5160
gccgtaggca tgcttttgag cgtttgacca agcagttcca ggcggtccca cagctcggtc    5220
acctgctcta cggcatctcg atccagcata tctcctcgtt tcgcggttg gggcggcttt    5280 cgctgtacgg cagtagtcgg tgctcgtcca gacgggccag ggtcatgtct ttccacgggc    5340
gcagggtcct cgtcagcgta gtctgggtca cggtgaaggg gtgcgctccg ggctgcgcgc    5400
tggccagggt gcgcttgagg ctggtcctgc tggtgctgaa gcgctgccgg tcttcgccct    5460
gcgcgtcggc caggtagcat ttgaccatgg tgtcatagtc cagcccctcc gcggcgtggc    5520
ccttggcgcg cagcttgccc ttggaggagg cgccgcacga ggggcagtgc agactttga    5580 gggcgtagag cttgggcgcg agaaataccg attccgggga gtaggcatcc cgcccgcagg    5640
ccccgcagac ggtctcgcat tccacgagcc aggtgagctc tggccgttcg gggtcaaaaa    5700 ccaggttttcc cccatgcttt ttgatgcgtt tcttacctct ggtttccatg agccggtgtc    5760
cacgctcggt gacgaaaagg ctgtccgtgt ccccgtatac agacttgaga ggcctgtcct    5820
cgagcggtgt tccgcggtcc tcctcgtata gaaactcgga ccactctgag acaaaggctc    5880
gcgtccaggc cagcacgaag gaggctaagt gggaggggta gcggtcgttg tccactaggg    5940
ggtccactcg ctccagggtg tgaagacaca tgtcgccctc ttcggcatca aggaaggtga    6000
ttggtttgta ggtgtaggcc acgtgaccgg gtgttcctga agggggggcta taaagggggg    6060 tgggggcgcg ttcgtcctca ctctcttccg catcgctgtc tgcgagggcc agctgttggg    6120
gtgagtcgac gcgaggctgg atggccttcc ccattatgat tcttctcgct tccggcggca    6180
tcgggatgcc cgcgttgcag gccatgctgt ccaggcaggt agatgacgac catcagggac    6240
agcttcaagg ccagcaaaag gccaggaacc gtaaaaggc cgcgttgctg gcgttttcc    6300 ataggctccg ccccctgac gagcatcaca aaaatcgacg ctcaagtcag aggtggcgaa    6360
acccgacagg actataaaga taccaggcgt ttccccctgg aagctccctc gtgcgctctc    6420
ctgttccgac cctgccgctt accggatacc tgtccgcctt tctcccttcg ggaagcgtgg    6480
cgctttctca tagctcacgc tgtaggtatc tcagttcggt gtaggtcgtt cgctccaagc    6540
tgggctgtgt gcacgaaccc cccgttcagc ccgaccgctg cgccttatcc ggtaactatc    6600
gtcttgagtc aacccggta agacacgact tatcgccact ggcagcagcc actggtaaca    6660
ggattagcag agcgaggtat gtaggcggtg ctacagagtt cttgaagtgg tggcctaact    6720
```

| | | | | |
|---|---|---|---|---|
| acggctacac | tagaaggaca | gtatttggta | tctgcgctct | gctgaagcca | gttaccttcg | 6780 |
| gaaaaagagt | tggtagctct | tgatccggca | aacaaaccac | cgctggtagc | ggtggttttt | 6840 |
| ttgtttgcaa | gcagcagatt | acgcgcagaa | aaaaaggatc | tcaagaagat | cctttgatct | 6900 |
| tttctacggg | gtctgacgct | cagtggaacg | aaaactcacg | ttaagggatt | ttggtcatga | 6960 |
| gattatcaaa | aaggatcttc | acctagatcc | ttttaaatta | aaaatgaagt | tttaaatcaa | 7020 |
| tctaaagtat | atatgagtaa | acttggtctg | acagttacca | atgcttaatc | agtgaggcac | 7080 |
| ctatctcagc | gatctgtcta | tttcgttcat | ccatagttgc | ctgactcccc | gtcgtgtaga | 7140 |
| taactacgat | acgggagggc | ttaccatctg | gccccagtgc | tgcaatgata | ccgcgagacc | 7200 |
| cacgctcacc | ggctccagat | ttatcagcaa | taaaccagcc | agccggaagg | gccgagcgca | 7260 |
| gaagtggtcc | tgcaacttta | tccgcctcca | tccagtctat | taattgttgc | cgggaagcta | 7320 |
| gagtaagtag | ttcgccagtt | aatagtttgc | gcaacgttgt | tgccattgct | gcaggcatcg | 7380 |
| tggtgtcacg | ctcgtcgttt | ggtatggctt | cattcagctc | cggttcccaa | cgatcaaggc | 7440 |
| gagttacatg | atccccccatg | ttgtgcaaaa | aagcggttag | ctccttcggt | cctccgatcg | 7500 |
| ttgtcagaag | taagttggcc | gcagtgttat | cactcatggt | tatggcagca | ctgcataatt | 7560 |
| ctcttactgt | catgccatcc | gtaagatgct | tttctgtgac | tggtgagtac | tcaaccaagt | 7620 |
| cattctgaga | atagtgtatg | cggcgaccga | gttgctcttg | cccggcgtca | acacgggata | 7680 |
| ataccgcgcc | acatagcaga | actttaaaag | tgctcatcat | tggaaaacgt | tcttcggggc | 7740 |
| gaaaactctc | aaggatctta | ccgctgttga | gatccagttc | gatgtaaccc | actcgtgcac | 7800 |
| ccaactgatc | ttcagcatct | tttactttca | ccagcgtttc | tgggtgagca | aaaacaggaa | 7860 |
| ggcaaaatgc | cgcaaaaaag | ggaataaggg | cgacacggaa | atgttgaata | ctcatactct | 7920 |
| tcctttttca | atattattga | agcatttatc | agggttattg | tctcatgagc | ggatacatat | 7980 |
| ttgaatgtat | ttagaaaaat | aaacaaatag | gggttccgcg | cacatttccc | cgaaaagtgc | 8040 |
| cacctgacgt | ctaagaaacc | attattatca | tgacattaac | ctataaaaat | aggcgtatca | 8100 |
| cgaggccctt | tcgtcttcaa | gaattgtt | | | | 8128 |

<210> SEQ ID NO 8
<211> LENGTH: 8128
<212> TYPE: DNA
<213> ORGANISM: Ebola (Sudan, Gulu)

<400> SEQUENCE: 8

| | | | | |
|---|---|---|---|---|
| ttaattaacc | gcaattctca | tgtttgacag | cttatcatca | tcaataatat | accttatttt | 60 |
| ggattgaagc | caatatgata | atgagggggt | ggagtttgtg | acgtggcgcg | gggcgtggga | 120 |
| acggggcggg | tgacgtagta | gtgtggcgga | agtgtgatgt | tgcaagtgtg | gcggaacaca | 180 |
| tgtaagcgac | ggatgtggca | aaagtgacgt | ttttggtgtg | cgccggtgta | cacaggaagt | 240 |
| gacaattttc | gcgcggtttt | aggcggatgt | tgtagtaaat | ttgggcgtaa | ccgagtaaga | 300 |
| tttggccatt | ttcgcgggaa | aactgaataa | gaggaagtga | aatctgaata | attttgtgtt | 360 |
| actcatagcg | cgtaatattt | gtctagggcc | gcggggactt | tgaccgttta | cgtggagact | 420 |
| cgcccaggtg | ttttttctcag | gtgttttccg | cgttccgggt | caaagttggc | gttttattat | 480 |
| tatagtcagt | acgtaccagt | gcactggcct | aggtggtcaa | tattggccat | tagccatatt | 540 |
| attcattggt | tatatagcat | aaatcaatat | tggctattgg | ccattgcata | cgttgtatcc | 600 |
| atatcataat | atgtacattt | atattggctc | atgtccaaca | ttaccgccat | gttgacattg | 660 |
| attattgact | agttattaat | agtaatcaat | tacggggtca | ttagttcata | gcccatatat | 720 |

```
ggagttccgc gttacataac ttacggtaaa tggcccgcct ggctgaccgc ccaacgaccc    780
ccgcccattg acgtcaataa tgacgtatgt tcccatagta acgccaatag ggactttcca    840
ttgacgtcaa tgggtggagt atttacggta aactgcccac ttggcagtac atcaagtgta    900
tcatatgcca agtacgcccc ctattgacgt caatgacggt aaatggcccg cctggcatta    960
tgcccagtac atgaccttat gggactttcc tacttggcag tacatctacg tattagtcat   1020
cgctattacc atggtgatgc ggttttggca gtacatcaat gggcgtggat agcggtttga   1080
ctcacgggga tttccaagtc tccaccccat tgacgtcaat gggagtttgt tttggcacca   1140
aaatcaacgg gactttccaa aatgtcgtaa caactccgcc ccattgacgc aaatgggcgg   1200
taggcgtgta cggtgggagg tctatataag cagagctcgt ttagtgaacc gtcagatcgc   1260
ctggagacgc catccacgct gttttgacct ccatagaaga caccgggacc gatccagcct   1320
ccgcggccgg aacggtgcat tggaagctt gccgccatgg gggtcttag cctactccaa   1380
ttgcccaggg acaaatttcg gaaaagctct ttctttgttt gggtcatcat cttattccaa   1440
aaggcctttt ccatgccttt gggtgttgtg actaacagca ctttagaagt aacagagatt   1500
gaccagctag tctgcaagga tcatcttgca tctactgacc agctgaaatc agttggtctc   1560
aacctcgacg ggagcggagt atctactgat atcccatctg caacaaagcg ttggggcttc   1620
agatctggtg ttcctcccaa ggtggtcagc tatgaagcgg gagaatgggc tgaaaattgc   1680
tacaatcttg aaataaagaa gccggacggg agcgaatgct taccccccacc gccagatggt   1740
gtcagaggct ttccaaggtg ccgctatgtt cacaaagccc aaggaaccgg gccctgccca   1800
ggtgactacg ccttttcacaa ggatggagct ttcttcctct atgacaggct ggcttcaact   1860
gtaatttaca gaggagtcaa ttttgctgag ggggtaattg cattcttgat attggctaaa   1920
ccaaaagaaa cgttccttca gtcacccccc attcgagagg cagtaaacta cactgaaaat   1980
acatcaagtt attatgccac atcctacttg gagtatgaaa tcgaaaattt tggtgctcaa   2040
cactccacga ccctttcaa aattgacaat aatacttttg ttcgtctgga caggccccac   2100
acgcctcagt tccttttcca gctgaatgat accattcacc ttcaccaaca gttgagtaat   2160
acaactggga gactaaattg acactagat gctaatatca atgctgatat tggtgaatgg   2220
gcttttggg aaaataaaaa aaatctctcc gaacaactac gtggagaaga gctgtctttc   2280
gaagctttat cgctcaacga gacagaagac gatgatgcgg catcgtcgag aattacaaag   2340
ggaagaatct ccgaccgggc caccaggaag tattcggacc tggttccaaa gaattcccct   2400
gggatggttc cattgcacat accagaaggg gaaacaacat tgccgtctca gaattcgaca   2460
gaaggtcgaa gagtaggtgt gaacactcag gagaccatta cagagacagc tgcaacaatt   2520
ataggcacta acggcaacca tatgcagatc tccaccatcg ggataagacc gagctccagc   2580
caaatcccga gttcctcacc gaccacggca ccaagccctg aggctcagac ccccacaacc   2640
cacacatcag gtccatcagt gatggccacc gaggaaccaa caacaccacc gggaagctcc   2700
cccggcccaa caacagaagc acccactctc accacccccag aaaatataac aacagcggtt   2760
aaaactgtcc tgccacagga gtccacaagc aacggtctaa taacttcaac agtaacaggg   2820
attcttggga gtcttgggct tcgaaaacgc agcagaagac aaactaacac caaagccacg   2880
ggtaagtgca atcccaactt acactactgg actcacaaag aacaacataa tgctgctggg   2940
attgcctgga tcccgtactt tggaccgggt gcggaaggca tatacactga aggcctgatg   3000
cataaccaaa atgccttagt ctgtggactt aggcaacttg caaatgaaac aactcaagct   3060
ctgcagcttt tcttaagagc cacaacggag ctgcggacat ataccatact caataggaag   3120
```

```
gccatagatt tccttctgcg acgatggggc gggacatgca ggatcctggg accagattgt    3180
tgcattgagc cacatgattg gacaaaaaac atcactgata aaatcaacca aatcatccat    3240
gatttcatcg acaaccccct acctaatcag gataatgatg ataattggtg gacgggctgg    3300
agacagtgga tccctgcagg aataggcatt actggaatta ttattgcaat tattgctctt    3360
ctttgcgttt gcaagctgct tgctgtgataa tctagacgag atccgaactt gtttattgca    3420
gcttataatg gttacaaata aagcaatagc atcacaaatt tcacaaataa agcatttttt    3480
tcactgcatt ctagttgtgg tttgtccaaa ctcatcaatg tatcttatca tgtctagatc    3540
tgtactgaaa tgtgtgggcg tggcttaagg gtgggaaaga atatataagg tggggggtctt   3600 atgtagtttt gtatctgttt tgcagcagcc gccgccgcca tgagcaccaa ctcgtttgat    3660
ggaagcattg tgagctcata tttgacaacg cgcatgcccc catgggccgg ggtgcgtcag    3720
aatgtgatgg gctccagcat tgatggtcgc cccgtcctgc ccgcaaactc tactaccttg    3780
acctacgaga ccgtgtctgg aacgccgttg gagactgcag cctccgccgc cgcttcagcc    3840
gctgcagcca ccgcccgcgg gattgtgact gactttgctt tcctgagccc gcttgcaagc    3900
agtgcagctt cccgttcatc cgcccgcgat gacaagttga cggctctttt ggcacaattg    3960
gattctttga cccgggaact taatgtcgtt tctcagcagc tgttggatct cgccagcag    4020 gtttctgccc tgaaggcttc ctcccctccc aatgcggttt aaaacataaa taaaaaacca   4080
gactctgttt ggatttggat caagcaagtg tcttgctgtc tttatttagg ggttttgcgc    4140
gcgcggtagg cccgggacca gcggtctcgg tcgttgaggg tcctgtgtat ttttccagg    4200 acgtggtaaa ggtgactctg gatgttcaga tacatgggca taagcccgtc tctggggtgg   4260
aggtagcacc actgcagagc ttcatgctgc ggggtggtgt tgtagatgat ccagtcgtag    4320
caggagcgct gggcgtggtg cctaaaaatg tctttcagta gcaagctgat tgccaggggc    4380
aggcccttgg tgtaagtgtt tacaaagcgg ttaagctggg atgggtgcat acgtgggat    4440 atgagatgca tcttggactg tattttagg ttggctatgt tcccagccat atccctccgg    4500
ggattcatgt tgtgcagaac caccagcaca gtgtatccgg tgcacttggg aaatttgtca    4560
tgtagcttag aaggaaatgc gtggaagaac ttggagacgc ccttgtgacc tccaagattt    4620
tccatgcatt cgtccataat gatggcaatg ggcccacggg cggcggcctg ggcgaagata    4680
tttctgggat cactaacgtc atagttgtgt tccaggatga gatcgtcata ggccattttt    4740
acaaagcgcg ggcggagggt gccagactgc ggtataatgg ttccatccgg cccaggggcg    4800
tagttaccct cacagatttg catttcccac gctttgagtt cagatggggg gatcatgtct    4860
acctgcgggg cgatgaagaa aacggttttcc ggggtagggg agatcagctg ggaagaaagc    4920
aggttcctga gcagctgcga cttaccgcag ccggtgggcc cgtaaatcac acctattacc    4980
ggctgcaact ggtagttaag agagctgcag ctgccgtcat ccctgagcag ggggccact    5040 tcgttaagca tgtccctgac tcgcatgttt tccctgacca aatccgccag aaggcgctcg    5100
ccgcccagcg atagcagttc ttgcaaggaa gcaaagtttt tcaacggttt gagaccgtcc    5160
gccgtaggca tgcttttgag cgtttgacca agcagttcca ggcggtccca cagctcggtc    5220
acctgctcta cggcatctcg atccagcata tctcctcgtt tcgcgggttg ggcggctttt    5280
cgctgtacgg cagtagtcgg tgctcgtcca dacgggccag ggtcatgtct ttccacgggc    5340
gcagggtcct cgtcagcgta gtctgggtca cggtgaaggg gtgcgctccg ggctgcgcgc    5400
tggccagggt gcgcttgagg ctggtcctgc tggtgctgaa gcgctgccgg tcttcgccct    5460
gcgcgtcggc caggtagcat ttgaccatgg tgtcatagtc cagcccctcc gcggcgtggc    5520
```

```
ccttggcgcg cagcttgccc ttggaggagg cgccgcacga ggggcagtgc agacttttga      5580
gggcgtagag cttgggcgcg agaaataccg attccgggga gtaggcatcc gcgccgcagg      5640
ccccgcagac ggtctcgcat ccacgagcc aggtgagctc tggccgttcg gggtcaaaaa       5700
ccaggtttcc cccatgcttt ttgatgcgtt tcttacctct ggtttccatg agccggtgtc      5760
cacgctcggt gacgaaaagg ctgtccgtgt ccccgtatac agacttgaga ggcctgtcct      5820
cgagcggtgt tccgcggtcc tcctcgtata gaaactcgga ccactctgag acaaaggctc      5880
gcgtccaggc cagcacgaag gaggctaagt gggaggggta gcggtcgttg tccactaggg      5940
ggtccactcg ctccagggtg tgaagacaca tgtcgccctc ttcggcatca aggaaggtga      6000
ttggtttgta ggtgtaggcc acgtgaccgg gtgttcctga agggggggcta taaaagggg      6060 tggggcgcg ttcgtcctca ctctcttccg catcgctgtc tgcgagggcc agctgttggg       6120
gtgagtcgac gcgaggctgg atggccttcc ccattatgat tcttctcgct tccggcggca     6180
tcgggatgcc cgcgttgcag gccatgctgt ccaggcaggg agatgacgac catcaggggac    6240 agcttcaagg ccagcaaaag gccaggaacc gtaaaaaggc cgcgttgctg cgttttttcc     6300
ataggctccg ccccccctgac gagcatcaca aaaatcgacg ctcaagtcag aggtggcgaa   6360
acccgacagg actataaaga taccaggcgt ttccccctgg aagctccctc gtgcgctctc    6420
ctgttccgac cctgccgctt accggatacc tgtccgcctt tctcccttcg ggaagcgtgg    6480
cgctttctca tagctcacgc tgtaggtatc tcagttcggt gtaggtcgtt cgctccaagc    6540
tgggctgtgt gcacgaaccc cccgttcagc ccgaccgctg cgccttatcc ggtaactatc    6600
gtcttgagtc aacccggta agacacgact tatcgccact ggcagcagcc actggtaaca    6660
ggattagcag agcgaggtat gtaggcggtg ctacagagtt cttgaagtgg tggcctaact    6720
acggctacac tagaaggaca gtatttggta tctgcgctct gctgaagcca gttaccttcg    6780
gaaaaagagt tggtagctct tgatccggca aacaaaccac cgctggtagc ggtggttttt    6840 ttgttttgcaa gcagcagatt acgcgcagaa aaaaaggatc tcaagaagat cctttgatct    6900
tttctacggg gtctgacgct cagtggaacg aaaaactcacg ttaagggatt ttggtcatga   6960
gattatcaaa aaggatcttc acctagatcc ttttaaatta aaaatgaagt tttaaatcaa    7020
tctaaagtat atatgagtaa acttggtctg acagttacca atgcttaatc agtgaggcac    7080
ctatctcagc gatctgtcta tttcgttcat ccatagttgc ctgactcccc gtcgtgtaga    7140
taactacgat acgggagggc ttaccatctg gccccagtgc tgcaatgata ccgcgagacc    7200
cacgctcacc ggctccagat ttatcagcaa taaaccagcc agccggaagg gccgagcgca    7260
gaagtggtcc tgcaaccttta tccgcctcca tccagtctat taattgttgc cgggaagcta    7320
gagtaagtag ttcgccagtt aatagtttgc gcaacgttgt tgccattgct gcaggcatcg    7380
tggtgtcacg ctcgtcgttt ggtatggctt cattcagctc cggttcccaa cgatcaaggc    7440
gagttacatg atccccatg ttgtgcaaaa aagcggttag ctccttcggt cctccgatcg     7500
ttgtcagaag taagttggcc gcagtgttat cactcatggt tatggcagca ctgcataatt    7560
ctcttactgt catgccatcc gtaagatgct tttctgtgac tggtgagtac tcaaccaagt    7620
cattctgaga atagtgtatg cggcgaccga gttgctcttg cccggcgtca cacgggata    7680 ataccgcgcc acatagcaga actttaaaag tgctcatcat tggaaaacgt tcttcggggc    7740
gaaaactctc aaggatctta ccgctgttga gatccagttc gatgtaaccc actcgtgcac    7800
ccaactgatc ttcagcatct tttactttca ccagcgtttc tgggtgagca aaaacaggaa    7860
ggcaaaatgc cgcaaaaaag ggaataaggg cgacacggaa atgttgaata ctcatactct    7920
```

```
tcctttttca atattattga agcatttatc agggttattg tctcatgagc ggatacatat      7980
ttgaatgtat ttagaaaaat aaacaaatag gggttccgcg cacatttccc cgaaaagtgc      8040
cacctgacgt ctaagaaacc attattatca tgacattaac ctataaaaat aggcgtatca      8100
cgaggccctt tcgtcttcaa gaattgtt                                         8128

<210> SEQ ID NO 9
<211> LENGTH: 676
<212> TYPE: PRT
<213> ORGANISM: Ebola virus (Zaire)

<400> SEQUENCE: 9

Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
           100                 105                 110

Ile Lys Lys Pro Asp Gly Ser Glu Cys Leu Pro Ala Ala Pro Asp Gly
       115                 120                 125

Ile Arg Gly Phe Pro Arg Cys Arg Tyr Val His Lys Val Ser Gly Thr
   130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335
```

-continued

```
Glu Asp His Lys Ile Met Ala Ser Glu Asn Ser Ser Ala Met Val Gln
            340             345             350

Val His Ser Gln Gly Arg Glu Ala Val Ser His Leu Thr Thr Leu
        355             360             365

Ala Thr Ile Ser Thr Ser Pro Gln Ser Leu Thr Thr Lys Pro Gly Pro
    370             375             380

Asp Asn Ser Thr His Asn Thr Pro Val Tyr Lys Leu Asp Ile Ser Glu
385             390             395             400

Ala Thr Gln Val Glu Gln His His Arg Arg Thr Asp Asn Asp Ser Thr
            405             410             415

Ala Ser Asp Thr Pro Ser Ala Thr Ala Ala Gly Pro Pro Lys Ala
            420             425             430

Glu Asn Thr Asn Thr Ser Lys Ser Thr Asp Phe Leu Asp Pro Ala Thr
        435             440             445

Thr Thr Ser Pro Gln Asn His Ser Glu Thr Ala Gly Asn Asn Asn Thr
    450             455             460

His His Gln Asp Thr Gly Glu Glu Ser Ala Ser Ser Gly Lys Leu Gly
465             470             475             480

Leu Ile Thr Asn Thr Ile Ala Gly Val Ala Gly Leu Ile Thr Gly Gly
            485             490             495

Arg Arg Thr Arg Arg Glu Ala Ile Val Asn Ala Gln Pro Lys Cys Asn
            500             505             510

Pro Asn Leu His Tyr Trp Thr Thr Gln Asp Glu Gly Ala Ala Ile Gly
            515             520             525

Leu Ala Trp Ile Pro Tyr Phe Gly Pro Ala Ala Glu Gly Ile Tyr Ile
    530             535             540

Glu Gly Leu Met His Asn Gln Asp Gly Leu Ile Cys Gly Leu Arg Gln
545             550             555             560

Leu Ala Asn Glu Thr Thr Gln Ala Leu Gln Leu Phe Leu Arg Ala Thr
            565             570             575

Thr Glu Leu Arg Thr Phe Ser Ile Leu Asn Arg Lys Ala Ile Asp Phe
            580             585             590

Leu Leu Gln Arg Trp Gly Gly Thr Cys His Ile Leu Gly Pro Asp Cys
        595             600             605

Cys Ile Glu Pro His Asp Trp Thr Lys Asn Ile Thr Asp Lys Ile Asp
    610             615             620

Gln Ile Ile His Asp Phe Val Asp Lys Thr Leu Pro Asp Gln Gly Asp
625             630             635             640

Asn Asp Asn Trp Trp Thr Gly Trp Arg Gln Trp Ile Pro Ala Gly Ile
            645             650             655

Gly Val Thr Gly Val Val Ile Ala Val Ile Ala Leu Phe Cys Ile Cys
            660             665             670

Lys Phe Val Phe
            675
```